(12) United States Patent
Kim et al.

(10) Patent No.: US 10,274,446 B2
(45) Date of Patent: Apr. 30, 2019

(54) MEMBER FOR GAS SENSOR, HAVING A METAL OXIDE SEMICONDUCTOR TUBE WALL WITH MICROPORES AND MACROPORES, GAS SENSOR, AND METHOD FOR MANUFACTURING SAME

(71) Applicant: KOREA ADVANCED INSTITUTE OF SCIENCE AND TECHNOLOGY, Daejeon (KR)

(72) Inventors: Il-Doo Kim, Daejeon (KR); Ji Su Jang, Daejeon (KR); Sang-Joon Kim, Daejeon (KR); Seon-Jin Choi, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 206 days.

(21) Appl. No.: 15/111,173

(22) PCT Filed: Dec. 15, 2015

(86) PCT No.: PCT/KR2015/013707
§ 371 (c)(1),
(2) Date: Jul. 12, 2016

(87) PCT Pub. No.: WO2016/105012
PCT Pub. Date: Jun. 30, 2016

(65) Prior Publication Data
US 2016/0334359 A1    Nov. 17, 2016

(30) Foreign Application Priority Data

Dec. 23, 2014  (KR) .................. 10-2014-0186846
Mar. 11, 2015  (KR) .................. 10-2015-0034024
Oct. 23, 2015  (KR) .................. 10-2015-0148273

(51) Int. Cl.
*C01B 32/168* (2017.01)
*G01N 27/12* (2006.01)
(Continued)

(52) U.S. Cl.
CPC ......... *G01N 27/127* (2013.01); *C01B 32/168* (2017.08); *C01G 9/02* (2013.01);
(Continued)

(58) Field of Classification Search
CPC .... B82Y 15/00; G01N 27/127; C01B 32/168; C01G 9/02; C01G 19/02; C01G 23/003;
(Continued)

(56) References Cited

FOREIGN PATENT DOCUMENTS

KR    10-2014-0015897 A    2/2014
KR       10-1400605 B1    5/2014
KR    10-2014-0136070 A    11/2014

OTHER PUBLICATIONS

Xiao, Fangxing. "Layer-by-layer self-assembly construction of highly ordered metal-TiO2 nanotube arrays heterostructures (M/TNTs, M=Au, Ag, Pt) with tunable catalytic activities." The Journal of Physical Chemistry C 116.31 (2012): 16487-16498.*
(Continued)

*Primary Examiner* — Richard M Rump
(74) *Attorney, Agent, or Firm* — Fenwick & West LLP

(57) ABSTRACT

Disclosed are a gas sensor member, a gas sensor using the same, and manufacturing methods thereof, and specifically, a gas sensor member using a one-dimensional porous metal oxide nanotube composite material having a double average pore distribution in which mesopores (0.1 nm to 50 nm) and macropores (50 nm to 300 nm) are simultaneously formed on the surface of a nanotube through decomposition of a spherical polymer sacrificial template and continuous crystallization and diffusion of a metal oxide and a nanoparticle catalyst embedded in an apoferritin is uniformly loaded in
(Continued)

the inside and on the outer wall and inner wall of a one-dimensional metal oxide nanotube through a high-temperature heat treatment, a gas sensor using the same, and manufacturing methods thereof are disclosed.

14 Claims, 33 Drawing Sheets

(51) Int. Cl.
    *C01G 49/02*     (2006.01)
    *C01G 19/02*     (2006.01)
    *C01G 45/02*     (2006.01)
    *C01G 9/02*     (2006.01)
    *C01G 23/00*     (2006.01)
    *B82Y 15/00*     (2011.01)

(52) U.S. Cl.
    CPC ........... *C01G 19/02* (2013.01); *C01G 23/003* (2013.01); *C01G 45/02* (2013.01); *C01G 49/02* (2013.01); *B82Y 15/00* (2013.01)

(58) Field of Classification Search
    CPC .. C01G 23/005; C01G 23/006; C01G 23/047; C01G 25/006; C01G 25/02; C01G 31/02; C01G 35/02; C01G 35/006; C01G 39/02; C01G 41/02; C01G 45/02; C01G 51/02; C01G 51/68; C01G 53/02; C01G 55/004; C01G 49/02
    See application file for complete search history.

(56) References Cited

OTHER PUBLICATIONS

Choi, Seon-Jin, et al. "Coaxial electrospinning of WO 3 nanotubes functionalized with bio-inspired Pd catalysts and their superior hydrogen sensing performance." Nanoscale 8.17 (2016): 9159-9166.*
Niu, T., L. M. Shen, and Y. Liu. "Preparation of meso-macroporous α-alumina using carbon nanotube as the template for the mesopore and their application to the preferential oxidation of CO in H 2-rich gases." Journal of Porous Materials 20.4 (2013): 789-798.*
PCT International Search Report, PCT/KR2015/013707, dated Apr. 19, 2016, 4 Pages.
Kim, Sang Jun, et al., "Highly Sensitive and Fast Responding Exhaled Breath Sensor using WO3 Nanofibers Functionalized by Apoferritin-Encapsulated Pt Nanoparticles for the Diagnosis of Diabetes," European Health Psychology Society, Apr. 29, 2014, 2 pages.
Qiu, H., et al., "Ferritin-Templated Synthesis and Self-Assembly of Pt Nanoparticles on a Monolithic Porous Graphene Network for Electrocatalysis in Fuel Cells," ACS Applied Materials & Interfaces, Jan. 18, 2013, vol. 5, No. 3, pp. 782-787.

* cited by examiner

MEMBER FOR GAS SENSOR, HAVING A METAL OXIDE SEMICONDUCTOR TUBE WALL WITH MICROPORES AND MACROPORES, GAS SENSOR, AND METHOD FOR MANUFACTURING SAME

TECHNICAL FIELD

Embodiments of the inventive concepts described herein relate to an optimal sensing material structure in which the diffusion and reaction of a gas take place rapidly and a manufacturing method thereof. More particularly, embodiments of the inventive concepts relate to a metal oxide semiconducting nanotube that is functionalized with a catalytic particle simultaneously including mesopores and macropores which are formed during the simultaneous high-temperature decomposition of a metal particle and a spherical polymer which are encapsulated in a protein and embedded in an electrospun metal salt precursor/polymer composite nanotube as sacrificial templates and has a double average surface pore distribution, a gas sensor member and a gas sensor which use the same, and manufacturing methods thereof.

BACKGROUND

Recently, as the social interest in the health care has increased, the development of gas sensors that are based on a metal oxide semiconductor and intended to detect harmful environmental gases have been actively carried out for the detection of volatile organic compound gases in the exhaled breath and the measurement of air quality. Such gas a sensor based on a metal oxide semiconductor senses a gas by measuring the electrical resistance which changes in the adsorption and desorption processes of a specific gas to be detected by the interaction with the oxygen ion adsorbed onto the metal oxide surface. In particular, a metal oxide gas sensor has an advantage of being easily miniaturized, and thus a study to mount the gas sensor to a portable device or a wearable device has recently been attempted from a commercial point of view. In addition, it also has an advantage that the price is inexpensive, and thus it is widely applied in society as a harmful environment gas detector, a breathalyzer, an air pollution detector, an anti-terrorism gas sensor, and the like. Particularly, in recent years, a possibility has been proposed that a variety of diseases such as diabetes, nephritis, asthma, halitosis, lung cancer can be diagnosed by detecting a significantly small amount of a volatile organic compound gas, such as acetone, ammonia, nitrogen monoxide, hydrogen sulfide, or toluene, that is contained in the exhaled breath and associated with the biological metabolism using the superior detection capability of the metal oxide sensor. In practice, however, it is required to be able to sense such a biomarker gas having a significantly low concentration in a range of from 10 ppb (parts per billion) to 10 ppm (parts per million) with a high speed of a few seconds and a high sensitivity in order to diagnose the disease at an early stage by using the biomarker gas. In particular, it is required to react with a specific target biomarker gas among the thousands of mixed gases contained in the exhaled breath with a high sensitivity, and thus it is significantly important to develop a sensing material exhibiting high selectivity to the gas to be measured.

In order to equip a gas sensor based on a metal oxide semiconductor with ultrahigh sensitivity/high selectivity, the development of the gas sensor based on a variety of nanostructures including nanoparticles, nanofibers, and nanotubes have recently been studied. As mentioned above, the metal oxide-based gas sensor utilizes the surface reaction of the sensing material with the gas to be detected, and thus a higher sensitivity is expected as the surface area of the sensing material on which the reaction with the gas molecule to be detected takes place is wider. From this point of view, the nanostructure sensing material exhibits excellent gas detection characteristics since it has a relative wider area for the reaction with a gas as compared with a thick film material or a thin film material, and the nanostructure sensing material has a porous structure through which the gas molecules can sufficiently rapidly diffuse into the sensing material and thus high-speed response characteristics can be induced. In particular, in the case of a one-dimensional porous metal oxide nanotube having mesopores and macropores, the surface area can be expected to be from 2 to 10 times nanofibers having a thin film structure, thus high detection characteristics are expected, and pores having various sizes are distributed on the tube surface, thus the gas molecules freely moves as compared with the dense nanofiber and nanotube structures and the characteristics of the sensor can be maximized. Additionally, the catalytic effect can be maximized even with a small amount of catalyst if the catalytic nanoparticles are uniformly loaded on the one-dimensional porous nanotube without aggregation with one another. In addition, in order to maximize the catalytic effect, rather than a structure in which the catalyst is embedded in a dense sensing material so as not to be able to react with the gas, it is ideal that the sensing material is functionalized such that the catalyst is exposed to the surface thereof and thus the catalytic reaction with the gas is maximized. Such catalysts are largely classified into two types, and there are a metal catalyst such as platinum (Pt) or gold (Au) used in a chemical sensitization method in which the characteristics of the gas sensor are enhanced by increasing the concentration of the gas participating in the surface reaction by the use such a metal catalyst and a metal catalyst such as palladium (Pd), nickel (Ni), cobalt (Co), or silver (Ag) used in an electronic sensitization method in which the sensitivity is improved by a change in oxidation state due to the formation of a metal oxide such as PdO, NiO, $Co_2O_3$, or $Ag_2O$.

As described above, although studies to utilize sensing materials formed by loading various nanoparticle catalysts together with the development of various nanostructures have been continued, it is the reality that a sensing material that is based on a oxide material semiconductor and can precisely sense a trace amount, less than hundreds ppb, of gas at a high speed has not yet been commercialized, and it is significantly important to develop a sensing material which can sense a trace amount of gas and to clearly recognize the pattern of the detected result by imparting selectivity to various kinds of gases for the realization of a exhaled breath sensor to diagnose the disease at the early stage.

From the viewpoint of the synthesis of a sensing material having a nanostructure, a number of studies on the method to manufacture nanostructures through a chemical vapor deposition method, a physical deposition method, and a chemical growth method have been carried out. However, these methods include a complicated and cumbersome manufacturing process upon the synthesis of nanostructures, and thus there are problems such as difficulties in mass production, an expensive process cost, and a long processing time, which are a major challenge to commercialization.

In addition, from the viewpoint of the nanoparticle catalyst to be loaded to the sensing material, the most effective catalytic action is induced when the catalyst is uniformly dispersed without aggregation in the entire area of the sensing material. In this respect, it is difficult to optimize the sensing characteristics since the aggregation of nanoparticles is hardly avoided during the synthesis of nanoparticles utilizing the polyol process and the loading by the mixing of the catalyst particles and the sensing material which are widely used in the conventional sensor field.

In order to overcome these disadvantages in the conventional sensor synthesis, an ideal nanostructure that is formed by a simple and effective method, has a wide surface area, and includes both mesopores and macropores which lead rapid diffusion and reaction of the gas and a process technology which can functionalize the sensor with a nanoparticle catalyst having a nano-size by thoroughly dispersing without aggregation are required. In addition, a process technology which satisfies the two matters described above at the same time and thus contribute to the development of a sensor which can selectively sense a significantly amount of biomarker gas contained in the actual human exhaled breath, recognize the pattern, and ultimately distinguish the patient with the disease.

SUMMARY

Embodiments of the inventive concepts provide method for synthesizing a one-dimensional porous metal oxide nanotube through electrospinning, in which a spherical polymer colloid which plays a role of the sacrificial template and forms macropores is dispersed in an electrospinning solution, macropores (50 nm to 300 nm) are formed on the nanotube surface via thermal decomposition of the spherical polymer template (>200 nm) by a high-temperature heat treatment after electrospinning, and sequentially, mesopores (0.1 nm to 50 nm) are formed on the nanotube surface through the macropores covering effect and thermal decomposition of the protein template (12 nm) by diffusion of the metal oxide generated when the tube is formed at the same time. Embodiments of the inventive concepts also provide a method for manufacturing a one-dimensional porous metal oxide nanotube which is uniformly loaded with a nanoparticle catalyst and has a double average pore distribution composed of macropores (50 nm to 300 nm) and mesopores (0.1 nm to 50 nm) through electrospinning, in which a highly dispersible protein-based nanoparticle catalyst is dispersed in an electrospinning solution.

In particular, a technique for synthesizing a sensing material exhibiting high sensitivity and high selectivity and a catalyst uniformly distributed on a one-dimensional porous metal oxide nanotube, in which a polymer sacrificial template having a size of 200 nm or more is used, macropores (50 nm-300 nm) are formed on the surface of a fiber through decomposition of the polymer template by the high temperature heat treatment, sequentially, in order to form a metal oxide nanotube, the metal oxide diffuses toward the macropores formed on the surface so that a part of the macropores is filled and mesopores having a size distribution of from 0.1 nm to 50 nm are additionally formed on the nanotube surface, and uniform distribution of the catalyst and the formation mesopores are facilitated as a protein-based highly dispersible nanoparticle catalyst is used, and an application technique of a gas sensor using the same are proposed. The protein template the so-called apoferritin that is used in the inventive concept is a spherical hollow protein material having an empty space of about 8 nm, and thus it is possible to provide a method for synthesizing a metal oxide nanotube containing a nanoparticle catalyst through electrospinning, in which a nanoparticle catalyst is embedded in the empty space of the apoferritin protein and the nanotube is functionalized with the apoferritin particles embedding the nanoparticle catalyst.

In particular, a technique for synthesizing a ultra-sensitive nanotube sensing material which can satisfy an increase in specific surface area to be an important indicator of the gas sensing characteristics and a catalytic effect at the same time as a metal oxide nanotube structure having a large surface area is synthesized through the Ostwald ripening phenomenon although a metallic nanoparticle catalyst is contained after the high-temperature heat treatment and the nanoparticle catalyst is also uniformly dispersed on the shell constituting the nanotube, an application technique of a gas sensor using the same are proposed.

In order to solve the problem of the prior art, it is intended to provide a gas sensor member capable of detecting a trace amount of gas by easily synthesizing a metal oxide nanotube structure in which nanoparticle catalysts having a significantly small (1 nm to 3 nm) size are uniformly dispersed and loaded on the outside and inside of a metal oxide without being aggregated with one another, and at the same time, a great number of mesopores (0.1 nm to 50 nm) and macropores (50 nm to 300 nm) are formed by single electrospinning and the post-heat treatment, a gas sensor using the same, and manufacturing methods thereof.

One aspect of embodiments of the inventive concept is directed to provide a method for manufacturing a sensing material including a one-dimensional porous metal oxide nanotube on which a nanoparticle catalyst is uniformly loaded and mesopores and macropores are formed at the same time and a gas sensor member using the same, using a single process in which a nanoparticle catalyst exhibiting superior dispersibility due to the surface charge properties is synthesized and a spherical polymer sacrificial template colloid exhibiting excellent dispersibility is applied to an electrospinning solution at the same time. The method for manufacturing a sensing material and a gas sensor member using the same according embodiments of the inventive concept includes a method for manufacturing a catalyst-metal oxide nanotube composite sensing material having a double surface pore distribution for a gas sensor capable of detecting a harmful environmental gas and a biomarker gas for diagnosis of a disease, including: (a) a step of synthesizing a dispersion in which a metallic nanoparticle catalyst encapsulated in a protein and embedded in an inner hollow structure of an apoferritin is uniformly dispersed; (b) a step of preparing an electrospinning solution by mixing the dispersion in which a metallic nanoparticle catalyst encapsulated in a protein and embedded in an inner hollow structure of an apoferritin is uniformly dispersed with a dispersion of a spherical polymer sacrificial template and mixing the mixed dispersion with a solution in which a metal oxide precursor (metal salt precursor) and a polymer are dissolved; (c) a step of forming a composite nanofiber in which at least one or more spherical polymer sacrificial templates and a plurality of the metallic nanoparticle catalysts embedded in an inner hollow structure of the apoferritin protein are uniformly distributed on the surface and in the inside of the metal oxide precursor/polymer composite nanofiber from the electrospinning solution using an electrospinning method; (d) a step of forming macropores (50 nm to 300 nm) on the fiber surface through thermal decomposition of the polymer sacrificial template by a high-temperature heat treatment, sequentially forming mesopores having a size distribution of from 0.1 nm to 50 nm by filling a part of the macropores with the metal oxide which diffuses toward the macropores formed on the surface so as to form a metal oxide nanotube, and uniformly loading the nanoparticle catalyst based on the protein in the composite nanofiber to the porous nanotube by allowing the nanoparticle catalyst to diffuse outward; and (e) a step of fabricating a resistance change-type semiconductor gas sensor by dispersing or grinding the porous metal oxide nanotube in which the nanoparticle catalyst having a double surface pore distribution is uniformly loaded in the inside and on the inner surface and outer surface of the shell constituting the nanotube and mesopores and macropores are formed and coating it on a sensor electrode for a semiconductor type gas sensor using at least one coating method among drop coating, spin coating, ink-jet printing, and dispensing.

Here, in the step (a), the apoferritin is a protein that is obtained by removing the iron component from a ferritin protein which is present in the mucosal cells of the small intestine and contains an iron component and has a (hollow) structure with an empty space of about 8 nm, and the overall size of the apoferritin is 12 nm. A variety of metal ions can diffuse and enter the inside of the hollow structure of the apoferritin, and various kinds of nanoparticle catalyst can be easily synthesized through reduction. The kind and form of the metal salt which can be substituted into the inside of the apoferritin may significantly vary, and representative examples of the catalyst in a salt form may include copper (II) nitrate, copper(II) chloride, cobalt(II) nitrate, cobalt(II) acetate, lanthanum(III) nitrate, lanthanum(III) acetate, platinum(IV) chloride, platinum(II) acetate, gold(I, III) chloride, gold(III) acetate, silver chloride, silver acetate, Iron(III) chloride, Iron(III) acetate, nickel(II) chloride, nickel(II) acetate, ruthenium(III) chloride, ruthenium acetate, iridium (III) chloride, iridium acetate, tantalum(V) chloride, and palladium(II) chloride. The kind of the metal salt is not particularly limited as long as it is in the form of a salt containing a metal ion, single metal particles are formed in the hollow portion of the apoferritin in the case of using a single metal, and the binding force between the same kind of metals is strong so that the phases have a segregated form and bonding between heterogeneous metals is facilitated and thus it is possible to synthesize a nanoparticle catalyst formed in the hollow portion of the apoferritin in a metal alloy form having a strong binding force in the case of synthesizing using two metal salts at the same time. In the case of the nanoparticle catalyst that is synthesized as being embedded in the hollow structure of the apoferritin, the surface thereof is surrounded by a protein having a surface charge, and thus the nanoparticle catalysts can maintain an effectively dispersed state without aggregation with one another.

In addition, the step (b) is a step of preparing an electrospinning solution used in electrospinning, and the electrospinning solution can be prepared by dissolving a polymer which acts as the template for effectively synthesizing the nanofiber during the electrospinning and a metal oxide precursor in a solvent. Examples of the representative polymer used at this time may include polymethyl methacrylate (PMMA), polyvinylpyrrolidone (PVP), polyvinyl acetate (PVAc), polyvinyl alcohol (PVA), polyacrylonitrile (PAN), polyethylene oxide (PEO), polypropylene oxide (PPO), polyethylene oxide copolymer, polypropylene oxide copolymer, polycarbonate (PC), polyvinylchloride (PVC), polycaprolactone, and polyvinylidene fluoride, and examples of the representative metal salt may include acetate, chloride, acetylacetonate, nitrate, methoxide, ethoxide, butoxide, isopropoxide, and sulfide which contain a metal salt. Additionally, it is possible to prepare an electrospinning solution in a colloidal form by uniformly dispersing a solution of the nanoparticle catalyst that is synthesized in the step (a) and encapsulated in the apoferritin protein and spherical polymer sacrificial template colloids which exhibits excellent dispersibility in an electrospinning solution. The spherical polymer sacrificial template used for the formation of macropores refers to a template that can be removed during the high-temperature heat treatment, and the kind of the template is not particularly limited. Specifically, it may be one kind or a mixture of two or more kinds selected from polymethyl methacrylate (PMMA), polyvinylpyrrolidone (PVP), polyvinyl acetate (PVAc), polyvinyl alcohol (PVA), polystyrene (PS), polyacrylonitrile (PAN), polyvinylidene fluoride (PVDF), polyacrylic acid (PAA), polydiallydimethylammonium chloride (PDADMAC), or polystyrene sulfonate (PSS). In addition, the sacrificial template has a size in the range of from 50 nm to 1 μm, the sacrificial template is preferably dispersed without being decomposed when mixed with an electrospinning solution, and a polymer colloid that is insoluble in a solvent since a charged ion or a charged anionic or cationic surfactant is formed on the surface of the colloid may be used as the sacrificial template although the sacrificial colloid is a polymer soluble in the solvent.

In addition, the step (c) is a step of synthesizing a metal salt/polymer composite nanofiber on which the metallic nanoparticles (metallic nanoparticle catalyst) and the spherical polymer sacrificial template (polymeric beads) are uniformly loaded using the electrospinning method. The composite nanofiber has a rugged shape due to the polymer sacrificial template embedded therein.

In the step (d), the polymer constituting the polymer/metal oxide precursor composite nanofiber is decomposed and removed through the high-temperature heat treatment, and at the same time, the apoferritin protein shell surrounding the nanoparticle catalyst and the spherical polymer sacrificial template are removed. Specifically, the macropores formed on the nanofiber surface are generated as the polymer having a size of 200 nm or more is decomposed through the high-temperature heat treatment, sequentially, the metal oxide is crystallized and diffuses outward to partially cover the macropores in the course of the formation of metal oxide nanotubes, as a result, a number of mesopores are formed.

In addition, the formation of mesopores is also attributed to the decomposition of the apoferritin particles that are densely gathered in between the plurality of polymer sacrificial templates. In particular, the heating rate plays an important role in the formation of the nanotube structure. In the case of conducting the heat treatment at a high heating rate of 10° C./min, it is possible to more effectively synthesize the one-dimensional porous metal oxide nanotube having a double pore distribution (mesopores and macropores coexist) in which the metallic nanoparticle catalyst obtained by the decomposition of the apoferritin protein having the nanoparticle catalyst formed inside the hollow structure is included in the metal oxide nanotube structure. On the other hand, the nanotube structure may not be formed in the case of conducting the heat treatment at a relatively low heating rate of 4° C./min.

The step (e) may be a step of coating a dispersion prepared by dispersing the one-dimensional porous metal oxide nanotube having a double pore distribution obtained in the step (d) in a solvent on a sensor electrode (an alumina insulating substrate on which parallel electrodes capable of measuring the electrical conductivity and the electrical resistance are formed) that is prepared in advance using a coating method such as drop coating, spin coating, ink-jet printing, or dispensing. Here, the coating method is not particularly limited as long as it is a method by which the one-dimensional porous metal oxide nanotube which contains a nanoparticle catalyst and has a double pore distribution can be uniformly coated.

In the one-dimensional porous metal oxide nanotube structure that is thus fabricated and has a double pore distribution, the thickness between the inner and outer walls can be determined in a length range of from 10 nm to 50 nm, and the diameter of the nanotube may be in a length range of from 50 nm to 5 μm. The length of the nanotube may be in a length range of from 1 μm to 100 μm. In addition, the nanotube structure includes a plurality of mesopores in a range of from 0.1 nm to 50 nm and macropores in a size range of from 50 nm to 300 nm on the outer surface of the tube.

Another aspect of embodiments of the inventive concept is directed to provide a method for manufacturing a sensing material including a nanoparticle catalyst which has a large surface area and is uniformly distributed at the same time as a nanoparticle catalyst exhibiting superior dispersibility is synthesized and is uniformly loaded in the inside and on the outside of the one-dimensional metal oxide nanotube synthesized by an easy single process and a gas sensor member using the same. This method relates to a method for manufacturing a gas sensor member in which catalyst particles exhibiting high dispersibility is singly loaded on a nanotube without mixing the catalyst particles with the polymer template described above. The method for manufacturing a sensing material and a gas sensor member using the same according to embodiments of the inventive concept includes (a) a step of synthesizing a nanoparticle catalyst using an apoferritin; (b) a step of preparing a metal oxide precursor/polymer mixed electrospinning solution containing the nanoparticle catalyst contained (embedded) in the hollow structure of the apoferritin; (c) a step of forming a metal oxide precursor/polymer composite nanofiber containing a nanoparticle catalyst embedded in the hollow structure of the apoferritin on the surface or in the inside of the metal oxide precursor/polymer composite nanofiber using an electrospinning method; (d) a step of removing the apoferritin of a protein component encapsulating the nanoparticle catalyst and the polymer substance through thermal decomposition by a high-temperature heat treatment at a high heating rate and forming a one-dimensional metal oxide nanotube containing the nanoparticle catalyst in the shell through the Ostwald ripening; and (e) a step of dispersing the metal oxide nanotube substance loaded with the metallic nanoparticle catalyst and coating it on an electrode for a gas sensor by drop to fabricating a gas sensor, and the method may further include (f) a step of fabricating at least two or more kinds of metal oxide nanotube sensors loaded with the nanoparticle catalyst in combination of different nanoparticle catalysts or different metal oxide sensing materials to constitute a sensor array. The method includes a method for manufacturing a structure containing a nanoparticle catalyst that is uniformly dispersed on the surface and in the inside of the one-dimensional nanotube through single electrospinning according to the process described above.

Here, the step (a) is the same as the step of synthesizing the nanoparticle catalyst in the process to manufacture a nanotube having mesopores and macropores.

In addition, the step (b) is a step of preparing an electrospinning solution used in electrospinning, and the electrospinning solution can be prepared by dissolving a polymer which acts as the template for easily forming the nanofiber and a metal oxide which acts as the precursor in a solvent. Specific examples of the polymer may include polymethyl methacrylate (PMMA), polyvinylpyrrolidone (PVP), polyvinyl acetate (PVAc), polyvinyl alcohol (PVA), polyacrylonitrile (PAN), polyethylene oxide (PEO), polypropylene oxide (PPO), polyethylene oxide copolymer, polypropylene oxide copolymer, polycarbonate (PC), polyvinylchloride (PVC), polycaprolactone, and polyvinylidene fluoride, and examples of the representative metal salt may include acetate, chloride, acetylacetonate, nitrate, methoxide, ethoxide, butoxide, isopropoxide, and sulfide which contain a metal salt. Additionally, it is possible to prepare an electrospinning solution by adding the apoferritin protein having the nanoparticle catalyst that is synthesized in the step (a) formed in the hollow structure thereof. In the case of preparing the electrospinning solution, the concentration of the apoferritin protein having the nanoparticle catalyst formed in the hollow structure thereof can be variously controlled in a range of from 0.001 wt % to 50 wt %. The content of the nanoparticle catalyst contained in the shell of the metal oxide nanotubes is controlled depending on to the concentration of the apoferritin protein.

In addition, the step (c) is a step of synthesizing a metal salt/polymer composite nanofiber using an electrospinning method, and the apoferritin protein having the nanoparticle catalyst that is synthesized in the step (a) formed in the hollow structure thereof is uniformly distributed in the inside of the metal oxide precursor/polymer composite nanofiber due to excellent dispersibility of the apoferritin protein.

In addition, in the step (d), the polymer constituting the polymer/metal oxide precursor composite nanofiber the is decomposed and removed through a high-temperature heat treatment, and the metal oxide precursor undergoes the oxidation and the Ostwald ripening, thus it is possible to form a metal oxide nanotube structure having a one-dimensional structure and contains a nanoparticle catalyst. In particular, the heating rate plays an important role in the formation of the nanotube structure. In the case of conducting the heat treatment at a high heating rate of 10° C./min, it is possible to more effectively synthesize the metal oxide nanotube containing the metallic nanoparticle catalyst obtained by the decomposition of the apoferritin protein having the nanoparticle catalyst formed inside the hollow structure in the shell structure. On the other hand, the nanotube structure may not be formed in the case of conducting the heat treatment at a relatively low heating rate of 4° C./min.

The step (e) may be a step of coating a dispersion prepared by dispersing the polycrystalline metal oxide nanotubes loaded with nanoparticle catalyst obtained in the step (d) in a solvent on a sensor electrode (an alumina insulating substrate on which parallel electrodes capable of measuring the electrical conductivity and the electrical resistance are formed) that is prepared in advance using a coating method such as drop coating, spin coating, ink-jet printing, or dispensing. Here, the coating method is not particularly limited as long as it is a method by which the polycrystalline nanotube containing the metallic nanoparticle catalyst obtained by the decomposition of the apoferritin protein having the nanoparticle catalyst formed inside the hollow structure in the shell structure can be uniformly coated.

In addition, here, in the step (f), the sensor that is fabricated in the step (e) and has a metal oxide nanotube structure containing a nanoparticle catalyst may be formed into a sensor array constituted by two or more kinds of composite sensing materials including various kinds of nanoparticle catalyst-metal oxide nanotube composite sensing materials having a combination of different nanoparticle catalysts and different metal oxide nanotubes having a one-dimensional structure.

In the one-dimensional metal oxide nanotube structure fabricated above, the thickness between the inner and outer walls can be determined in a length range of from 10 nm to 50 nm, and the length of the nanotube may be in a length range of from 1 μm to 500 μm.

Here, in the case of the sensing material fabricated above, the nanoparticle catalyst is intensively and uniformly contained in the shell portion constituting the metal oxide nanotube so that the catalytic properties and the sensitivity of the sensing material can be maximized at the same time.

The weight ratio of the nanoparticle catalyst in the nanoparticle catalyst-metal oxide nanotube composite sensing material fabricated by the method described above can be selected from a range of from 0.001 wt % to 50 wt % with respect to the weight of the metal oxide nanotube, and the nanoparticle catalyst-metal oxide nanotube composite sensing material can sense specific gases contained in the exhaled breath of a human body to determine the presence or absence of disease and also can sense the harmful gas in the indoor and outdoor environment.

Embodiments of the inventive concept is characterized in that nanoparticle catalysts having a size of from 1 nm to 3 nm are formed using a protein template exhibiting excellent dispersibility due to the repulsive force therebetween since the surface of the protein template is positively charged, the nanoparticle catalysts thus formed are mixed into the electrospinning solution, a spherical template colloid is also mixed into the electrospinning solution, and the spherical template and the catalyst are uniformly distributed on the composite nanofiber by electrospinning. In addition, embodiments of the inventive concept is characterized in that the Ostwald ripening and the polymer decomposition due to a high heating rate in the high-temperature heat treatment are used to form a one-dimensional porous metal oxide structure on which the nanoparticle catalyst is uniformly loaded and in which two kinds of pores and distributed on the metal oxide surface. An effect of disclosing a gas sensor member and a gas sensor which can be manufactured on a large scale and manufacturing methods thereof is obtained by controlling the shape which increase the catalytic effect and reaction surface area to be important factors in the gas sensing characteristics so as to exhibit high sensitivity characteristics to be able to detect a trace amount of gas of about 10 parts per billion, variously changing the material composition so as to exhibit excellent selectivity to be able to detect a variety of gases, controlling the electrospinning and the heat treatment, and controlling the shape of the nanotube that is loaded with a catalyst and includes a number of pores through a simple process at the same time.

According to embodiments of the inventive concept, a spherical polymer sacrificial template is used when synthesizing a one-dimensional porous metal oxide nanotube having a plurality of circular or elliptical mesopores and a number of macropores, a one-dimensional porous nanotube structure having mesopores and macropores on the surface of the nanotubes is formed by a single process using the time difference between the polymer decomposition and the crystallization and diffusion of the metal oxide, a porous rube structure having a specific surface area to be several ten times as large as that of a general thin-film structure and to be several times as large as that of a dense tube structure using the protein templates that are densely gathered in between a plurality of polymers. An effect of improving the sensing characteristics is obtained as gas molecules smoothly flow through the pores present on the tube surface and the adsorption and desorption of the gas molecules to the metal oxide nanotube surface is facilitated. In addition, the nanoparticle catalyst encapsulated in the apoferritin is contained in the electrospinning solution, the protein encapsulating the nanoparticle catalyst is all removed through the high-temperature heat treatment after being electrospun, the nanoparticles having a size in a range of from 1 nm to 3 nm are exposed on a newly formed surface by being diffused through the inner wall and the outer wall and the pores of the porous nanotube during the Ostwald ripening, and thus the catalytic reaction effect can be maximized. The protein having an inner hollow size of 8 nm can additionally form ultra-micro pores on the surface of the nanotubes while being removed. As described above, an effect of disclosing a gas sensor member and a gas sensor which can be manufactured on a large scale, exhibit high sensitivity characteristics to be able to detect a trace amount of gas, and exhibit excellent selectivity to be able to detect a specific gas, and manufacturing methods thereof is obtained as the sensing characteristics are maximized through the shape control and catalytic reaction effect of the gas sensor member.

According to embodiments of the inventive concept, as the nanotube structure is formed by a single process by controlling the heat treatment conditions upon fabricating a hollow fiber having a one-dimensional metal oxide nanotube structure, the hollow fiber has a specific surface area to be 6 times as large as that of a general thin-film structure, the movement of the gas into the tube is facilitated, and an effect of improving the sensitivity for a small amount of gas is obtained. In addition, it is possible to maximize the catalytic reaction by manufacture a gas sensor using a sensing material in which the nanoparticle catalysts are uniformly loaded on the inner wall and the outer wall of the metal oxide nanotube without aggregation as the nanoparticle catalysts encapsulated inside the apoferritin are contained in the electrospinning solution and subjected to a high-temperature heat treatment after being electrospun. As described above, an effect of disclosing a gas sensor member and a gas sensor which can be manufactured on a large scale, exhibit high sensitivity characteristics to be able to detect a trace amount of gas, and exhibit excellent selectivity to be able to detect a specific gas, and manufacturing methods thereof is obtained by maximizing the surface area and catalytic reaction effect of the gas sensor member.

BRIEF DESCRIPTION OF THE FIGURES

The inventive concepts will become more apparent in view of the attached drawings and accompanying detailed description.

DETAILED DESCRIPTION

Figure 1:
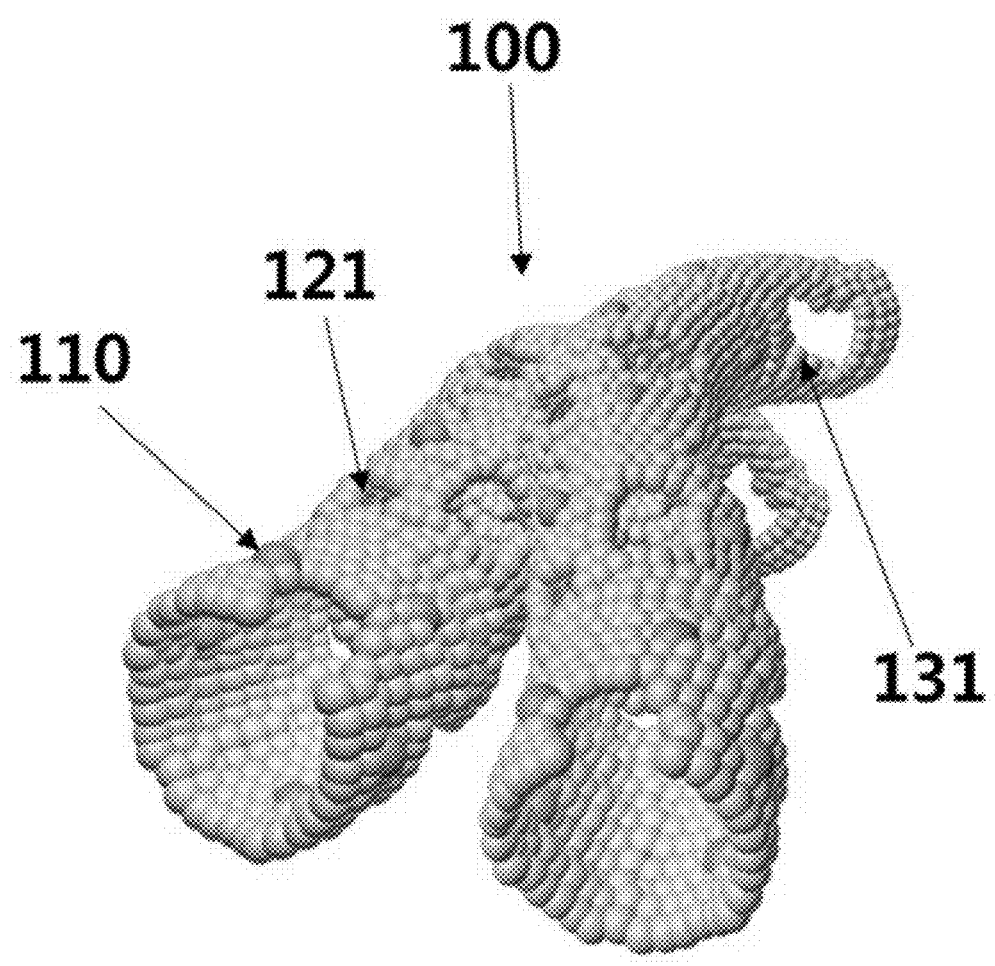
FIG. 1 is a schematic diagram of a gas sensor member using a one-dimensional porous metal oxide nanotube which is uniformly loaded with a nanoparticle catalyst and includes a plurality of circular or elliptical mesopores and macropores according to an embodiment of the inventive concept.

The inventive concepts will now be described more fully hereinafter with reference to the accompanying drawings, in which exemplary embodiments of the inventive concepts are shown. The advantages and features of the inventive concepts and methods of achieving them will be apparent from the following exemplary embodiments that will be described in more detail with reference to the accompanying drawings. It should be noted, however, that the inventive concepts are not limited to the following exemplary embodiments, and may be implemented in various forms.

In addition, in explanation of the present invention, the descriptions to the elements and functions of related arts may be omitted if they obscure the subjects of the present invention.

It will be also understood that although the terms first, second, third etc. may be used herein to describe various elements, these elements should not be limited by these terms. These terms are only used to distinguish one element from another element.

Hereinafter, a gas sensor member using a sensing material in which a one-dimensional porous metal oxide nanotube simultaneously having mesopores and macropores by the time difference between the decomposition of the sacrificial polymer and the diffusion of the metal oxide is functionalized with a protein-based highly dispersible nanoparticle catalyst, a gas sensor, and manufacturing methods thereof will be described in detail with reference to the accompanying drawings.

Embodiments of the inventive concept relate to a one-dimensional porous nanotube gas sensor member which contains a nanoparticle catalyst synthesized using an apoferritin and in which mesopores (0.1 nm to 50 nm) and macropores (50 nm to 300 nm) are formed on the metal oxide nanotube and the nanoparticle catalysts are uniformly distributed on the metal oxide nanotube at the same time by the decomposition of the polystyrene polymer and the crystallization and diffusion of the metal oxide which sequentially occur during the high-temperature heat treatment of the metal oxide precursor/polymer composite nanofiber containing spherical polystyrene colloids. In the case of the study on the existing gas sensor using a metal oxide, studies for improving the sensing characteristics have been carried out in which a structure that can react with a large amount of gas is created by increasing the specific surface area in order to improve the sensing characteristics of the metal oxide sensing material, and also studies have been carried out in which the catalytic reaction is promoted by loading a metal or metal oxide catalyst on the sensing material. In other words, it can be seen that the shape and catalytic activity of the sensing material are two important factors for improving the sensing characteristics. However, the studies that have been carried out so far have a disadvantage that the process to increase the specific surface area and the process to load the catalyst on the sensing material are separately required and the respective processes are fairly complicated. Specifically, the process to uniformly synthesize nanoparticle catalysts having a size of several nm requires various pre-treatment processes, in the case of synthesizing a metal oxide nanotube or a metal oxide nanotube having pores, there is a disadvantage that the process is relatively complicated and requires a long time and a high cost. In order to overcome these disadvantages and to design an optimum sensing material, in the inventive concept, a nanoparticle catalyst having a uniform size distribution of about from 1 nm to 3 nm is easily synthesized using an apoferritin of a protein template, the nanoparticle catalyst is mixed into a metal oxide precursor/polymer mixed electrospinning solution together with spherical polystyrene colloids having a wide size distribution of from 200 nm to 1000 nm, and the nanoparticle catalyst and the spherical polystyrene sacrificial template are uniformly loaded on the surface and in the inside of the metal oxide precursor/polymer composite nanofiber. Moreover, as mesopores (0.1 nm to 50 nm) and macropores (50 nm to 300 nm) are formed and a one-dimensional porous metal oxide nanotube structure on which the nanoparticle catalysts are uniformly loaded is formed using the decomposition of the sacrificial polymer and the crystallization and diffusion of the metal oxide which sequentially occur during the high-temperature heat treatment of the synthesized composite nanofiber, it is possible to easily synthesize a one-dimensional porous nanotube sensing material which has a large specific surface area and a double pore distribution and on which the nanoparticle catalyst is uniformly loaded without aggregation to exhibit maximized catalytic activity in a large scale by a single process. Here, the mesopores having a size range of from 0.1 nm to 50 nm and the macropores in a range of frim 50 nm to 300 nm which are formed on the inner and outer walls of the nanotube not only increase the surface area of the nanotube but also maximize the gas flow toward the sensing material. In particular, in order to effectively detect VOCs gases, the mesopores having a size range of from 0.1 nm to 50 nm plays an important role, the sensing material thus developed has the number of mesopores (0.1 nm to 50 nm) to be several times as many as that of the macropores (50 nm to 300 nm) so as to have an excellent condition as a sensing material. In addition to this, the nanoparticle catalysts that are uniformly distributed on the inner/outer surface of the nanotube and the surface exposed to the pores without being aggregated with one another can maximize the catalytic effect exhibited when a gas reacts with the sensing material in a small amount. The synergistic effect between the morphological concept of the nanotube structure including a number of pores and the catalytic activity concept of being uniform distributed without aggregation can be expected, and thus it is possible to fabricate a highly sensitive sensing material for a gas sensor as compared to the existing sensing material. In particular, although a sacrificial polymer template having a size of several hundred nanometers (nm) is used, it is possible to form mesopores having a size range of from 0.1 nm to 50 nm and macropores having a size of from 50 nm to 300 nm on the nanotube surface. In order to fabricate a gas sensor member having the features as described above, a gas sensor member, a gas sensor, and manufacturing methods thereof are implemented by an efficient and easy process.

FIG. 1 is a schematic diagram of a gas sensor member using a one-dimensional porous metal oxide nanotube 100 including a nanoparticle catalyst 110 and a plurality of mesopores 121 and macropores 131 according to Embodiment Example 2 of the inventive concept. An electrospinning solution prepared by adding a nanoparticle catalyst embedded inside the hollow structure of the apoferritin and a spherical sacrificial template colloid to a metal oxide precursor/polymer mixed electrospinning solution, and a metal oxide precursor/polymer composite nanofiber on which the spherical sacrificial template and the nanoparticle catalyst encapsulated in the apoferritin are uniformly loaded synthesized by electrospinning the electrospinning solution.

The composite nanofiber thus formed is subjected to a high-temperature heat treatment, the sacrificial templates and the apoferritin protein shell are removed to form mesopores having a size range of from 0.1 nm to 50 nm and macropores having a size of from 50 nm to 300 nm, the metal oxide particles gather on the fiber surface so as to form mesopores as the macropores are filled by the metal oxide particles, and the nanoparticle catalysts also gather on the surface so as to be uniformly loaded in the inside and on the outside of the tube structure, whereby a one-dimensional porous nanotube having mesopores and macropores can be formed.

Here, the metal that can be synthesized inside the hollow structure of the apoferritin is not particularly limited as long as it is in an ionic form. Specific examples thereof may include copper(II) nitrate, copper(II) chloride, cobalt(II) nitrate, cobalt(II) acetate, lanthanum(III) nitrate, lanthanum (III) acetate, platinum(IV) chloride, platinum(II) acetate, gold(I, III) chloride, gold(III) acetate, silver chloride, silver acetate, iron(III) chloride, iron(III) acetate, nickel(II) chloride, nickel(II) acetate, ruthenium(III) chloride, ruthenium acetate, iridium(III) chloride, iridium acetate, tantalum(V) chloride, and palladium(II) chloride, and it is possible to synthesize a nanoparticle catalyst composed of one or two or more of the particles selected from Pt, Pd, Rh, Ru, Ni, Co, Cr, Ir, Au, Ag, Zn, W, Sn, Sr, In, Pb, Fe, Cu, V, Ta, Sb, Sc, Ti, Mn, Ga, or Ge in an alloy form using these precursors. It is possible to use one heterogeneous nanoparticle catalyst selected form the group consisting of a metal-metal, a metal-metal oxide, or a metal oxide-metal oxide as the alloy nanoparticle catalyst. Examples of the representative metal-metal oxide nanoparticle catalyst may include $Pt/IrO_2$, $Pt/RuO_2$, $Pt/Rh_2O_3$, $Pt/NiO$, $Pt/Co_3O_4$, $Pt/CuO$, $Pt/Ag_2O$, $Pt/Fe_2O_3$, $Au/IrO_2$, $Au/RuO_2$, $Au/Rh_2O_3$, $Au/NiO$, $Au/Co_3O_4$, $Au/CuO$, and $Au/Ag_2O$, examples of the metal-metal nanoparticle catalyst may include Pt—Au, and the metal oxide-metal oxide catalyst may be a metal oxide-metal oxide catalyst composed of two kinds selected from $TiO_2$, $ZnO$, $WO_3$, $SnO_2$, $IrO_2$, $In_2O_3$, $V_2O_3$, and $MoO_3$ of n-type metal oxides and $Ag_2O$, $PdO$, $RuO_2$, $Rh_2O_3$, $NiO$, $Co_3O_4$, $CuO$, $Fe_2O_3$, $Fe_3O_4$, $V_2O_5$, and $Cr_2O_3$ of p-type metal oxides. Hence, in the case of synthesizing a nanoparticle catalyst using the apoferritin template having a hollow structure, it is possible not only to synthesize the nanoparticle catalyst having a constant size distribution but also to control the size of the nanoparticle catalyst by controlling the amount of the metal precursor. In addition, the nanoparticle catalysts are encapsulated in the protein shell, apoferritin, and the apoferritin surface is positively charged at a pH of from 7 to 8.5 so as to have an advantage of being favorably dispersed in the electrospinning solution without being aggregated with one another. From the viewpoint of the role of nanoparticle catalyst acting in the gas sensing material, there are a nanoparticle catalyst of a noble metal, such as platinum (Pt) or gold (Au), which exhibits a chemical sensitization effect that the concentration of adsorbed oxygen ions which involve in the surface reaction is increased by promoting the decomposition reaction of oxygen molecule in between the surface of the metal oxide and the air layer and a nanoparticle catalyst which exhibits an electronic sensitization effect that a catalytic reaction is caused by the oxidation, such as $PdO$, $Co_3O_4$, $NiO$, $Cr_2O_3$, $CuO$, $Fe_2O_3$, $Fe_3O_4$, $TiO_2$, $ZnO$, $SnO_2$, $V_2O_5$, or $V_2O_3$, which affects the improvement in sensing characteristics.

The spherical polymer sacrificial template used for the synthesis of the one-dimensional porous metal oxide having a double pore distribution described above refers to a template that can be removed during the high-temperature heat treatment, and the kind of the template is not particularly limited. Specifically, it may be one kind or a mixture of two or more kinds selected from polymethyl methacrylate (PMMA), polyvinylpyrrolidone (PVP), polyvinyl acetate (PVAc), polyvinyl alcohol (PVA), polystyrene (PS), polyacrylonitrile (PAN), polyvinylidene fluoride (PVDF), polyacrylic acid (PAA), polydiallydimethylammonium chloride (PDADMAC), or polystyrene sulfonate (PSS). In addition, the sacrificial template has a size in the range of from 50 nm to 1 µm, the sacrificial template is preferably dispersed without being decomposed when mixed with the electrospinning solution, and a polymer colloid that is insoluble in a solvent since a charged ion or a charged anionic or cationic surfactant is formed on the surface of the colloid may be used as the sacrificial template although the sacrificial colloid is a polymer soluble in the solvent.

It is possible to manufacture a metal oxide precursor/polymer composite nanofiber which has a rugged structure and in which the sacrificial template and the nanoparticle catalyst in the hollow structure of the apoferritin are uniformly distributed by dispersing the nanoparticle catalyst synthesized using the apoferritin described above and the spherical sacrificial template in the electrospinning solution and using the electrospinning method. Mesopores and macropores are formed using the decomposition of the sacrificial polymer and the crystallization and diffusion of the metal oxide which sequentially occur during the high-temperature heat treatment of the composite nanofiber thus formed, and a one-dimensional porous nanotube on which the nanoparticle catalysts are uniformly loaded can be synthesized through the diffusion of the nanoparticle catalyst occurring at the time of tube formation. In the case of the one-dimensional porous nanotube which have mesopores and macropores and contains the nanoparticle catalyst, the diameter of the nanotube structure is in a diameter range of from 50 nm to 5 µm (the outer diameter may be in a size range of from 50 nm to 2 µm, and the inner diameter may be in a size range of from 40 nm to 1.95 µm), the thickness between the inner wall and the outer wall (thickness of the shell) is in a range of from 10 nm to 50 nm, and the length is in a range of from 1µ to 100 µm.

The one-dimensional porous nanotube which constitutes the nano-structure and has a metal oxide semiconductor double pore distribution is not particularly limited to a specific material as long as the value of the electrical resistance and the electrical conductivity is changed by the adsorption and desorption of gas. Specifically, the one-dimensional porous nanotube may be a one-dimensional porous nanotube which has a double pore distribution and is composed of one or a composite material of two or more selected from $ZnO$, $SnO_2$, $WO_3$, $Fe_2O_3$, $Fe_3O_4$, $NiO$, $TiO_2$, $CuO$, $In_2O_3$, $Zn_2SnO_4$, $Co_3O_4$, $PdO$, $LaCoO_3$, $NiCo_2O_4$, $Ca_2Mn_3O_8$, $V_2O_5$, $Cr_2O_3$, $Nd_2O_3$, $Sm_2O_3$, $Eu_2O_3$, $Gd_2O_3$, $Tb_4O_7$, $Dy_2O_3$, $Ho_2O_3$, $Er_2O_3$, $Yb_2O_3$, $Lu_2O_3$, $Ag_2V_4O_{11}$, $Ag_2O$, $Li_{0.3}La_{0.57}TiO_3$, $LiV_3O_8$, $InTaO_4$, $CaCu_3Ti_4O_{12}$, $Ag_3PO_4$, $BaTiO_3$, $NiTiO_3$, $SrTiO_3$, $Sr_2Nb_2O_7$, $Sr_2Ta_2O_7$, or $Ba_{0.5}Sr_{0.5}Co_{0.8}Fe_{0.2}O_{3-7}$.

By using a gas sensor member suing the one-dimensional porous metal oxide nanotube 100 which is fabricated above, contains the nanoparticle catalyst 110, and has the mesopores 121, macropores 131, and with a double pore distribution, it is possible to manufacture an ultrasensitive/highly selective sensor which can diagnose a human body disease at the early stage by selectively sensing a specific biomarker gas which acts as a biomarker in the exhaled breath of a human body and can also be applied to an environmental sensor capable of monitoring harmful environmental gases in real time. In particular, an optimal structure in which the sensing materials in all areas can effectively response to the gas is formed by forming pores on the nanotube surface to maximize the gas flow toward the sensing material. In addition, the porous tube structure thus fabricated has a thin surface and an increased surface area so as to have a great advantage of being able to maximize the sensing characteristics of the sensing material with a small amount of catalyst and an advantage of being able to manufacture various kinds of gas sensor members not only easily and rapidly but also in a large scale.

Figure 2:
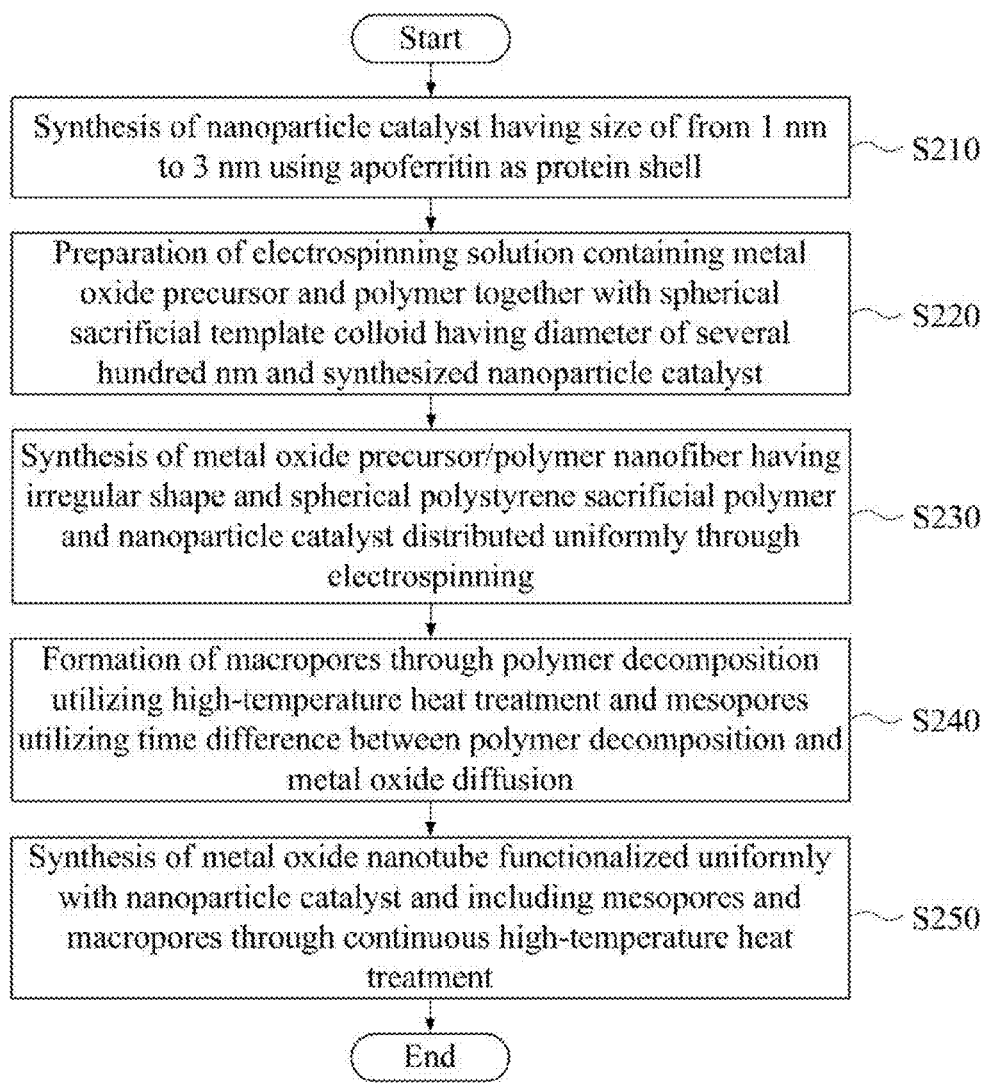
FIG. 2 is a flow chart of a method of manufacturing a gas sensor using a one-dimensional porous metal oxide nanotube structure which contains a nanoparticle catalyst synthesized using an apoferritin and includes a plurality of circular or elliptical mesopores and macropores according to an embodiment of the inventive concept.

FIG. 2 is a flow chart of a method of manufacturing a gas sensor member using a one-dimensional porous metal oxide semiconductor nanotube which is synthesized using the electrospinning method, contains a nanoparticle catalyst, and has a double pore distribution including a number of pores according to an embodiment of the inventive concept. According to the flow chart in FIG. 2, the method for manufacturing a gas sensor member includes a step S210 of synthesizing a nanoparticle catalyst using an apoferritin having a hollow structure, a step S220 of preparing an electrospinning solution by mixing the nanoparticle catalyst thus synthesized and the spherical sacrificial template with a metal oxide precursor/polymer electrospinning solution and stirring them together, a step S230 of synthesizing a metal oxide precursor/polymer composite nanofiber in which the spherical sacrificial template and the nanoparticle catalyst are uniformly distributed through electrospinning, a step S240 of forming macropores (50 nm to 300 nm) through the decomposition of the spherical polymer sacrificial template by a high-temperature heat treatment and mesopores (0.1 nm to 50 nm) utilizing the polymer decomposition and the metal oxide diffusion which sequentially occur, and a step S250 of synthesizing a metal oxide nanotube that is uniformly functionalized with the nanoparticle catalyst and has mesopores and macropores through the continuous high-temperature heat treatment. The respective steps will be described below in more detail.

First, the step S210 of synthesizing a nanoparticle catalyst using an apoferritin is described. The apoferritin used in this step S210 includes ferritin extracted from equine spleen, and an apoferritin prepared by removing the iron ion present inside a ferritin obtained from liver, spleen, or the like of a human body or a swine regardless of the extraction site may be used. For storage of the apoferritin, solutions of sodium chloride (NaCl) at various concentrations including saline can be used as a solution to keep the apoferritin, and the apoferritin is required to be stored under refrigeration at 4° C. or lower. In addition, in order to embed the metal salt in the apoferritin, a an acidic solution having a pH of from 2 to 3 or a basic solution having a pH in a range of from 7.5 to 8.5 (or in a pH range of from 7.5 to 9) is preferable, the apoferritin is immersed in a solution containing a metal salt dissolved therein for about from 1 hour to 24 hour so that the metal salt can be sufficiently diffused into the apoferritin. The concentration of the solution for storage, such as saline containing the apoferritin is set to be in a range of from 0.1 to 200 mg/ml. As the solvent used when preparing the metal salt solution, a commercially available solvent such as ethanol, water, chloroform, N,N'-dimethylformamide, dimethylsulfoxide, N,N'-dimethylacetamide, or N-methylpyrrolidone can be used, and the solvent is not limited to a particular solvent as long as it dissolves a metal salt. Examples of the nanoparticle catalyst embedded in the apoferritin may include Pt, Pd, Rh, Ru, Ni, Co, Cr, Ir, Au, Ag, Zn, W, Sn, Sr, In, Pb, Fe, Cu, V, Ta, Sb, Sc, Ti, Mn, Ga, or Ge, the nanoparticle catalyst composed of one or two or more of these may be synthesized in an alloy form. It is possible to use one heterogeneous nanoparticle catalyst selected form the group consisting of a metal-metal, a metal-metal oxide, or a metal oxide-metal oxide as the alloy nanoparticle catalyst. Examples of the representative metal-metal oxide nanoparticle catalyst may include $Pt/IrO_2$, $Pt/RuO_2$, $Pt/Rh_2O_3$, $Pt/NiO$, $Pt/Co_3O_4$, $Pt/CuO$, $Pt/Ag_2O$, $Pt/Fe_2O_3$, $Au/IrO_2$, $Au/RuO_2$, $Au/Rh_2O_3$, $Au/NiO$, $Au/Co_3O_4$, $Au/CuO$, and $Au/Ag_2O$, examples of the metal-metal nanoparticle catalyst may include Pt—Au, and the metal oxide-metal oxide catalyst may be a metal oxide-metal oxide catalyst composed of two kinds selected from $TiO_2$, $ZnO$, $WO_3$, $SnO_2$, $IrO_2$, $In_2O_3$, $V_2O_3$, and $MoO_3$ of n-type metal oxides and $Ag_2O$, $PdO$, $RuO_2$, $Rh_2O_3$, $NiO$, $Co_3O_4$, $CuO$, $Fe_2O_3$, $Fe_3O_4$, $V_2O_5$, and $Cr_2O_3$ of p-type metal oxides. As the reducing agent to reduce the metal salt contained inside the hollow structure of the apoferritin, a generally used reducing agent such as sodium borohydride ($NaBH_4$), formic acid (HCOOH), oxalic acid ($C_2H_2O_4$) or lithium aluminum hydride ($LAlH_4$) may be used, and a reducing agent capable of reducing the metal salt so as to form a metallic nanoparticle catalyst may be used without any particular limitation. The solution subjected to the reduction of the metal salt inside the apoferritin by a reducing agent is then subjected to the centrifugation to separate the apoferritin protein embedding the nanoparticle catalyst therefrom, and the rotational speed of the centrifugal separator used at this time is preferably from 10,000 rpm to 13,000 rpm.

Next, the step S220 of preparing a metal oxide precursor/polymer mixed electrospinning solution which contains the nanoparticle catalyst that is synthesized and embedded inside the hollow structure of the apoferritin and a spherical sacrificial template is described. In this step S220, the nanoparticle catalyst that is synthesized and embedded inside the hollow structure of the apoferritin and sacrificial template colloids are added to a metal oxide precursor/polymer mixed electrospinning solution, and the mixture stirred such that the nanoparticle catalyst and the sacrificial template colloids are uniformly dispersed in the electrospinning solution, whereby the mixed electrospinning solution is prepared. As the solvent used when preparing the electrospinning solution, a commercially available solvent such as N,N'-dimethylformamide, dimethylsulfoxide, N,N'-dimethylacetamide, N-methylpyrrolidone, deionized (DI) water, or ethanol may be used, but it is required to select a solvent which can dissolve the metal oxide precursor and the polymer at the same time. In addition, the polymer and the sacrificial template used herein are not limited to specific substances as long as they are a substance that is removed through the high-temperature heat treatment, and representative examples thereof may include polymethyl methacrylate (PMMA), polyvinylpyrrolidone (PVP), polyvinyl acetate (PVAc), polyvinyl alcohol (PVA), polyacrylonitrile (PAN), polyethylene oxide (PEO), polypropylene oxide (PPO), polyethylene oxide copolymer, polypropylene oxide copolymer, polycarbonate (PC), polyvinylchloride (PVC), polycaprolactone, and polyvinylidene fluoride.

In addition, the metal oxide precursor used in this step is required to be dissolved in a solvent, the metal oxide precursor is not limited to a specific metal salt as long as it is a precursor containing a metal salt capable of forming a metal oxide semiconductor nanofiber or nanotube which exhibits a change in resistance by the adsorption and desorption of gas through the high-temperature heat treatment, such as $SnO_2$, $WO_3$, $CuO$, $NiO$, $ZnO$, $Zn_2SnO_4$, $Co_3O_4$, $Cr_2O_3$, $LaCoO_3$, $V_2O_5$, $IrO_2$, $TiO_2$, $Er_2O_3$, $Tb_2O_3$, $Lu_2O_3$, $Ag_2O$, $SrTiO_3$, $Sr_2Ta_2O_7$, $BaTiO_3$, or $Ba_{0.5}Sr_{0.5}Co_{0.8}Fe_{0.2}O_{3-7}$.

The weight ratio of the polymer to the metal oxide precursor for forming the electrospinning solution is preferably about from 1:1 to 2, and the ratio to the polymer to the nanoparticle catalyst synthesized using the apoferritin is preferably about from 1:0.00001 to 0.1 and may be in a range of from 0.000001 to 1. In addition, the weight ratio of the spherical sacrificial template to the polymer used in the step S220 is preferably about from 1:1 to 2 and may be in a range of from 0 wt % to 50 wt %. In addition, the weight ratio of the metallic nanoparticle catalyst encapsulated in the protein may be in a range of from 0.001 wt % to 50 wt % with respect to the metal oxide precursor constituting the metal oxide precursor/polymer composite nanofiber. The size of the spherical sacrifice template having a size in a range of from 50 nm to 1 μm is preferably set in consideration of the size of the pores to be formed, and the kind of the metal salt in the apoferritin is selected in consideration of the selectivity of the gas to be sensed, whereby it is possible to manufacture a gas sensor member having various characteristics As the procedure to prepare a mixed electrospinning solution in the step S220, the metal oxide precursor is first dissolved in a solvent, and the apoferritin encapsulating the nanoparticle catalyst synthesized in advance and the spherical sacrificial template are sequentially dispersed in the solution. Here, as the dispersing method, there is a method to stir for 1 hour or longer at a rotational speed of 500 rpm. In order to impart a viscosity to the solution thus prepared to a certain extent to which the electrospinning is facilitated, a polymer is added to the solution at an appropriate ratio and the mixture is sufficiently stirred until the polymer is completely dissolved in the solution. As the stirring condition, the mixture is preferably stirred at from room temperature to 50° C., and it is sufficiently stirred for from 5 hours to about 48 hours so that the apoferritin encapsulating the nanoparticle catalyst and the sacrificial template colloids are uniformly mixed in the metal oxide precursor and polymer solution.

The step S230 is carried out by electrospinning the electrospinning mixed solution prepared above to form a rugged metal oxide precursor/polymer composite nanofiber in which the spherical sacrificial template and the nanoparticle catalyst in the apoferritin are uniformly distributed.

Upon conducting the electrospinning in order to carry out the step S230, the metal oxide precursor/polymer mixed electrospinning solution containing the nanoparticle catalyst and the spherical sacrificial template thus prepared is filled in a syringe, the syringe is pressed using the syringe pump at a constant rate so that a certain amount of the electrospinning solution is discharged therefrom. The electrospinning system may be constituted by a high voltage apparatus, a grounded conductive substrate, a syringe, and a syringe nozzle, a high voltage about from 5 kV to 30 kV is applied to between the solution filled in the syringe and the conductive substrate to generate the electric field, and the electrospinning solution discharged through the syringe nozzle is ejected in a long nanofiber form due to the electric field thus generated, whereby the electrospinning is conducted. The electrospinning solution ejected in a long nanofiber form is obtained as a solid polymer fiber as the solvent contained in the electrospinning solution is evaporated and volatilized and a composite fiber containing the metal oxide precursor, the nanoparticle catalyst encapsulated in the apoferritin, and the spherical sacrificial template is obtained at the same time. The discharge speed may be controlled to from 0.01 ml/min to 0.5 ml/min, and it is possible to fabricate a metal oxide precursor/polymer/nanoparticle catalyst composite nanofiber having a desired diameter and a rugged structure by controlling the voltage and the discharge rate.

Through the step S240, it is possible to form a metal oxide nanotube structure through the high-temperature heat treatment of the composite nanofiber thus fabricated and to manufacture a one-dimensional porous metal oxide nanotube in which mesopores and macropores are distributed on the surface of the metal oxide nanotube and the nanoparticle catalysts are uniformly distributed on such a nanotube structure at the same time. Through the high-temperature heat treatment in a temperature range of from 500 to 800° C., the spherical polymer substance used as the sacrificial template and the apoferritin are all removed to form macropores (50 nm to 300 nm) and mesopores (0.1 nm to 50 nm), and the macropores are partially filled by the crystallization and diffusion of the metal oxide taking place after the decomposition of the polymer to form a plurality of mesopores (0.1 nm to 50 nm) on the nanotube surface.

Additionally, through the step S250, the nanoparticle catalyst encapsulated in the apoferritin is uniformly loaded on the inner and outer walls and in the inside of the porous nanotube during the heat treatment as the apoferritin is removed. The structure that is finally formed through the step S250 is a one-dimensional porous metal oxide nanotube structure which has a plurality of mesopores and macropores and in which the nanoparticle catalyst is uniformly loaded on the inner and outer walls and in the inside of the tube.

Figure 3:
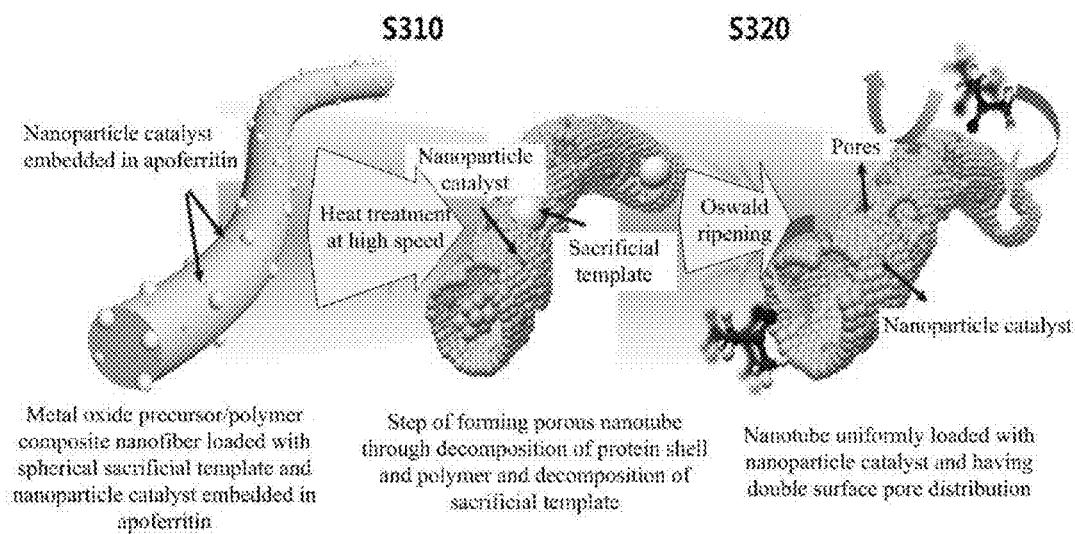
FIG. 3 is a diagram illustrating a process of manufacturing a one-dimensional porous metal oxide nanotube structure which contains a nanoparticle catalyst, includes a plurality of circular or elliptical pores, and has a double pore distribution using an electrospinning method according to an embodiment of the inventive concept.

FIG. 3 is a diagram schematically illustrating the manufacturing process according to the method for manufacturing a gas sensor member using a one-dimensional porous metal oxide nanotube which is fabricated using an electrospinning method, contains a nanoparticle catalyst, and has a double pore distribution according to an embodiment of the inventive concept.

The step S310 of the first step is a process showing the intermediate step of the high-temperature heat treatment of the metal oxide precursor/polymer composite nanofiber on which the spherical sacrificial template and the nanoparticle catalyst encapsulated in the apoferritin are uniformly loaded, and it is a step showing the intermediate step in which pores having various sizes are formed as the spherical sacrificial template and the apoferritin are removed and a metal oxide tube is formed through the Ostwald ripening at the same time.

In the step S320 of the second step, as the spherical sacrificial template, the apoferritin, and the polymer matrix in the composite fiber are all removed after the final high-temperature heat treatment, the crystallization and diffusion of the metal oxide occurs, and finally, there are a number of mesoporous and macropores on the inner and outer walls of the nanotube, and the nanoparticle catalysts are diffused so that a one-dimensional porous metal oxide nanotube which has a double pore distribution and in which the nanoparticle catalysts are uniformly loaded on the outer surface and in the inside of the nanotube is synthesized.

Figure 4:
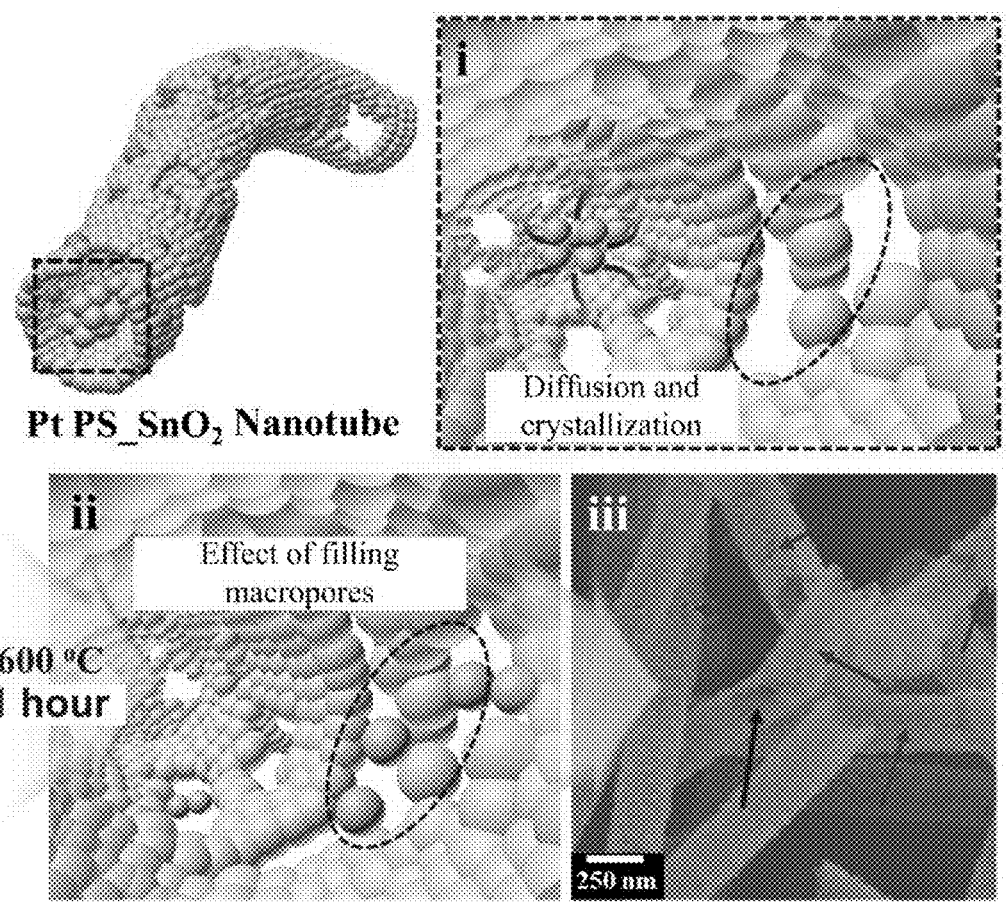
FIG. 4 is a diagram illustrating a principle that mesopores are formed on the nanotube surface by the spherical sacrificial template and the crystallization and diffusion of the metal oxide according to an embodiment of the inventive concept.

FIG. 4 is a diagram illustrating the mechanism that a plurality of mesopores and macropores are formed on the nanotube surface during the high-temperature heat treatment. Specifically, the macropores are formed as the sacrificial polystyrene template is decomposed during the high-temperature heat treatment and the mesopores are then formed as the macropores are filled by the crystallization and diffusion of the metal oxide.

Figure 5:
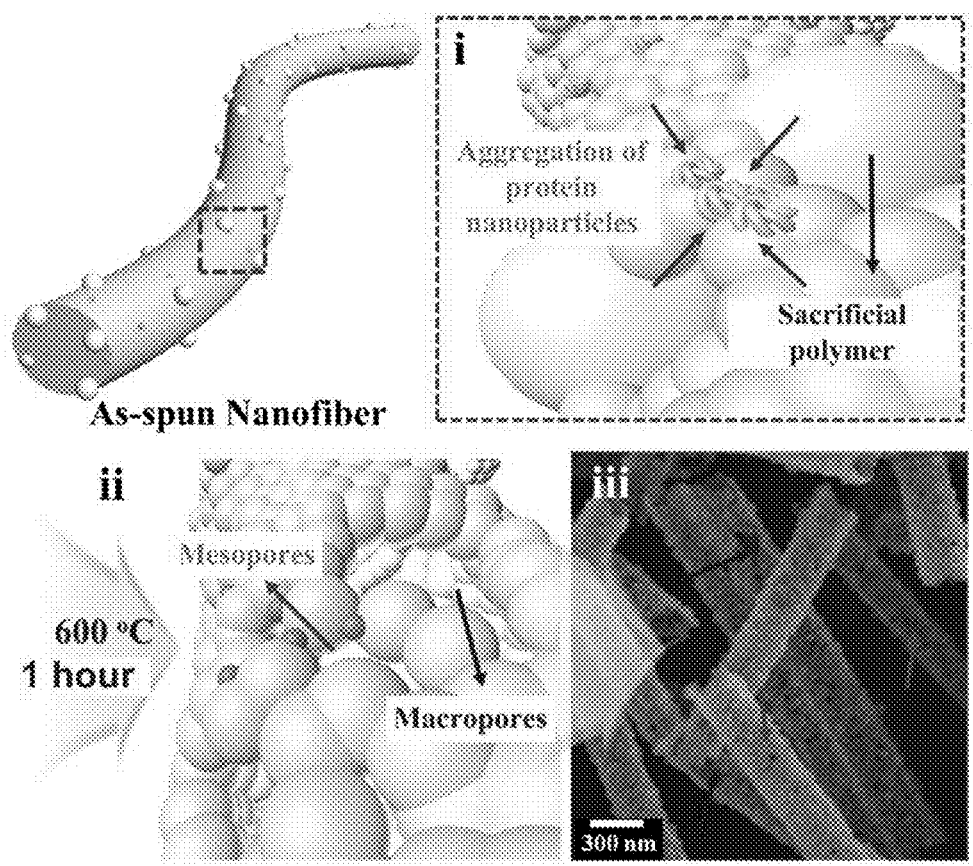
FIG. 5 is a diagram illustrating a principle that mesopores are formed by a protein having hollow structure according to an embodiment of the inventive concept.

FIG. 5 is a diagram illustrating the procedure that the protein templates in a 12 nm size are densely gathered in between the polystyrene templates distributed on the nanofibers and the densely gathered protein templates are decomposed during the high-temperature heat treatment to contribute to the formation of the mesopores. Here, the highly dispersible protein templates can be densely gathered in a narrow space in between the polystyrene templates.

As described above, in the method for manufacturing a gas sensor member using a one-dimensional porous metal oxide nanotube which is fabricated using a sacrificial template, an electrospinning method, and the time difference between the decomposition of a polymer and the diffusion of a metal oxide, contains a nanoparticle catalyst, and have a number of mesopores and macropores according to embodiments of the inventive concept, it is possible to improve the gas sensing effect by forming a one-dimensional nanotube structure having a large surface area required for the reaction with a gas and forming pores at the same time to maximize the gas flow toward the sensing material and to greatly improve the reaction rate characteristic of the gas sensor, the sensitivity characteristics, and the selectivity by loading a catalyst which is uniformly distributed using the characteristics of a protein and has a chemical/electronic sensitization effect unlike the existing catalyst.

Hereinafter, the inventive concept will be described in detail with reference to Embodiment Examples and Comparative Examples. Embodiment Examples and Comparative Examples are only for explaining the inventive concept, and the inventive concept is not limited to the following Embodiment Examples.

Embodiment Example 1: Preparation of Pt Nanoparticle Catalyst Using Apoferritin as Template The following procedure is used in order to synthesize a Pt nanoparticle catalyst of 3 nm or less inside an apoferritin having a hollow structure.

The apoferritin solution (Sigma Aldrich) is dispersed in a 0.15 M NaCl aqueous solution at a concentration of 35 mg/ml. A basic solution such as NaOH is added to the apoferritin solution as described above to adjust the pH to about 8.5, thereby preparing an optimum condition for the diffusion of Pt metal ion diffuse into the apoferritin. The basic solution used herein is not limited as long as it is a basic aqueous solution in addition to NaOH. The precursor of Pt metal ion that is encapsulated in the apoferritin is $H_2PtCl_6 \cdot H_2O$, and it is prepared in the form of an aqueous solution by dissolving 16 mg of $H_2PtCl_6 \cdot H_2O$ in 1 g of DI water. The aqueous solution of metal salt precursor thus prepared is gradually dropped into the apoferritin solution having an adjusted pH drop by drop using a dropper and mixed. The mixed solution is stirred for 1 hour so that the Pt metal ions diffuse into the inside of the apoferritin having a hollow structure. The stirring conditions described above means that the stirring is conducted at room temperature and a rotational speed of 100 rpm for 1 hour. After the mixed solution is sufficiently stirred, the metal ions in the apoferritin are reduced using a reducing agent so as to synthesize a Pt nanoparticle catalyst in the inside of the apoferritin. As the reducing agent used herein, a $NaBH_4$ aqueous solution is representative. The reducing agent, $NaBH_4$ used at this time is prepared in the form of an aqueous solution at a concentration of 40 mM and added by 0.5 ml.

The aqueous solution in which the Pt nanoparticle catalyst that is encapsulated in the hollow structure of the apoferritin and synthesized by the method as described above is dispersed contains the reducing agent and the ligand of the metal salt, and thus the synthesized Pt nanoparticle catalyst is required to be extracted through centrifugation. At this time, as the centrifugal condition, it is preferable to conduct the centrifugation at about 12,000 rpm for 10 minutes or longer. The Pt nanoparticle catalyst encapsulated in the apoferritin extracted by centrifugation is dispersed in DI water, thereby preparing an aqueous solution in which the Pt nanoparticle catalyst is dispersed in the inside of the apoferritin.

Figure 7:
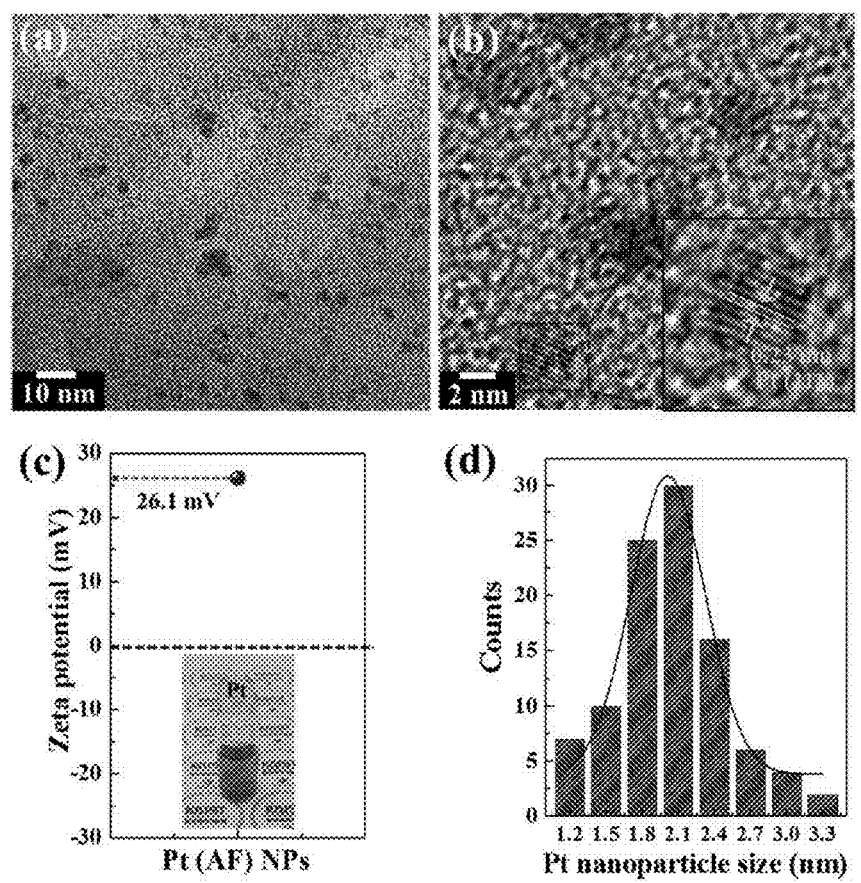
FIGS. 7(a) and 7(b) are transmission electron microscope (TEM) images of apoferritin particles encapsulating a Pt nanoparticle catalyst according to Embodiment Example 1 of the inventive concept.
FIG. 7(c) illustrates zeta potential data to analyze the surface charge of the particles.
FIG. 7(d) illustrates the size distribution of Pt nanoparticle catalysts, respectively.

FIGS. 7(a) and 7(b) are transmission electron microscope (TEM) images of the apoferritin encapsulating the Pt nanoparticle catalyst synthesized by the procedure described above, FIG. 7(c) illustrates the surface charge, and FIG. 7(d) illustrates the size distribution. From the images taken using a transmission electron microscope, it can be seen that the Pt nanoparticle catalyst is favorably dispersed, and this is due to the dispersion effect caused by the repulsive force between the positively (+) charged protein shells. In addition, the nanoparticle catalyst has a size distribution in from 1 to 3 nm.

Figure 6:
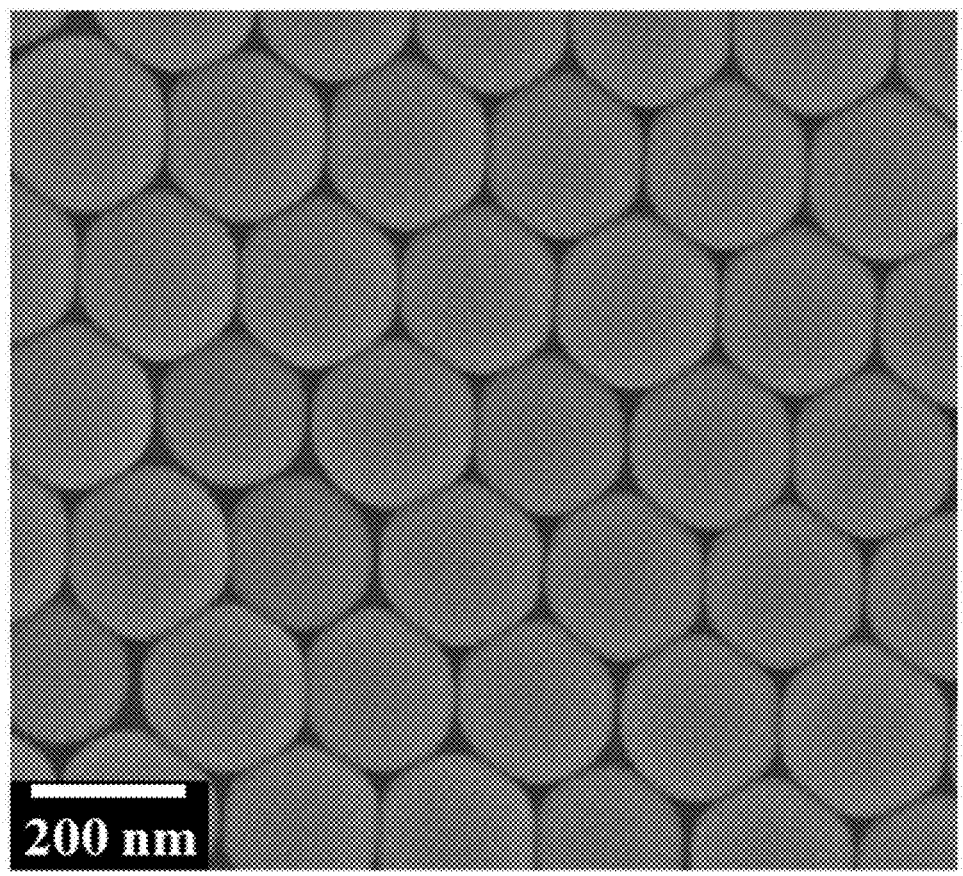
FIG. 6 is a scanning electron microscope (SEM) image of a spherical polymer sacrificial template which plays a role of the sacrificial template according to an embodiment of the inventive concept.

Embodiment Example 2: Fabrication of One-Dimensional Porous Tin Oxide ($SnO_2$) Nanotube 100 Structure Having Pt Nanoparticle Catalyst Uniformly Loaded on Inner and Outer Walls of Tube an Having Mesopores and Macropores First, 0.25 g of tin chloride dihydrate of the metal oxide precursor is added to a mixed solvent of 1.35 g of DMF and 1.35 g of ethanol and dissolved at room temperature. Next, 0.3 g of spherical polystyrene (diameter: 200 nm) colloids to serve as the sacrificial template as illustrated in FIG. 6 is added to and sufficiently dispersed in the solution in which the metal salt precursor is dissolved. The polystyrene colloids used in Embodiment Example 2 have an anionic surfactant formed on the surface, and thus it exhibits excellent dispersibility, is insoluble in DMF of the solvent, and is removed during the heat treatment to be conducted later to contribute to the formation of macropores. In Embodiment Example 2, polystyrene polymer beads having a size of 200 nm are used as the colloidal template, but the kind of the polymer template is not particularly limited. Specifically, it may be one kind or a mixture of two or more kinds selected from polymethyl methacrylate (PMMA), polyvinylpyrrolidone (PVP), polyvinyl acetate (PVAc), polyvinyl alcohol (PVA), polystyrene (PS), polyacrylonitrile (PAN), polyvinylidene fluoride (PVDF), polyacrylic acid (PAA), polydiallyldimethylammonium chloride (PDADMAC), or polystyrene sulfonate (PSS). In addition, the sacrificial template has a size in the range of from 50 nm to 1 μm, it is dispersed without being decomposed when mixed with an electrospinning solution, and a polymer colloid that is insoluble in a solvent since a charged ion or a charged anionic or cationic surfactant is formed on the surface of the colloid may be used as the sacrificial template although the sacrificial colloid is a polymer soluble in the solvent. The dispersion condition of the colloidal polystyrene template means that the stirring is conducted at a rotational speed of 500 rpm for about 10 minutes, and the diameter of the polystyrene used in the above is not limited to 200 nm a colloidal solution of polystyrene having various diameters may be used. In addition, 200 mg of the aqueous solution of the Pt nanoparticle catalyst synthesized in Embodiment Example 1 is added to the mixed solution (polystyrene colloid+metal salt+mixed solvent) and mixed. In order to increase the viscosity of the solution in which spherical polystyrene polymer and the nanoparticle catalyst encapsulated in the apoferritin are uniformly mixed thus synthesized, 0.35 g of polyvinylpyrrolidone (PVP) polymer having a molecular weight of 1,300,000 g/mol is added thereto, and the mixture is stirred at room temperature and a rotational speed of 500 rpm for 24 hours to prepare an electrospinning solution. The electrospinning solution thus prepared is filled in the syringe (Henke-Sass Wolf, 10 mL NORM-JECT®), the syringe is connected to the syringe pump, the electrospinning solution is pushed out at a discharge speed of 0.1 ml/min, and voltage between the nozzle (needle, 25 gauge) used during electrospinning and the collector gathering the nanofibers is set to 14 kV, thereby conducting the electrospinning. At this time, stainless steel plate is used as the nanofiber collecting plate, and the distance between the nozzle and the collector is set to 26 cm.

Figure 8:
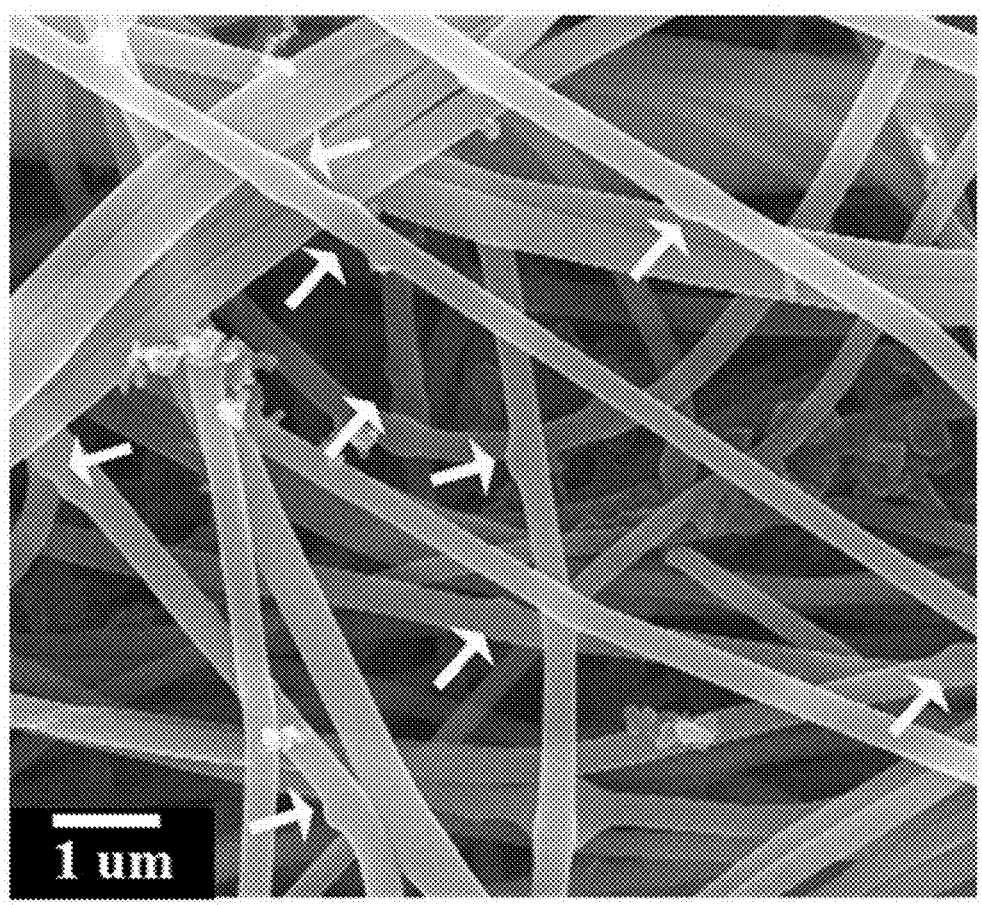
FIG. 8 is a SEM image of a nanofiber obtained by electrospinning a metal oxide precursor/polyvinylpyrrolidone (PVP) composite electrospinning solution containing an apoferritin protein which contains a Pt nanoparticle catalyst and has a hollow structure and a spherical polymer sacrificial template according to an embodiment of the inventive concept.

FIG. 8 is a scanning electron microscope (SEM) image of the nanofiber which is obtained by electrospinning and contains the metal oxide precursor, polyvinylpyrrolidone polymer, the spherical polystyrene sacrificial template, and the Pt nanoparticle catalyst encapsulated in the hollow structure of the apoferritin. It can be seen that a one-dimensional nanofiber is formed, and it is confirmed that the nanofiber has a rugged structure since it contains spherical polystyrene. The diameter of the nanofiber thus synthesized has a value between 200 nm and 300 nm.

The nanofiber which is synthesized by the method as described above and contains the metal oxide precursor, polyvinylpyrrolidone polymer, the spherical polystyrene sacrificial template, and the Pt nanoparticle catalyst encapsulated in the hollow structure of the apoferritin is maintained at 600° C. for 1 hour and then cooled to room temperature at a cooling rate of 40° C./min. The heat treatment is conducted in an air atmosphere using the small electric furnace Vulcan 3-550 manufactured by Ney. The apoferritin protein encapsulating the nanoparticle catalyst and the polymer are all decomposed through the heat treatment. In addition, the heat treatment is conducted in the air atmosphere, thus the metal salt precursor on the nanofiber surface is first oxidized into metal oxide particles through the nucleation and particle growth, the metal salt precursor inside the nanofiber is also oxidized through the Ostwald ripening and diffused toward the nanofiber surface to form a nanotube, at the same time, the polystyrene template is removed by the heat treatment, and the macropores are partially filled by the diffusion of metal oxide to form the mesopores and macropores on the surface of the nanotube. In addition, the Pt nanoparticle catalyst also has a significantly small size so as to diffuse toward the nanotube surface together with the tin oxide particles and to be loaded on the inner and outer walls of the tin oxide nanotube. As a result, a one-dimensional porous nanotube structure in which a number of pores are distributed on the surface of the tin oxide nanotube structure and the Pt nanoparticle catalysts are uniformly distributed.

Figure 9:
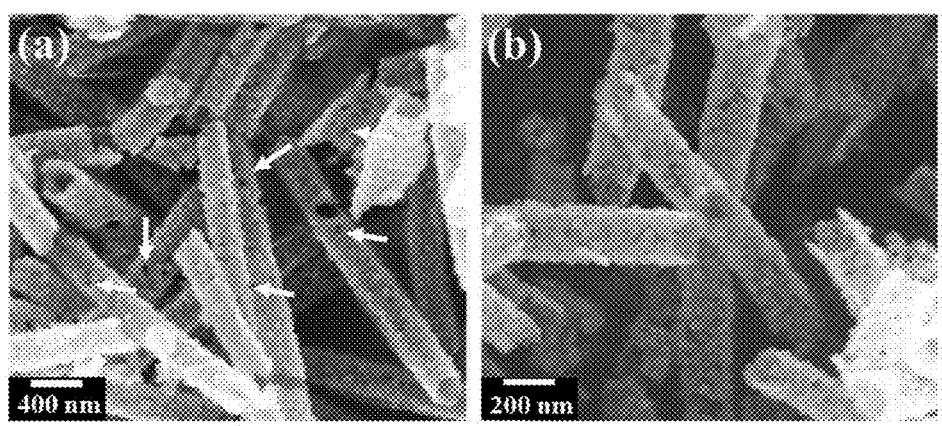
FIGS. 9(a) and 9(b) are SEM images of a one-dimensional porous metal oxide nanotube which contains a Pt nanoparticle catalyst obtained by electrospinning an electrospinning solution prepared by adding Pt nanoparticles synthesized using tin oxide precursor/polyvinylpyrrolidone (PVP) and an apoferritin and a spherical polymer sacrificial template colloid and conducting a high-temperature heat treatment and includes mesopores and macropores according to Embodiment Example 2 of the inventive concept.

FIGS. 9(a) and 9(b) are SEM images of the one-dimensional porous tin oxide nanotube which contains the Pt nanoparticle catalyst synthesized in Embodiment Example 1 and has a double surface pore distribution. The diameter of the nanotube thus fabricated has a size of about from 50 nm to 5 μm, the thickness between the outer wall and the inner wall of the tube is in a range of from 10 nm to 50 nm. In addition, the size of the mesopores formed on the nanotube surface is in a range of from 0.1 nm to 50 nm, and the macropores has a size of from 50 nm to 300 nm.

Figure 10:
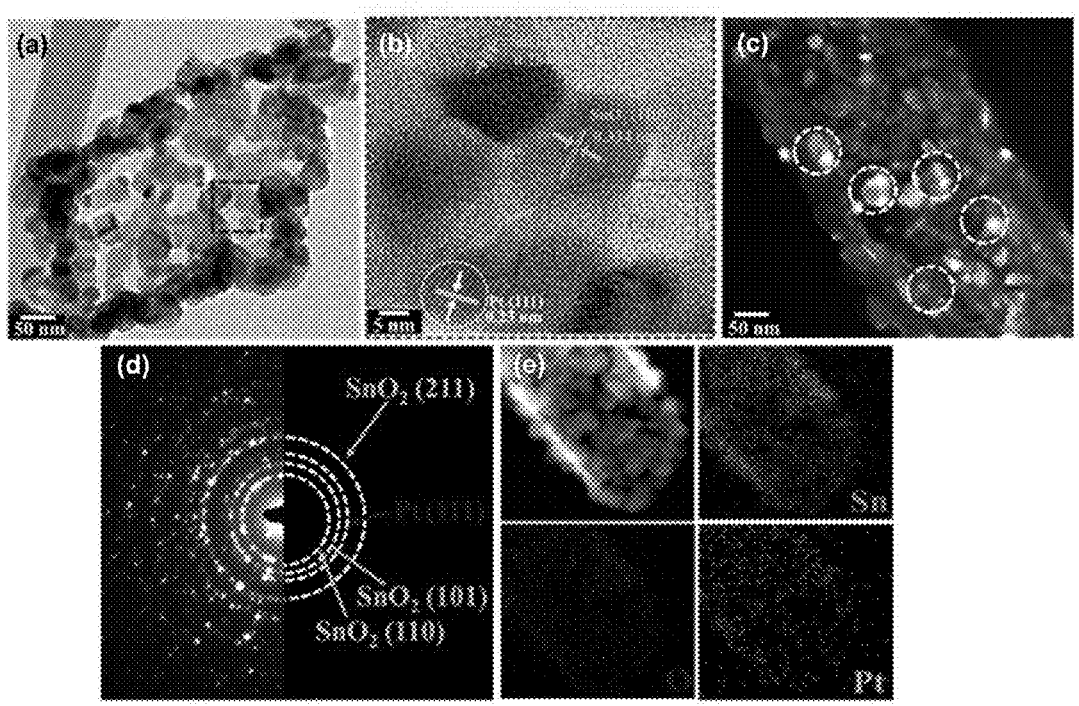
FIGS. 10(a), 10(b), and 10(c) are TEM images of a one-dimensional porous metal oxide nanotube which contains a Pt nanoparticle catalyst and includes a plurality of mesopores and macropores according to Embodiment Example 2 of the inventive concept.
FIG. 10(d) illustrates the selected area electron diffraction (SAED) pattern.
FIG. 10(e) is energy dispersive X-ray spectrometer (EDS) images.

FIGS. 10(a), 10(b), and 10(c) are TEM images of the one-dimensional porous tin oxide nanotube which contains the Pt nanoparticle catalyst synthesized in Embodiment Example 1 and has a double surface pore distribution. It can be seen that the Pt nanoparticle catalyst is inside the one-dimensional porous tin oxide nanotube by the transmission electron microscopy at a high magnification, and it is confirmed that the Pt nanoparticle catalyst exhibits crystallinity in the one-dimensional porous tin oxide nanotube by the selected area electron diffraction (SAED) pattern illustrated in FIG. 10(d). In addition, it is confirmed that various pores having a size of from 5 to 150 nm are distributed on the tin oxide nanotube surface from the images taken using a transmission electron microscope. In addition, it is confirmed that the Pt nanoparticle catalyst is uniformly distributed in the tin oxide nanotube structure from the energy dispersive X-ray spectrometer (EDS) images through the TEM illustrated in FIG. 10(e).

Figure 11:
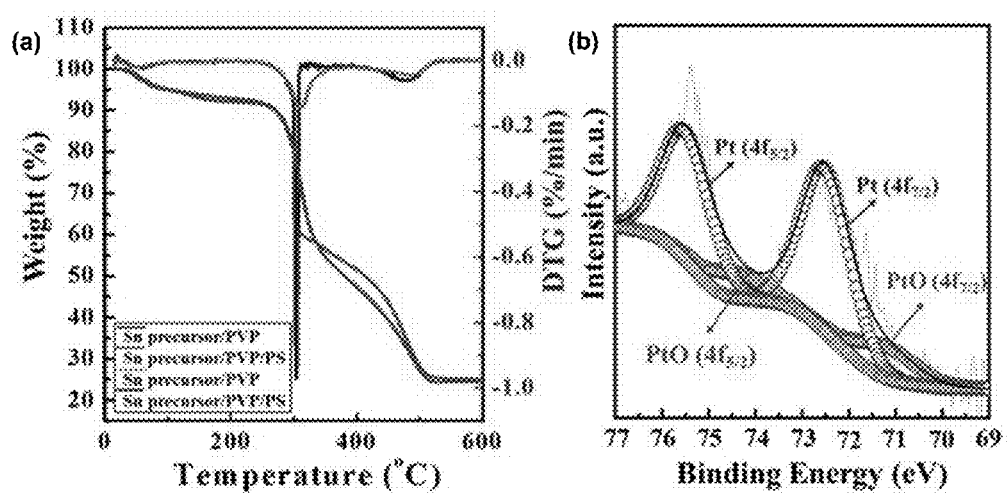
FIGS. 11(a) and 11(b) are the thermogravimetric analysis graph and the photoelectron spectroscopic (XPS) analysis graph of a one-dimensional porous metal oxide nanotube which contains a Pt nanoparticle catalyst and includes a plurality of mesopores and macropores according to Embodiment Example 2 of the inventive concept, respectively.

FIGS. 11(a) and 11(b) are the thermogravimetric analysis graph and the photoelectron spectroscopic (XPS) analysis graph of the one-dimensional porous tin oxide nanotube which contains the Pt nanoparticle catalyst synthesized and has mesopores and macropores, respectively. Through the thermogravimetric analysis (TGA), it can be seen that the macropores (50 to 300 nm) are formed as the sacrificial template polymer is removed at about 300° C. and the mesopore (0.1 to 50 nm) are formed as the crystallization and diffusion of the metal oxide subsequently occur to cover the macropores at about 400° C. Through the photoelectron spectroscopic (XPS) analysis, it is confirmed that PtO that is an oxidized state of the Pt nanoparticles and the Pt metallic form coexist.

Comparative Example 1: Fabrication of Pure Tin Oxide Nanotube not Contain Nanoparticle Catalyst In Comparative Example 1 to be compared with Embodiment Example 2, a pure tin oxide nanotube which does not contain the Pt nanoparticle catalyst and does not have circular or elliptical pores is synthesized. Specifically, 0.25 g of tin chloride dihydrate of the metal oxide precursor is dissolved in a mixed solvent (1.35 g of DMF+1.35 g of ethanol), and in order to increase the viscosity of the mixed solution, 0.35 g of polyvinylpyrrolidone (PVP) polymer having a molecular weight of 1,300,000 g/mol is added thereto and the mixture is sufficiently stirred. The stirring conditions referred to herein means that the stirring is conducted at a rotational speed of 500 rpm for at least 5 hours. The tin oxide precursor/polymer mixed electrospinning solution thus prepared is filled in the syringe for electrospinning (Henke-Sass Wolf, 10 mL NORM-JECT®), the syringe is connected to the syringe pump, and the electrospinning solution is pushed out at a discharge speed of 0.1 ml/min, thereby conducting the electrospinning. The needle used during electrospinning is a 25 gauge needle, and a high voltage of about 14 kV is applied while maintaining the distance between the nozzle the collector to collect the nanofibers to be 26 cm, thereby fabricating the tin oxide precursor/polymer composite nanofiber.

The tin oxide precursor/polymer composite nanofiber synthesized above is subjected to a high-temperature heat treatment to remove the polymer, and the tin oxide precursor is subjected to the oxidation to form tin oxide. The high-temperature heat treatment is conducted for 1 hour at 600° C., the heating rate is constantly maintained at 10° C./min, and the cooling rate is constantly maintained at 40° C./min.

Here, it is important to set the heating rate to 10° C./min to be relatively high for the formation of the nanotube structure.

Figure 12:
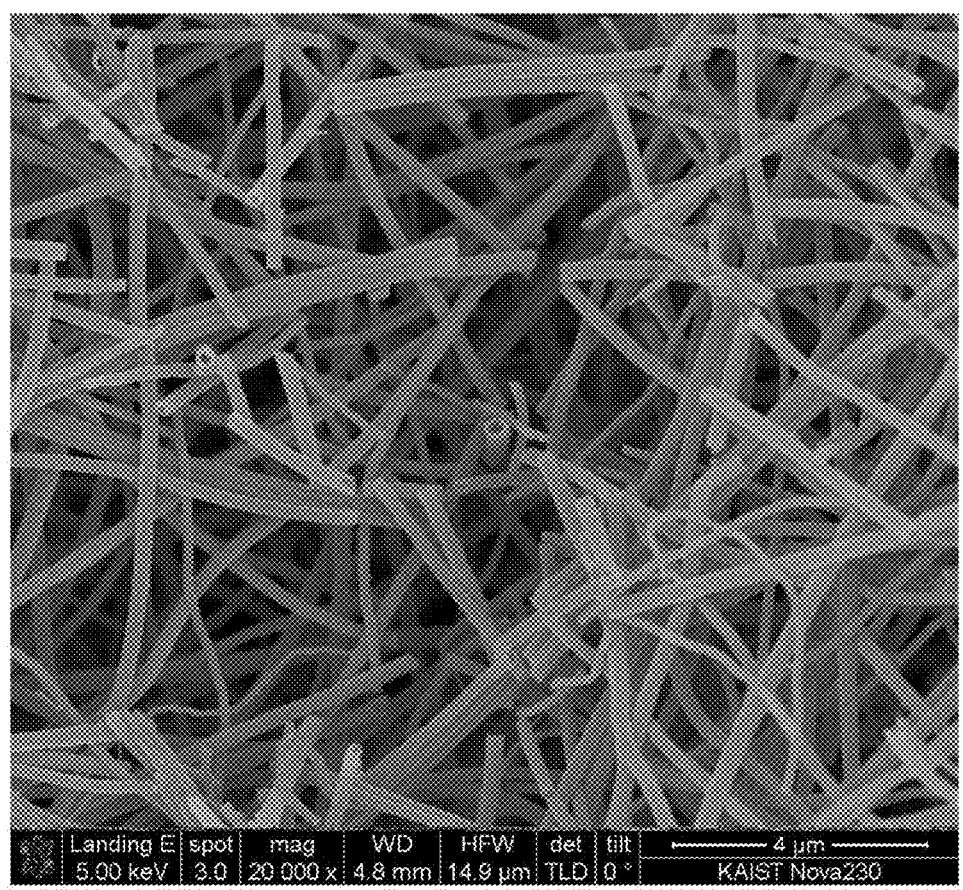
FIG. 12 is a SEM image of a metal oxide nanotube obtained by electrospinning a metal oxide precursor/polyvinylpyrrolidone (PVP) composite electrospinning solution and by conducting a high-temperature heat treatment under a high heating rate condition according to Comparative Example 1 of the inventive concept.

FIG. 12 is a SEM image of the pure tin oxide nanotube fabricated in Comparative Example 1. It is confirmed that the diameter of the tin oxide nanotube thus synthesized is in a range of from 50 nm to 5 μm, and the thickness between the inner and outer walls of the nanotube has a value between 10 and 50 nm.

Comparative Example 2: Fabrication of Pure Tin Oxide One-Dimensional Porous Nanotube not Containing Nanoparticle Catalyst In Comparative Example 2 to be compared with Embodiment Example 2, a pure tin oxide one-dimensional porous nanotube having circular and elliptical pores is synthesized by adding a spherical polystyrene sacrificial template but not adding a Pt nanoparticle catalyst embedded in an apoferritin. Specifically, 0.25 g of tin chloride dihydrate of the metal oxide precursor is dissolved in a mixed solvent (1.35 g of DMF+1.35 g of ethanol). Additionally, 0.3 g of polystyrene colloids which has a diameter of 200 nm and serves as the spherical sacrificial template is added thereto and dispersed. The dispersion condition referred to herein means that the stirring is conducted at a rotational speed of 500 rpm for at least 1 hour. In order to increase the viscosity of the tin oxide/polystyrene composite solution, 0.35 g of polyvinylpyrrolidone (PVP) polymer having an average weight of 1,300,000 g/mol is added thereto and the mixture is sufficiently stirred. The stirring conditions referred to herein means that the stirring is conducted at a rotational speed of 500 rpm for at least 10 hours. The metal precursor/polystyrene sacrificial template/polymer electrospinning solution that is sufficiently stirred is filled in the syringe for electrospinning (Henke-Sass Wolf, 10 mL NORM-JECT®), the syringe is connected to the syringe pump, the electrospinning solution is pushed out at a discharge speed of 0.1 ml/min, the needle used during electrospinning is a 25 gauge needle, and a high voltage of about 14 kV is applied while maintaining the distance between the nozzle the collector to collect the nanofibers to be 26 cm, thereby fabricating the tin oxide precursor/polystyrene sacrificial template/polymer composite nanofiber.

The tin oxide precursor/polystyrene sacrificial template/polymer composite nanofiber synthesized above is subjected to a high-temperature heat treatment to remove the polymer, circular or elliptical macropores are formed as the spherical polystyrene sacrificial template is decomposed, and mesopores are then formed as the macropores are filled by the crystallization and diffusion of tin oxide, thereby forming a one-dimensional porous pure tin oxide nanotube. The high-temperature heat treatment is conducted for 1 hour at 600° C.

Figure 13:
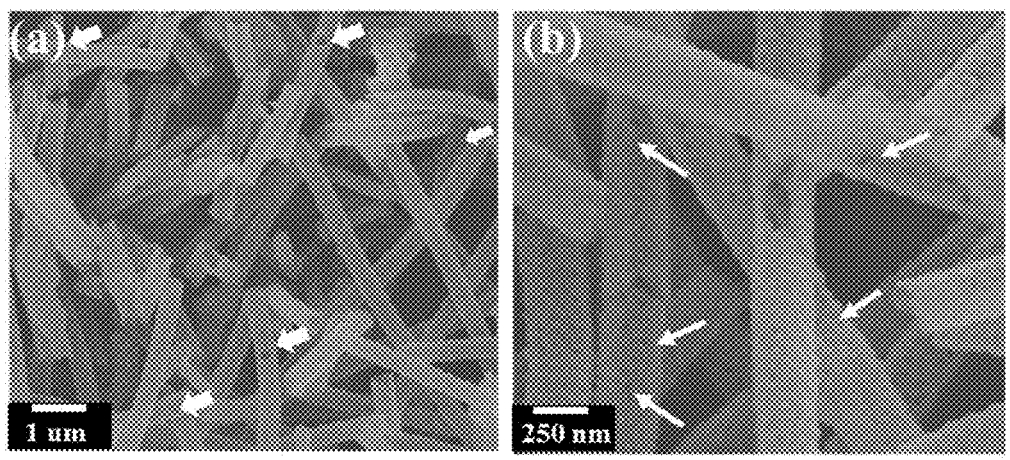
FIGS. 13(a) and 13(b) are SEM images of a one-dimensional porous metal oxide nanotube which is obtained by subjecting a metal oxide precursor/polyvinylpyrrolidone (PVP) composite nanofiber containing a spherical polymer sacrificial template to a high-temperature heat treatment under a high heating rate condition and has a double pore distribution according to Comparative Example 2 of the inventive concept.

FIGS. 13(a) and 13(b) are SEM images of the pure tin oxide nanotube structure which is fabricated in Comparative Example 2 and has circular or elliptical pores. It is confirmed that the one-dimensional porous tin oxide nanotube thus fabricated has a diameter in a range of from 50 nm to 5 μm, and the thickness between the inner and outer walls of the nanotube has a value in a range of from 10 and 50 nm. Here, the size of the mesopores has a value between 0.1 nm and 50 nm, and the macropores has a size of from 50 nm to 300 nm. It is confirmed that the size of the pores is relatively large unlike in Embodiment Example 2 since the particle growth of tin oxide is not interfered by the protein template, apoferritin.

Experimental Example 1: Manufacture of Gas Sensor Using One-Dimensional Porous Tin Oxide Nanotube Having Pt Nanoparticle Catalyst Uniformly Loaded on Inner and Outer Walls of Tube and a Number of Circular and Elliptical Pores, Tin Oxide One-Dimensional Porous Nanotube Having Pores, and Pure Tin Oxide Nanotube, and Evaluation on Characteristics Thereof In order to manufacture exhaled breath sensors using the sensing materials for gas sensor fabricated in Embodiment Examples 1 and 2 and Comparative Examples 1 and 2, 6 mg of each of the one-dimensional porous tin oxide nanotube which contains the Pt nanoparticle catalyst and has a number of mesopores and macropores, the one-dimensional porous tin oxide nanotube, and tin oxide nanotube is dispersed in 100 μl of ethanol and subjected to the ultrasonic cleaning for 1 hour to be ground. During the grinding, the porous nanotube structure synthesized above may have a porous nanotube structure shortened in the longitudinal direction.

The one-dimensional porous tin oxide nanotube uniformly loaded with the Pt nanoparticle catalyst and having a number of circular and elliptical pores, the one-dimensional porous tin oxide nanotube, and the tin oxide nanotube are coated on the upper portion of the alumina substrate which has a size of 3 mm×3 mm and on which parallel gold (Au) electrodes are formed at an interval of 150 μm by drop coating. As the coating process, 3 μl of a mixed solution of the one-dimensional porous nanotube loaded with the Pt nanoparticle catalyst, the one-dimensional porous tin oxide nanotube, and the tin oxide nanotube dispersed in ethanol was coated on the alumina substrate having the sensor electrode using a micropipette and dried on a hot plate at 60° C., and this process was repeated 4 to 6 times so as to coat a sufficient amount of sensing material on the upper portion of the alumina sensing plate.

In addition, for the simulation characteristic evaluation as a exhaled breath sensor, the response characteristics of the gas sensor thus fabricated with respect to acetone ($CH_3COCH_3$), hydrogen sulfide ($H_2S$), and toluene ($C_6H_5CH_3$) of the biomarker gas for the diagnosis of diabetes, halitosis, and lung cancer, respectively, were evaluated at a relative humidity of 85-95% RH to be similar to the humidity of gases in the exhaled breath of a human body by changing the concentration of the respective gases from 5 to 4, 3, 2, 1, 0.6, 0.4, 0.2, and 0.1 ppm and maintaining the driving temperature of the sensor at 350° C. at the same time. In addition, in Experimental Example 1, the selective gas sensing characteristics were investigated by evaluating the sensing characteristics not only for acetone ($CH_3COCH_3$), hydrogen sulfide ($H_2S$), and toluene ($C_6H_5CH_3$) of the representative examples of the volatile organic compound gas but also for nitric oxide (NO), carbon monoxide (CO), ammonia ($NH_3$), and pentane ($C_5H_{12}$) of the biomarker gas of asthma, chronic obstructive pulmonary disease, nephritis, and heart disease.

Additionally, in order to evaluate the capability to sense the exhaled breath of a healthy person and a real diabetic patient, the exhaled breath of 10 healthy people was prepared and the exhaled breath of a simulated diabetic patient was prepared so as to be similar to the exhaled breath of a real diabetic patient. The exhaled breath thus prepared was directly sensed by the sensor array, and the measured sensing results were subjected to the principal component analysis (PCA) to compare the exhaled breath of the diabetic patient with that of healthy people.

FIG. 14(a) is a graph illustrating the time course response properties ($R_{air}/R_{gas}$, where $R_{air}$ means the resistance value of the metal oxide material when the air is injected, and $R_{gas}$ means the resistance value of the metal oxide material when acetone is injected) when the concentration of acetone decreases from 5 to 4, 3, 2, 1, 0.6, 0.4, 0.2, and 0.1 ppm at 350° C. In addition, FIG. 14(b) is a graph illustrating the detection limit of the one-dimensional porous nanotube loaded with the Pt nanoparticle catalyst using linear approximation.

Figure 14:
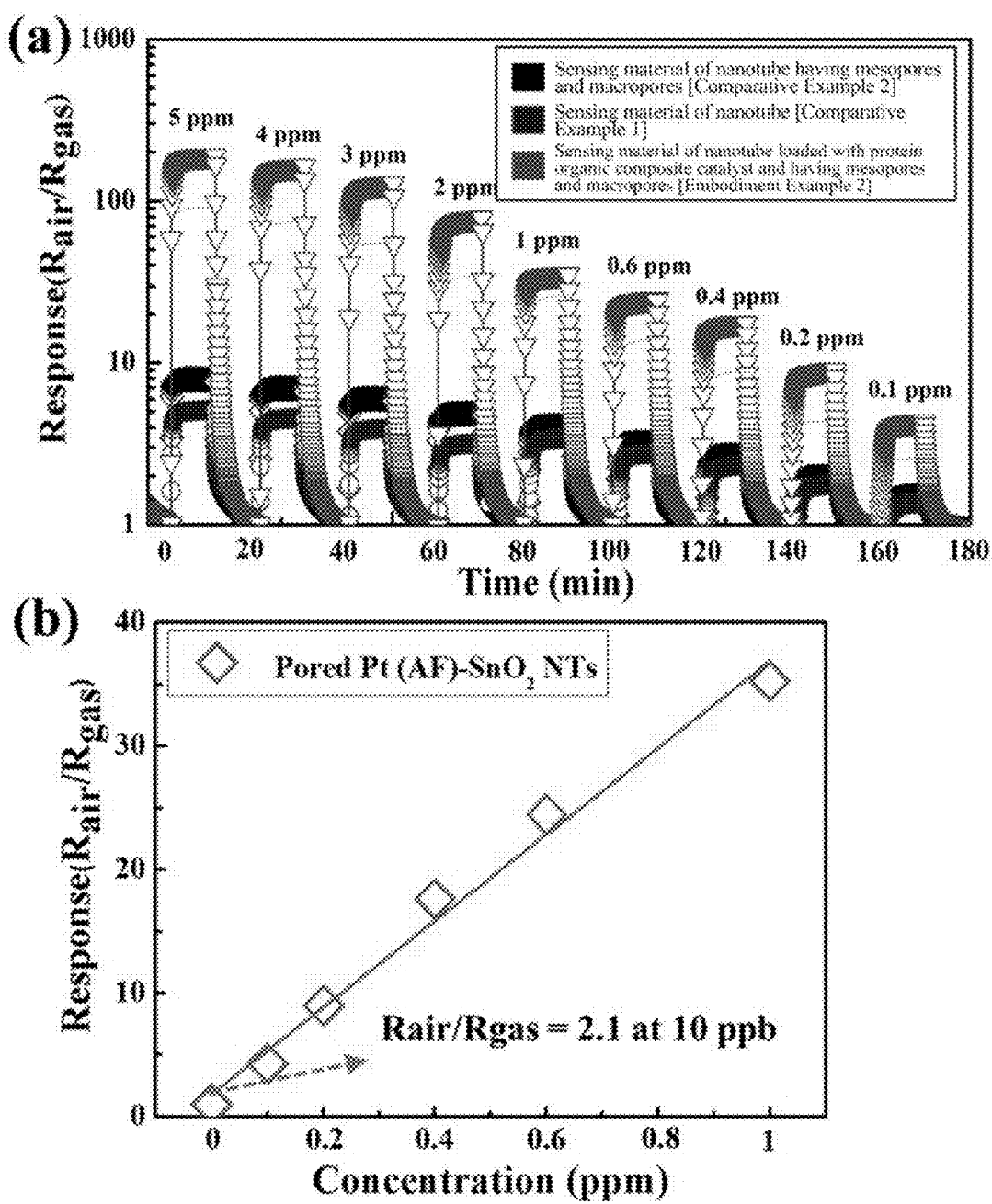
FIG. 14(a) is a graph illustrating the acetone (100 ppb to 5 ppm) response properties of a one-dimensional porous metal oxide nanotube which contains a Pt nanoparticle catalyst and includes a plurality of mesopores and macropores according to Embodiment Example 2 of the inventive concept, a pure tin oxide nanotube structure according to Comparative Example 1, and a one-dimensional porous tin oxide nanotube structure having a double pore distribution composed of a plurality of circular and elliptical pores according to Comparative Example 2 at 350° C.
FIG. 14(b) is a graph illustrating the acetone detection limit characteristics of a one-dimensional porous metal oxide nanotube sensing material which contains a Pt nanoparticle catalyst and includes a plurality of mesopores and macropores according to Embodiment Example 2 of the inventive concept.

As illustrated in FIG. 14, the sensing characteristics of the one-dimensional porous tin oxide nanotube sensing material on which the Pt nanoparticle catalyst embedded in the hollow structure of a apoferritin is loaded through the heat treatment with respect to 5 ppm acetone is 21.1 times as high as that of the one-dimensional porous tin oxide nanotube not containing a catalyst and 38 times as high as that of the pure tin oxide nanotube. In addition, the detection limit of the one-dimensional porous tin oxide nanotube sensing material loaded with the Pt nanoparticle catalyst that is obtained based on the sensing results measured at the acetone concentration of 5, 4, 3, 2, 1, 0.6, 0.4, 0.2, and 0.1 ppm using the linear approximation is 2.1 as the sensitivity ($R_{air}/R_{gas}$) at the acetone concentration of 10 ppb.

Figure 15:
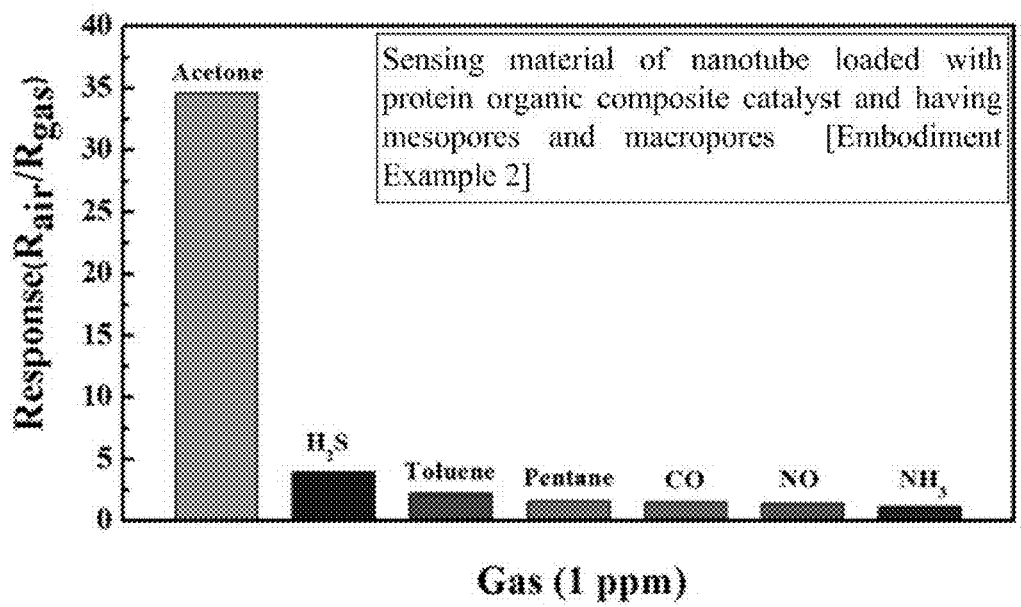
FIG. 15 is a graph illustrating the response properties of a gas sensor having a one-dimensional porous metal oxide nanotube structure which contains a Pt nanoparticle catalyst and includes a plurality of mesopores and macropores according to Embodiment Example 2 of the inventive concept to biomarker gases such as acetone ($CH_3COCH_3$), toluene ($C_6H_5CH_3$), hydrogen sulfide ($H_2S$), nitrogen monoxide (NO), carbon monoxide (CO), pentane ($C_5H_{12}$), and ammonia ($NH_3$) at 1 ppm and 350° C.

FIG. 15 is a graph illustrating the response value of a gas sensor using the one-dimensional porous tin oxide nanotube on which the Pt nanoparticle catalyst embedded in the apoferritin is loaded through the heat treatment and has a number of circular and elliptical pores with respect to hydrogen sulfide, toluene, nitrogen monoxide, carbon monoxide, ammonia, and pentane of biomarker gases of other diseases together with the response value with respect to acetone of the biomarker gas of diabetes and lipolysis at a concentration of 1 ppm and 350° C.

As illustrated in FIG. 15, a gas sensor fabricated using the one-dimensional porous tin oxide nanotube which has a double pore distribution and is loaded with the Pt nanoparticle catalyst exhibits specifically excellent selective sensing characteristics with respect to acetone of the biomarker gas of diabetes and lipolysis compared to hydrogen sulfide, toluene, pentane, carbon monoxide, ammonia, and nitrogen monoxide of biomarker gases of other diseases.

Figure 16:
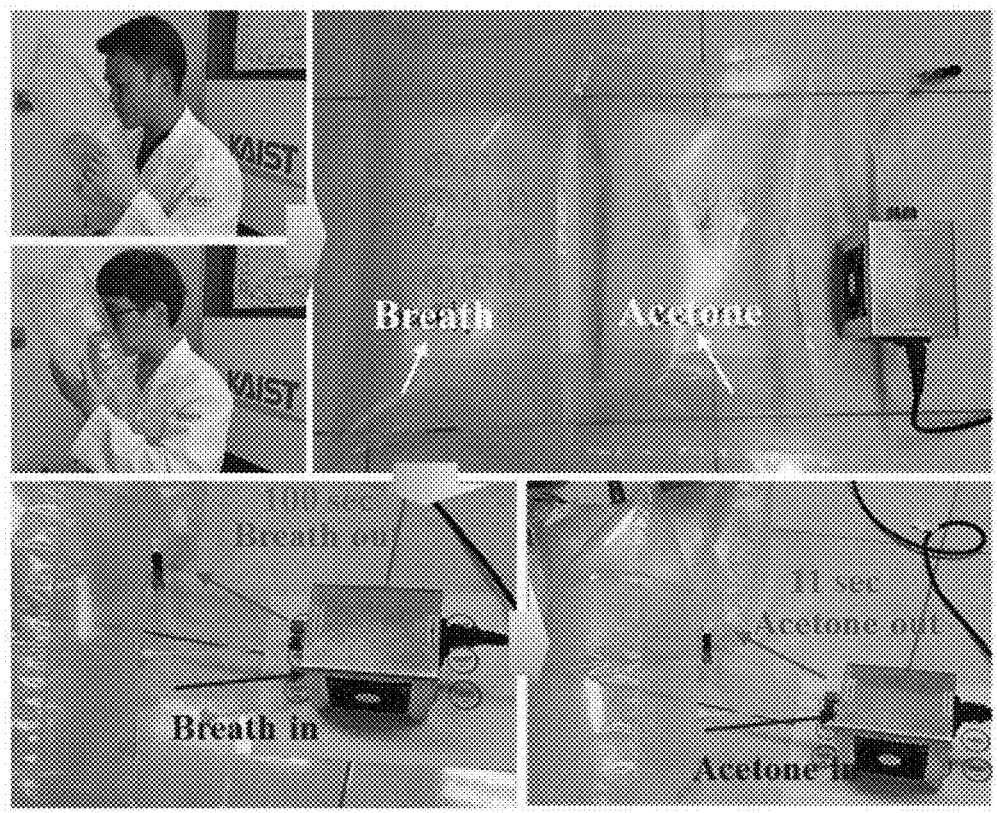
FIG. 16 is a diagram illustrating a process to collect the exhaled breath of 10 healthy people and a process to prepare the exhaled breath of simulated diabetic patients so that the exhaled breath is adjusted similar to the exhaled breath of a real diabetic patient according to an embodiment of the inventive concept.

FIG. 16 is a diagram illustrating a process to prepare the exhaled breath of 10 simulated diabetic patients by collecting the exhaled breath of 10 healthy people in Tedler bags and quantitatively injecting concentrated acetone so as to have an acetone concentration of about 2 ppm in the exhaled breath of a human body. As illustrated in FIG. 16, it is possible to set the acetone concentration in the exhaled breath of a human body to 2 ppm by using a diaphragm pump to quantitatively suck and discharge the gas.

Figure 17:
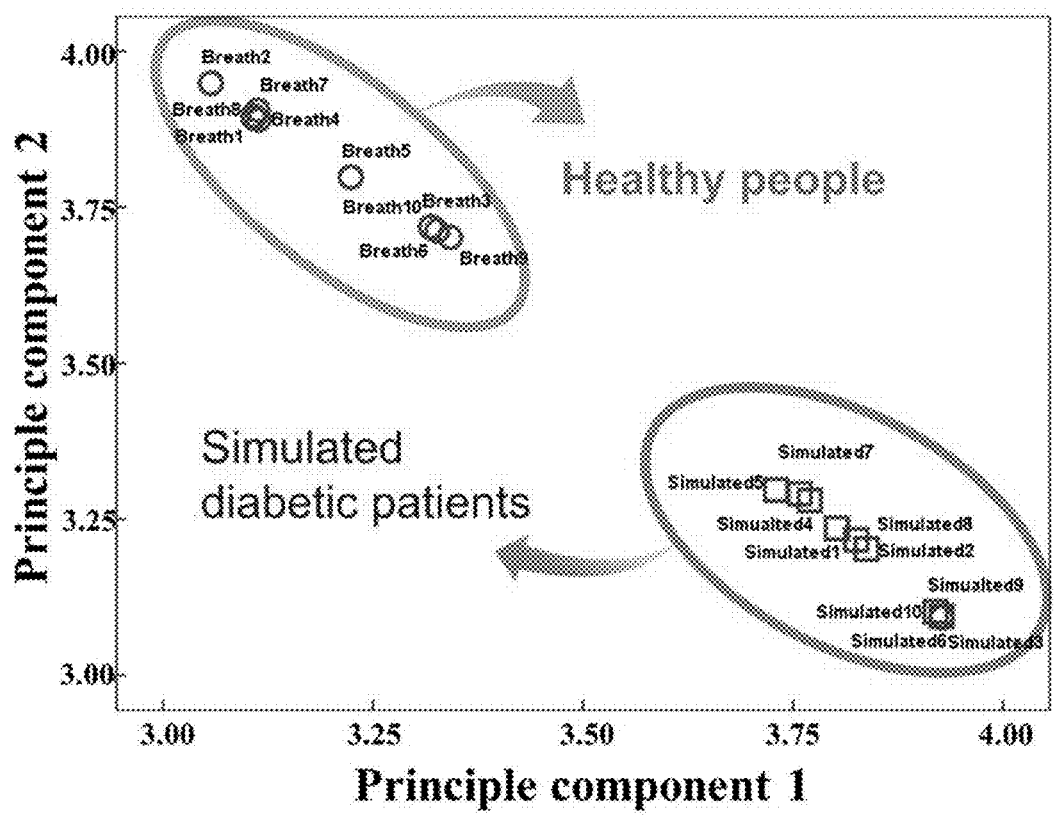
FIG. 17 is a graph illustrating the results of principal component analysis (PCA) on the exhaled breath of healthy people and the exhaled breath of simulated diabetic patients using arrays of the sensing materials produced according to embodiments of the inventive concept, which shows that the exhaled breath of simulated diabetic patients is distinguished from that of healthy people.

FIG. 17 is a graph illustrating the results of principal component analysis (PCA) on the sensing results obtained by injecting the exhaled breath of 10 healthy people actually collected and the exhaled breath of the simulated diabetic patients into the sensor array composed of the porous tin oxide nanotube which is loaded with a platinum nanoparticle catalyst and have mesopores and macropores, the tin oxide nanotube loaded with a platinum nanoparticle catalyst, and the tin oxide nanotube having mesopores and macropores. As illustrated in FIG. 17, it can be seen that the region of the exhaled breath of the simulated diabetic patients is apparently distinguished from the region of the exhaled breath of the 10 healthy people, and it is confirmed that it is possible to diagnose diabetes through the exhaled breath by using the material developed in the inventive concept.

In Experimental Example 1, the sensing characteristics of the gas sensing material with respect to the biomarker gases are evaluated. However, it is expected that the gas sensing material exhibits excellent sensing characteristics with respect to $H_2$, $NO_x$, $SO_x$, HCHO, $CO_2$ of harmful environmental gases as well, and a gas sensor exhibiting excellent selectivity to harmful gases other than acetone can be manufactured by changing the catalyst from the Pt nanoparticle catalyst embedded in an apoferritin to various kinds of catalytic particles which are synthesized by embedding catalytic materials such as Au, Pd, Rh, Cr, Co, and Ni in an apoferritin. In addition, it is possible to manufacture a nanosensor array exhibiting ultrahigh sensitivity and high selectivity by using a one-dimensional porous multi-kind metal oxide nanotube having a double pore distribution that is synthesized using various kinds of metal oxides to serve as a sensing material matrix and thus the multi-kind catalytic particles have a number of circular or elliptical pores. The one-dimensional porous metal oxide nanotube sensing material which has a double pore distribution and is loaded with a nanoparticle catalyst obtained from an apoferritin template can be used in an excellent gas sensor for detection of harmful environmental gases and a gas sensor for healthcare for volatile organic compound gas analysis in the exhaled breath and diagnosis of a disease.

Hereinafter, a gas sensor member and a gas sensor which use a metal oxide semiconductor nanotube structure containing a nanoparticle catalyst synthesized using an apoferritin, and manufacturing method thereof will be described in detail with reference to the accompanying drawings.

In the inventive concept, a nanotube structure is synthesized in which nanoparticle catalysts are uniformly distributed on the surface and in the inside of the nanotube shell by controlling the heating rate during the heat treatment of a tin oxide precursor/polymer composite nanofiber containing a nanoparticle catalyst synthesized using an apoferritin. In order to improve the sensing characteristics of the gas sensor using a metal oxide of the prior art, studies for improving the sensing characteristics by increasing the surface area and the porosity so as to react with a more amount of gas have been carried out, and also studies for promoting the catalytic reaction by loading a metal or metal oxide catalyst to the sensing material have been carried out. However, such studies have a disadvantage that the step of forming pores and the step of loading the catalyst on the nanofiber are separately required. In particular, there is a disadvantage that the step of synthesizing a metal or metal oxide nanoparticle catalyst and uniformly loading it on the nanofiber and the step of synthesizing nanoparticle catalyst having a size of several nm are fairly complicated, and there is a disadvantage that the step of synthesizing a tube structure or forming pores in order to increase the specific surface area is also relatively complicated, takes a long time, and requires a high cost. In order to overcome such a disadvantage, in the inventive concept, a nanoparticle catalyst having a size of from 0.1 nm to 8 nm is synthesized using an apoferritin, this is mixed with a metal oxide precursor/polymer mixed electrospinning solution, and then the nanoparticle catalyst is uniformly loaded on the surface and in the inside of the metal oxide precursor/polymer composite nanofiber by conducting the electrospinning. Moreover, the protein template encapsulating the nanoparticle catalyst and the polymer removed at the same time during a high-temperature heat treatment by controlling the heating rate, a metal oxide nanotube structure containing the nanoparticle catalyst through the Ostwald ripening, and thus it is possible to easily synthesize a sensing material in which nanoparticle catalysts are uniformly loaded on a nanotube structure having a large specific surface area without aggregation in a large scale by a single process. Here, the metal oxide semiconductor nanotube in which the nanoparticle catalysts are uniformly distributed on the outside and in the inside of the nanotube can maximize the catalytic effect when a gas reacts with the sensing material since the catalyst is uniformly distributed, the nanotube structure formed by controlling the heating rate during the heat treatment facilitates the penetration of the gas into the tube, an effective surface reaction of the gas is induced due to the increased surface area, and thus it is possible to manufacture a highly sensitive gas sensing material. In particular, it is possible to synthesize a variety of metal or metal oxide nanoparticles in the inside of an apoferritin protein and to fabricate a gas sensor exhibiting selectivity to a specific gas. In order to fabricate a gas sensor member having the characteristics described above, a gas sensor member, a gas sensor, and manufacturing methods thereof are implemented by an efficient and easy process.

Figure 18:
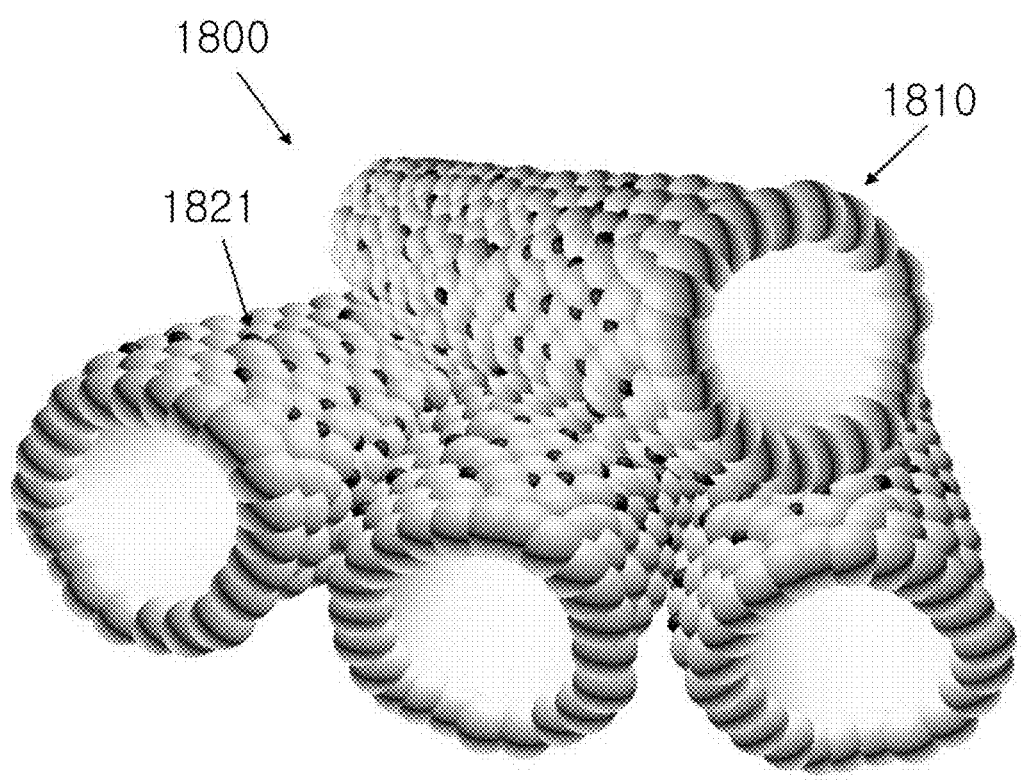
FIG. 18 is a schematic diagram of a gas sensor member in which a nanoparticle catalyst is uniformly loaded on the inside and outside of a one-dimensional metal oxide nanotube according to Embodiment Example 4 of the inventive concept.

FIG. 18 is a schematic diagram of a gas sensor member 1800 using a metal oxide semiconductor nanotube structure 1810 containing a nanoparticle catalyst 1821 according to an embodiment of the inventive concept. By subjecting a composite nanofiber fabricated by electrospinning an apoferritin protein encapsulating a nanoparticle catalyst in the hollow structure thereof with a metal oxide precursor/polymer mixed electrospinning solution to a high-temperature heat treatment at a high heating rate, it is possible to form a structure in which the tin oxide particles gather on the surface to form a nanotube 1810 having an empty structure and the nanoparticle catalysts 1821 are uniformly loaded in the inside and on the outside of the tube structure.

Here, the metal that can be synthesized in the hollow structure of the apoferritin is not particularly limited as long as it is present in an ionic form. Specific examples thereof may include Copper(II) nitrate, Copper(II) chloride, Cobalt(II) nitrate, Cobalt(II) acetate, Lanthanum(III) nitrate, Lanthanum(III) acetate, platinum(IV) chloride, platinum(II) acetate, gold(I, III) chloride, gold(III) acetate, silver chloride, silver acetate, Iron(III) chloride, Iron(III) acetate, Nickel(II) chloride, Nickel(II) acetate, Ruthenium(III) chloride, Ruthenium Acetate, Iridium(III) chloride, iridium acetate, Tantalum(V) chloride, and Palladium(II) chloride, and it is possible to synthesize a nanoparticle catalyst of Pt, Pd, Rh, Ru, Ni, Co, Cr, Ir, Au, Ag, Zn, W, Sn, Sr, In, Pb, Fe, Cu, V, Ta, Sb, Sc, Ti, Mn, Ga, or Ge using these precursors. In this manner, the size of the nanoparticle catalyst can be controlled by controlling the amount of precursor in a size range of 0.1 nm to 8 nm by using an apoferritin as a template, and there is a great advantage that the nanoparticle catalysts are surrounded with an apoferritin protein shell having a hollow structure so as to be favorably dispersed even in the electrospinning solution without being aggregated with one another. From the viewpoint of the role of nanoparticle catalyst acting in the gas sensing material, there are a nanoparticle catalyst of a noble metal, such as platinum (Pt) or gold (Au), which exhibits a chemical sensitization effect that the concentration of adsorbed oxygen ions which involve in the surface reaction is increased by promoting the decomposition reaction of oxygen molecule in between the surface of the metal oxide and the air layer and a nanoparticle catalyst which exhibits an electronic sensitization effect that a catalytic reaction is caused by the oxidation, such as PdO, $Co_3O_4$, NiO, $Cr_2O_3$, CuO, $Fe_2O_3$, $Fe_3O_4$, $TiO_2$, ZnO, $SnO_2$, $V_2O_5$, or $V_2O_3$, which affects the improvement in sensing characteristics.

It is possible to favorably disperse the nanoparticle catalysts without aggregation when the nanoparticle catalysts 1821 synthesized using an apoferritin are loaded in the inside and on the outside of the nanotube structure as compared to the nanoparticle catalysts synthesized using a general polyol process since a nanoparticle catalyst surrounded by a protein shell is used. In this respect, it is possible to uniformly load the nanoparticle catalysts in the inside and on the outside of the metal oxide precursor/polymer nanofiber as the nanoparticle catalysts are added to the metal oxide precursor/polymer mixed electrospinning solution and the electrospinning is then conducted. Here, the nucleation and particle growth occur through the high-temperature heat treatment at a heating rate of 10° C./min, and a metal oxide nanotube structure containing a nanoparticle catalyst can be formed through the Ostwald ripening. The diameter of the metal oxide nanotube structure containing a nanoparticle catalyst is in a diameter range of from 50 nm to 5 μm, the thickness between the inner and outer walls is in a range of from 10 nm to 50 nm, and the length is in a range of from 1 μm to 100 μm.

The metal oxide semiconductor nanotube constituting the nanostructure is not particularly limited to a specific material as long as the value of the electrical resistance and the electrical conductivity is changed by the adsorption and desorption of gas. Specifically, the nanotube may be a nanotube composed of one or a composite material of two or more selected from ZnO, $SnO_2$, $WO_3$, $Fe_2O_3$, $Fe_3O_4$, NiO, $TiO_2$, CuO, $In_2O_3$, $Zn_2SnO_4$, $Co_3O_4$, PdO, $LaCoO_3$, $NiCo_2O_4$, $Ca_2Mn_3O_8$, $V_2O_5$, $Cr_2O_3$, $Nd_2O_3$, $Sm_2O_3$, $Eu_2O_3$, $Gd_2O_3$, $Tb_4O_7$, $Dy_2O_3$, $Ho_2O_3$, $Er_2O_3$, $Yb_2O_3$, $Lu_2O_3$, $Ag_2V_4O_{11}$, $Ag_2O$, $Li_{0.3}La_{0.57}TiO_3$, $LiV_3O_8$, $InTaO_4$, $CaCu_3Ti_4O_{12}$, $Ag_3PO_4$, $BaTiO_3$, $NiTiO_3$, $SrTiO_3$, $Sr_2Nb_2O_7$, $Sr_2Ta_2O_7$, or $Ba_{0.5}Sr_{0.5}CO_{0.8}Fe_{0.2}O_{3-7}$.

By using the gas sensor member 1800 using the metal oxide semiconductor nanotube 1810 containing the nanoparticle catalyst 1821 described above, it is possible to configure a ultrahigh sensitive sensor which can diagnose a human body disease at the early stage by selectively sensing a specific gas which acts as a biomarker in the exhaled breath of a human body and can also be applied to an environmental sensor capable of monitoring harmful environmental gases. In addition, it is possible to quantitatively control the loading amount of the nanoparticle catalyst that is loaded on the nanotube while quantitatively controlling the amount of the nanoparticle catalyst and thus the catalytic properties can be effectively controlled, it is possible to effectively control the surface area of the fibers from a structure in which the inside of the nanofiber is filled to a nanotube structure by controlling the heating rate during the heat treatment, and thus there is also an advantage of being able to rapidly and easily fabricate a variety of gas sensor members.

Figure 19:
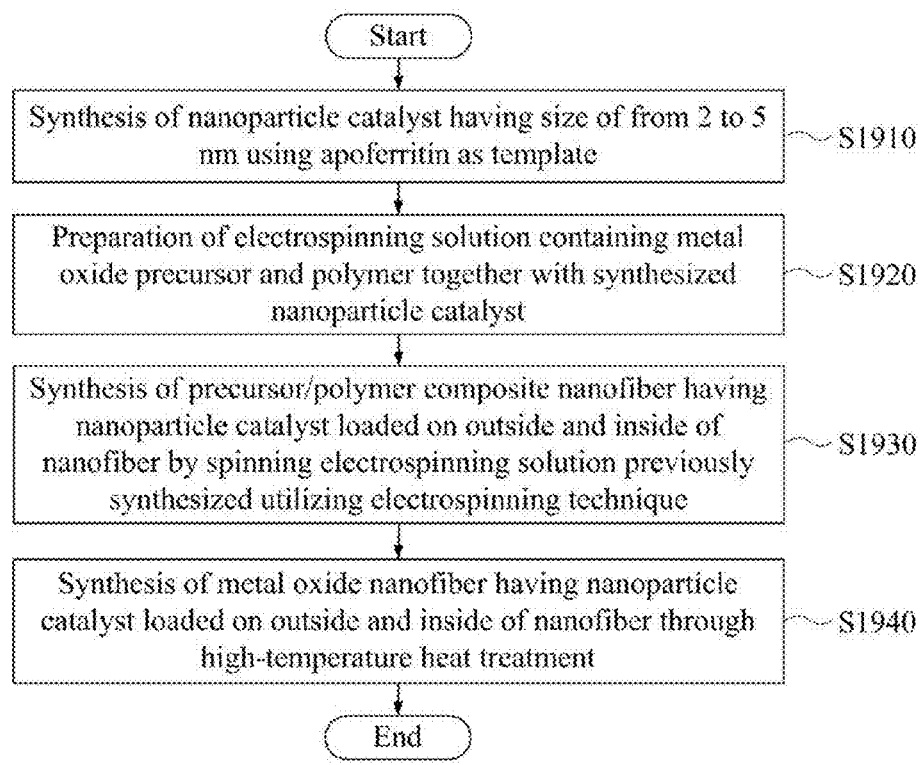
FIG. 19 is a flow chart of a manufacturing method of a gas sensor using a metal oxide nanotube structure containing a nanoparticle catalyst synthesized using an apoferritin according to Embodiment Example 4 of the inventive concept.

FIG. 19 is a flow chart of a manufacturing method of a gas sensor member using a metal oxide semiconductor nanotube containing a nanoparticle catalyst synthesized using the electrospinning method according to an embodiment of the inventive concept. As illustrated in the flow chart of FIG. 19, the manufacturing method of a gas sensor member may include a step S1910 of synthesizing a nanoparticle catalyst using an apoferritin, a step S1920 of preparing a composite electrospinning solution by adding the nanoparticle catalyst synthesized in the previous step to a metal oxide precursor/polymer electrospinning solution, a step S1930 of synthesizing a metal oxide precursor/polymer composite nanofiber containing the nanoparticle catalyst synthesized using an apoferritin from the composite electrospinning solution utilizing electrospinning equipment, and a step S1940 of synthesizing a metal oxide nanotube loaded with the nanoparticle catalyst through a high-temperature heat treatment at a relatively high heating rate of 10° C./min. The respective steps will be described below in more detail.

First, the step S1910 of synthesizing a nanoparticle catalyst using an apoferritin is described.

The apoferritin used in this step S1910 includes ferritin extracted from equine spleen, and an apoferritin prepared by removing the iron ion present inside a ferritin obtained from liver, spleen, or the like of a human body or a swine regardless of the extraction site may be used. As the method for removing the iron from the inside of the ferritin having a structure surrounded with a protein, it is possible to use either of a chemical method or an electrical method. Solutions of sodium chloride (NaCl) at various concentrations including saline can be used as a solution to keep the apoferritin having a hollow structure having an empty space therein, and the apoferritin is required to be stored under refrigeration at 4° C. or lower. In addition, in order to embed a metal salt in the apoferritin, a basic solution having a pH in a range of from 8.0 to 9.5 is preferable, the apoferritin is immersed in a solution containing a metal salt dissolved therein for about from 1 hour to 24 hour so that the metal salt can be sufficiently diffused into the apoferritin. The concentration of the solution for storage, such as saline containing the apoferritin is set to be in a range of from 0.1 to 200 mg/ml. As the solvent used when preparing the metal salt solution, a commercially available solvent such as ethanol, water, chloroform, N,N'-dimethylformamide, dimethylsulfoxide, N,N'-dimethylacetamide, or N-methylpyrrolidone can be used, and the solvent is not limited to a particular solvent as long as it dissolves a metal salt. The kind and form of the metal salt synthesized in the inside of the apoferritin is not particularly limited as long it is a precursor in an ionic form. The metal salt is preferably a precursor in a salt form which can embed Pt, Pd, Rh, Ru, Ni, Co, Cr, Ir, Au, Ag, Zn, W, Sn, Sr, In, Pb, Fe, Cu, V, Ta, Sb, Sc, Ti, Mn, Ga, or Ge in the apoferritin, and through the high-temperature heat treatment, the protein is removed and the nanoparticle catalysts are converted to a metal or metal oxide catalytic particles. At this time, the metal particles which are prone to be oxidized are easily converted to metal oxide particles. Such metal oxide particles may exhibit the properties of n-type or p-type semiconductor. As the reducing agent to reduce the metal salt contained inside the hollow structure of the apoferritin, a generally used reducing agent such as sodium borohydride ($NaBH_4$), formic acid (HCOOH), oxalic acid ($C_2H_2O_4$) or lithium aluminum hydride (LAIN may be used, and a reducing agent capable of reducing the metal salt so as to form a metallic nanoparticle catalyst may be used without any particular limitation. The solution subjected to the reduction of the metal salt inside the apoferritin by a reducing agent is then subjected to the centrifugation to separate the apoferritin protein embedding the nanoparticle catalyst therefrom, and the rotational speed of the centrifugal separator used at this time is preferably from 10,000 rpm to 13,000 rpm.

Subsequently, the step S1920 of preparing a metal oxide precursor/polymer mixed electrospinning solution containing the metallic nanoparticle catalyst synthesized using an apoferritin above is described.

In this step S1920, the apoferritin protein embedding the nanoparticle catalyst synthesized in the previous step is added to a metal oxide precursor/polymer mixed electrospinning solution to prepare a mixed electrospinning solution in which the nanoparticle catalysts are uniformly dispersed in the electrospinning solution. Here, as the solvent, a commercially available solvent such as N,N'-dimethylformamide, dimethylsulfoxide, N,N'-dimethylacetamide, N-methylpyrrolidone, deionized (DI) water, or ethanol may be used, but it is required to select a solvent which can dissolve the metal oxide precursor and the polymer at the same time. In addition, the polymer used herein is not limited to a specific polymer as long as it is a polymer that is removed through the high-temperature heat treatment. Specific examples of the polymer that can be used in this step S1920 may include polymethyl methacrylate (PMMA), polyvinylpyrrolidone (PVP), polyvinyl acetate (PVAc), polyvinyl alcohol (PVA), polyacrylonitrile (PAN), polyethylene oxide (PEO), polypropylene oxide (PPO), polyethylene oxide copolymer, polypropylene oxide copolymer, polycarbonate (PC), polyvinylchloride (PVC), polycaprolactone, and polyvinylidene fluoride.

The metal oxide precursor used in this step is not limited to a specific metal salt as long as it is a precursor which dissolves in a solvent and contains a metal salt capable of forming a metal oxide semiconductor nanofiber or nanotube exhibiting gas sensing characteristics through the high-temperature heat treatment, such as $SnO_2$, $WO_3$, $CuO$, $NiO$, $ZnO$, $Zn_2SnO_4$, $CO_3O_4$, $Cr_2O_3$, $LaCoO_3$, $V_2O_5$, $IrO_2$, $TiO_2$, $Er_2O_3$, $Tb_2O_3$, $Lu_2O_3$, $Ag_2O$, $SrTiO_3$, $Sr_2Ta_2O_7$, $BaTiO_3$, or $Ba_{0.5}Sr_{0.5}CO_{0.8}Fe_{0.2}O_{3-7}$.

The ratio of the metal oxide precursor to the polymer for forming the electrospinning solution is preferably about from 1:0.5 to 2, and the ratio to the polymer to the nanoparticle catalyst synthesized using the apoferritin is preferably about from 1:0.00001 to 1:0.1. The kind of the metal salt encapsulated in the apoferritin is preferably selected in consideration of the sensing characteristics and selectivity of the gas to be sensed, and it is possible to manufacture a gas sensor member exhibiting various characteristics by changing the metal salt.

As the procedure to prepare an electrospinning solution in the step S1920, the metal oxide precursor is first dissolved in a solvent, a solution of the apoferritin encapsulating the nanoparticle catalyst synthesized in advance is added thereto, and the mixed solution is mixed so as to uniformly disperse the apoferritin encapsulating the nanoparticle catalyst. After the mixed solution is sufficiently mixed, a polymer is added thereto at an appropriate ratio, and the mixture is stirred until the polymer is completely dissolved in the solution. As the stirring condition, the mixture is preferably stirred at from room temperature to 50° C., and it is sufficiently stirred for from 5 hours to about 48 hours so that the apoferritin encapsulating the nanoparticle catalyst, the metal oxide precursor, and the polymer are uniformly mixed in the solution. The electrospinning solution synthesized above is electrospun, and the step 1930 of fabricating the metal oxide precursor/polymer composite nanofiber containing the apoferritin protein encapsulating the nanoparticle catalyst through the electrospinning.

Upon carrying out the electrospinning method in order to carry out the step S1930, the electrospinning solution containing the metal oxide precursor/polymer and the apoferritin protein encapsulating the nanoparticle catalyst thus prepared is filled in a syringe, the syringe is pressed using the syringe pump at a constant rate so that a certain amount of the electrospinning solution is discharged therefrom. The electrospinning system may be constituted by a high voltage apparatus, a grounded conductive substrate, a syringe, and a syringe nozzle, a high voltage about from 5 kV to 30 kV is applied to between the solution filled in the syringe and the conductive substrate to generate the electric field, and the electrospinning solution discharged through the syringe nozzle is ejected in a long nanofiber form due to the electric field thus generated, whereby the electrospinning is conducted. The electrospinning solution ejected in a long nanofiber form is obtained as a solid polymer fiber as the solvent contained in the electrospinning solution is evaporated and volatilized and a composite fiber containing the metal oxide precursor and the apoferritin encapsulating the nanoparticle catalyst is fabricated at the same time. The discharge speed may be controlled to about from 0.01 ml/min to 0.5 ml/min, and it is possible to fabricate a metal oxide precursor/polymer/nanoparticle catalyst composite nanofiber having a desired diameter by controlling the voltage and the discharge rate.

Finally, in the step S1940 of fabricating a metal oxide nanotube structure in which the nanoparticle catalysts are uniformly distributed without being aggregated with one another through the high-temperature heat treatment of the composite nanofiber fabricated in the previous step, a metal oxide nanotube structure can be formed by controlling the heating rate during the heat treatment. The polymer and the protein encapsulating the nanoparticle catalyst are all decomposed and removed through the heat treatment at a temperature of 400 to 800° C., the metal oxide precursor and nanoparticle catalyst in the inside of the nanofiber diffuse toward the nanofiber surface through the Ostwald ripening, and a metal oxide nanotube structure is finally formed. It is possible to fabricate the metal oxide nanotube structure 1810 in which the nanoparticle catalysts are densely dispersed in the shell structure of the metal oxide nanotube by setting the heating rate to be relatively high of 10° C./min during this process.

Figure 20:
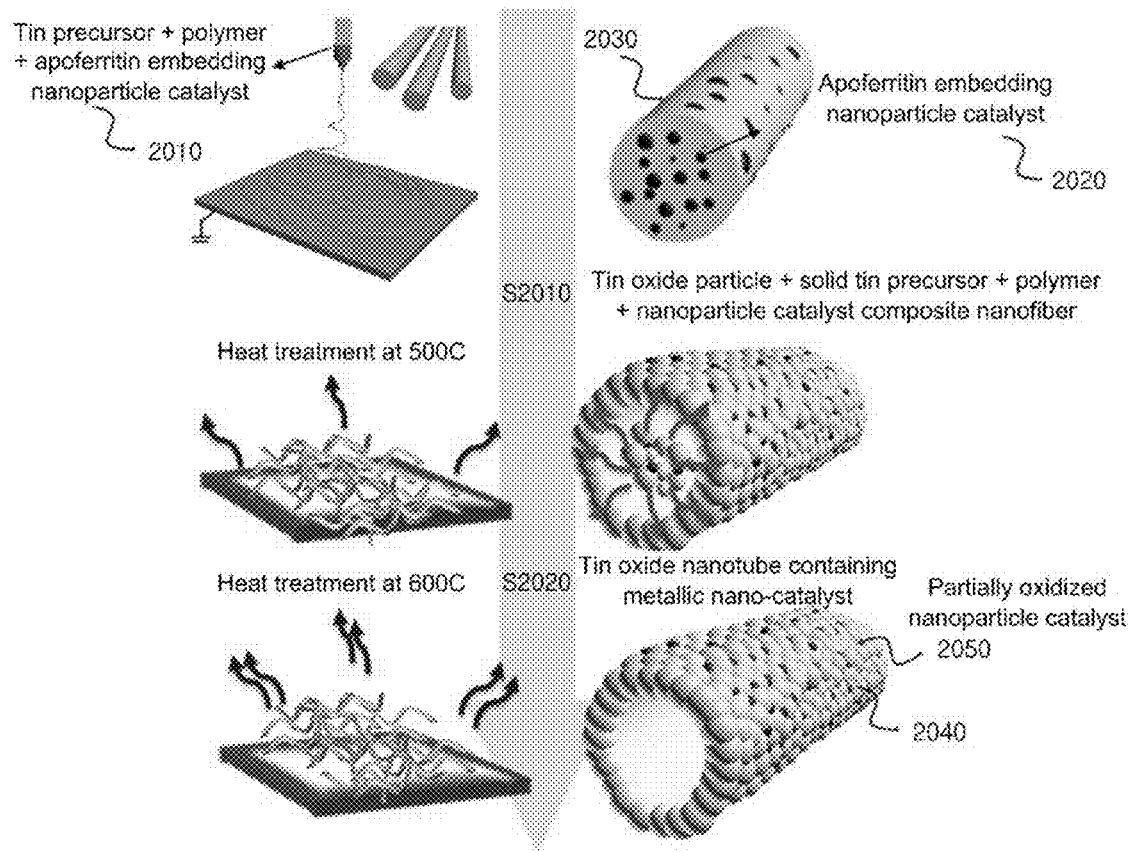
FIG. 20 is a diagram illustrating a manufacturing process of a one-dimensional metal oxide nanotube structure containing a nanoparticle catalyst using an electrospinning method according to Embodiment Example 4 of the inventive concept.

FIG. 20 is a diagram illustrating a manufacturing process according to the method for manufacturing a gas sensor member using a metal oxide semiconductor nanotube containing a nanoparticle catalyst using an electrospinning method according to an embodiment of the inventive concept.

The step S2010 of the first step illustrates an example of fabricating a nanofiber from an electrospinning solution 2010 containing a metal oxide precursor (tin precursor)/polymer and a nanoparticle catalyst embedded in the apoferritin. The nanofiber 2030 that is fabricated through the process described above and illustrated in FIG. 20 has a feature in which the apoferritin 2020 encapsulating a nanoparticle catalyst is uniformly distributed.

The step S2020 of the second step illustrates the high-temperature heat treatment of the composite nanofiber synthesized in the step S2010. The heat treatment is conducted while increasing the temperature up to 600° C. at a relatively high heating rate of 10° C./min so that the polymer and the protein encapsulating the nanoparticle catalyst are all removed and the metal oxide and the nanoparticle catalyst all diffuse toward the nanofiber surface, whereby a metal oxide semiconductor nanotube 2040 uniformly containing a metallic nanoparticle catalyst is synthesized.

In this embodiment of FIG. 20, an example of manufacturing a tin oxide nanotube structure using a tin oxide precursor is described, but the metal oxide precursor is not particularly limited as long as it contains a metal salt as described above.

As described above, in the method for manufacturing the gas sensor member 1800 using the metal oxide semiconductor nanotube 1810 containing the nanoparticle catalyst 1821 fabricated by using the electrospinning method and controlling the heating rate in the heat treatment according to embodiments of the inventive concept, a one-dimensional nanotube structure having a large surface area for the reaction with a gas is formed and a catalyst that is uniformly dispersed and exhibits a chemical/electronic sensitization effect is loaded thereto using the properties of a protein, and thus it is possible to improve the response rate characteristics, sensitivity characteristics, and selectivity of the gas sensor.

Hereinafter, the inventive concept will be described in detail with reference to Embodiment Examples and Comparative Examples. Embodiment Examples and Comparative Examples are only for explaining the inventive concept, and the inventive concept is not limited to the following Embodiment Examples.

Embodiment Example 3: Preparation of Pt and Au Nanoparticle Catalyst Using Apoferritin as Template The following procedure is used in order to synthesize Pt and Au nanoparticle catalysts inside an apoferritin having a hollow structure.

The pH of 1 ml of an apoferritin solution (Sigma Aldrich) dispersed in a 0.15 M NaCl aqueous solution at a concentration of 35 mg/ml is adjusted to 8.6 using NaOH, thereby preparing a condition for the diffusion of a metal salt diffuse into the apoferritin. The basic solution used herein is not particularly limited as long as it is a basic solution. Next, $H_2PtCl_6 \cdot H_2O$ and $H_2AuCl_6 \cdot H_2O$ are used as the Pt precursor and Au precursor which are required for the synthesis of the Pt and Au nanoparticle catalysts. In DI water, 16 mg of $H_2PtCl_6 \cdot H_2O$ and 16 mg of $H_2AuCl_6 \cdot H_2O$ are respectively dissolved to prepare aqueous solutions. The two aqueous solutions of metal salt precursors thus prepared are gradually dropped into the apoferritin solution having an adjusted pH drop and stirred so that the Pt and Au slats diffuse into the hollow of the apoferritin and are embedded therein. The stirring conditions referred to herein means that the stirring is conducted at room temperature and a rotational speed of 100 rpm for about 1 hour. After the metal salts are embedded in the apoferritin, the metal ions ($Pt^{4+}/Au^{4+}$) in the hollow of the apoferritin are reduced to metals (Pt/Au) using a reducing agent so as to form a nanoparticle catalyst. The reducing agent $NaBH_4$ used at this time is prepared as an aqueous solution at a concentration of 40 mM and added by 0.5 ml.

The aqueous solution in which the Pt nanoparticle catalyst and the Au nanoparticle catalyst which are synthesized using the apoferritin by the method as described above are dispersed contains the reducing agent and the ligand of the metal salts in a great amount, and thus the synthesized metallic nanoparticle catalysts are required to be extracted using a centrifugal separator. As the centrifugal condition, it is preferable to conduct the centrifugation at about from 10,000 rpm to 12,000 rpm for 10 minutes or longer. The apoferritin encapsulating the Pt nanoparticle catalyst and Au nanoparticle catalyst thus extracted by centrifugation is dispersed in water again, thereby preparing an aqueous solution in which the Pt nanoparticle catalyst and the Au nanoparticle catalyst are dispersed in the inside of the apoferritin.

Figure 24:
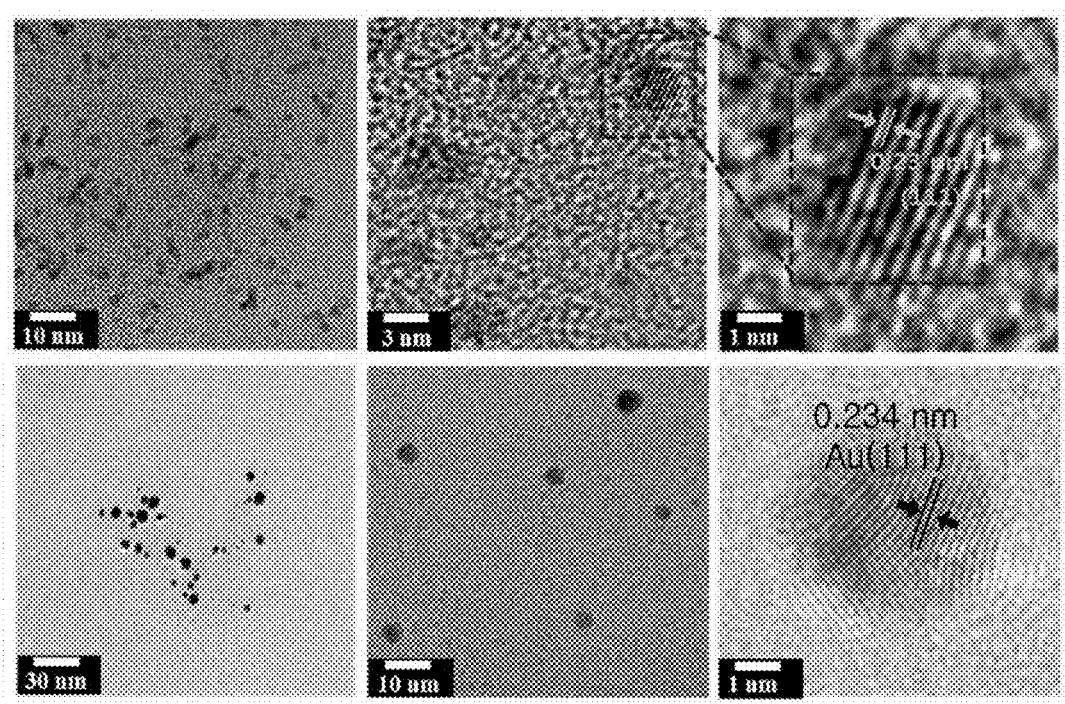
FIG. 24 is TEM images of apoferritin particles encapsulating a Pt nanoparticle catalyst and apoferritin particles encapsulating an Au nanoparticle catalyst according to Embodiment Example 3 of the inventive concept.

FIG. 24 is TEM images of the apoferritin encapsulating the Pt nanoparticle catalyst and Au nanoparticle catalyst prepared by the above process. It can be seen that the apoferritin encapsulating the Pt nanoparticle catalyst and Au nanoparticle catalyst thus synthesized has a diameter of about from 2 to 5 nm and a spherical shape.

Embodiment Example 4: Fabrication of Tin Oxide ($SnO_2$) Nanotube 2040 Structure Containing Pt and Au Nanoparticle Catalysts First, 0.25 g of tin chloride dihydrate of the metal oxide precursor is added to a mixed solvent of 1.35 g of DMF and 1.35 g of ethanol and dissolved at room temperature. Next, 200 mg of the aqueous solution of the apoferritin 2020 encapsulating the Pt nanoparticle catalyst and Au nanoparticle catalyst prepared in Embodiment Example 3 is added to and mixed with two tine oxide precursor/mixed solvent electrospinning solutions, respectively. In order to increase the viscosity of the solutions in which the apoferritin particles encapsulating the Pt nanoparticle catalyst and Au nanoparticle catalyst and the tine oxide precursor are uniformly mixed, 0.35 g of polyvinylpyrrolidone (PVP) polymer having a molecular weight of 1,300,000 g/mol is added thereto, respectively, and the mixtures are stirred at room temperature and a rotational speed of 500 rpm for 24 hours to prepare electrospinning solutions. The electrospinning solutions thus prepared are filled in the syringe (Henke-Sass Wolf, 10 mL NORM-JECT®), the syringe is connected to the syringe pump, the electrospinning solution is pushed out at a discharge speed of 0.1 ml/min, and voltage between the nozzle (needle, 27 gauge) used during electrospinning and the collector gathering the nanofibers is set to 14 kV, thereby conducting the electrospinning. At this time, stainless steel plate is used as the nanofiber collecting plate, and the distance between the nozzle and the collector is set to 15 cm.

Figure 21:
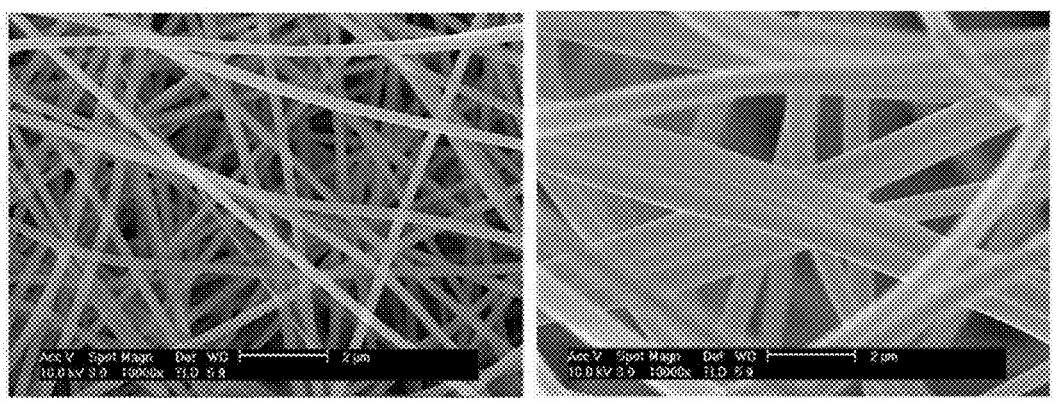
FIG. 21 is SEM images of a nanofiber obtained by electrospinning a tin oxide precursor/polyvinylpyrrolidone (PVP) composite electrospinning solution containing an apoferritin protein having a Pt nanoparticle catalyst and an Au nanoparticle catalyst encapsulated in the inside of the hollow structure according to an embodiment of the inventive concept.

FIG. 21 shows SEM images of the tin oxide precursor/polyvinylpyrrolidone composite nanofiber containing the Pt nanoparticle catalyst and the tin oxide precursor/polyvinylpyrrolidone composite nanofiber containing the Au nanoparticle catalyst obtained after the electrospinning. It can be seen that a one-dimensional nanofiber is synthesized, and the diameter has a value in between 200 nm to 300 nm.

The metal oxide precursor/polymer composite nanofiber loaded with the Pt nanoparticle catalyst and the metal oxide precursor/polymer composite nanofiber loaded with the Au nanoparticle catalyst fabricated by the method as described above are respectively maintained at 600° C. for 1 hour at a heating rate of 10° C./min and then cooled to room temperature at a cooling rate of 40° C./min. The heat treatment is conducted in an air atmosphere using the small electric furnace Vulcan 3-550 manufactured by Ney. The apoferritin protein encapsulating the nanoparticle catalyst and the polymer are all decomposed through the high-temperature heat treatment. In addition, the heat treatment is conducted in the air atmosphere, thus the tin salt precursor on the nanofiber surface is first oxidized into tin oxide particles through the nucleation and particle growth, the tin salt precursor inside the nanofiber is also oxidized through the Ostwald ripening and diffused toward the nanofiber surface to form a tin oxide nanotube, and the Pt nanoparticle catalyst and Au nanoparticle catalyst contained in the nanofiber surface also diffuse toward the nanotube surface to form a tin oxide nanotube uniformly loaded with the Pt nanoparticle catalyst and a tin oxide nanotube uniformly loaded with the Au nanoparticle catalyst.

Figure 25:
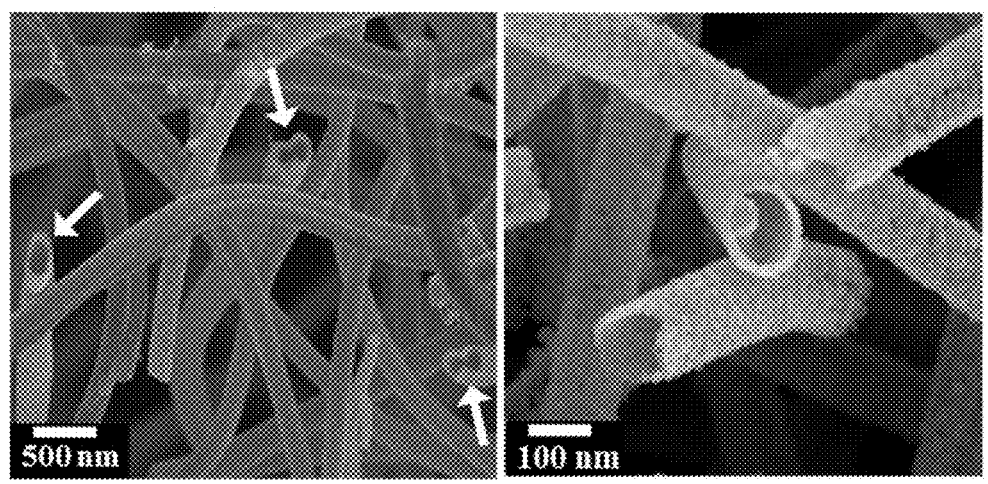
FIG. 25 is SEM images of a tin oxide nanotube containing a Pt nanoparticle catalyst and a tin oxide nanotube containing an Au nanoparticle catalyst obtained by electrospinning an electrospinning solution prepared by adding tin oxide precursor/polyvinylpyrrolidone (PVP) and Pt nanoparticles and Au nanoparticles synthesized using an apoferritin and conducting a high-temperature heat treatment under a high heating rate condition according to Embodiment Example 4 of the inventive concept.

FIG. 25 shows SEM images of the tin oxide nanotube loaded with the Pt nanoparticle catalyst and the tin oxide nanotube loaded with the Au nanoparticle catalyst obtained after the heat treatment according to Embodiment Example 4. The outer diameter of the nanotube structure thus formed has a size of about from 50 nm to 2 μm and the inner diameter thereof has a size of about from 40 nm to 1.9 μm. The thickness of the tube is about from 10 to 100 nm.

Figure 26:
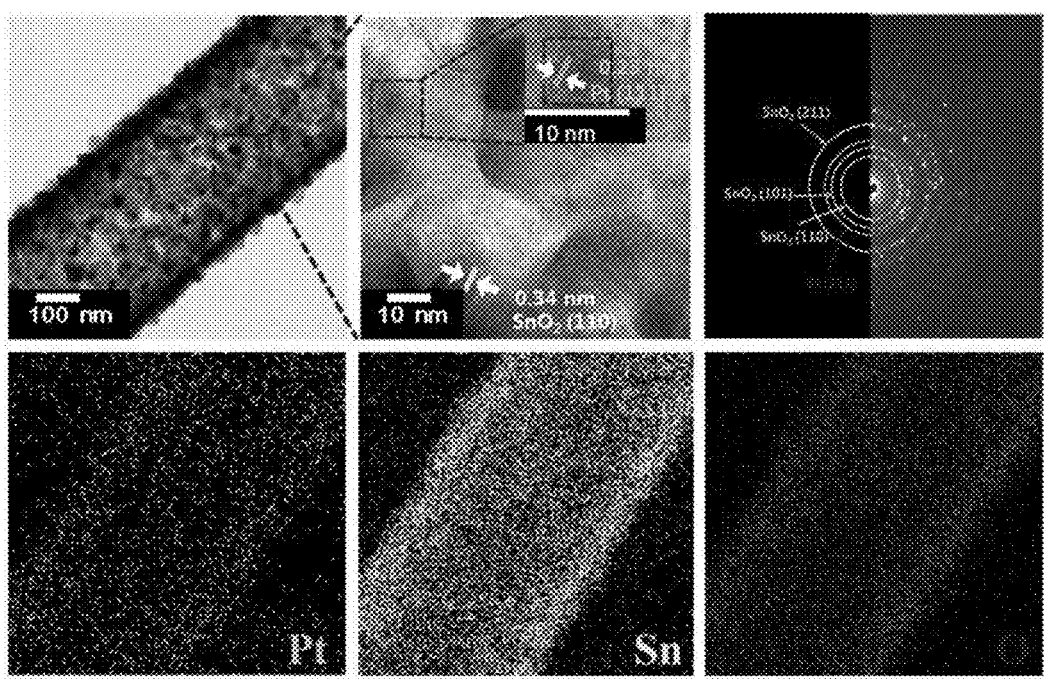
FIG. 26 is TEM and EDS images of a tin oxide nanotube structure containing a Pt nanoparticle catalyst according to Embodiment Example 4 of the inventive concept.

FIG. 26 shows TEM images of the tin oxide nanotube containing the Pt nanoparticle catalyst fabricated in Embodiment Example 4. It can be seen that the Pt nanoparticle catalysts are present in the tin oxide nanotube through the transmission electron microscope grid analysis and the Pt nanoparticle catalysts a crystallized in the tin oxide nanotube through selected area electron diffraction (SAED) pattern. In addition, it can be seen that the Pt nanoparticle catalysts are uniformly distributed in the formed tin oxide nanotube structure thus through the component analysis (EDS) image by the TEM analysis.

Figure 27:
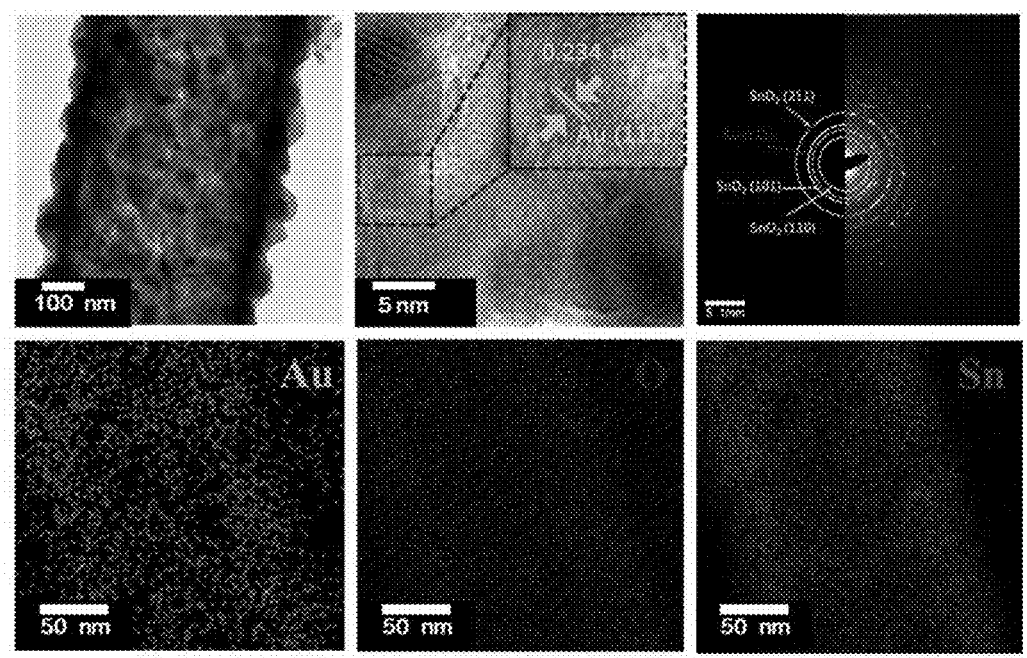
FIG. 27 is TEM and EDS images of a tin oxide nanotube structure containing an Au nanoparticle catalyst according to Embodiment Example 4 of the inventive concept.

FIG. 27 shows TEM images of the tin oxide nanotube containing the Au nanoparticle catalyst synthesized in Embodiment Example 4. It can be seen that the Au nanoparticle catalysts are present in the tin oxide nanotube through the transmission electron microscope grid analysis and the Au nanoparticle catalysts a crystallized in the tin oxide nanotube through selected area electron diffraction (SAED) pattern. In addition, it can be seen that the Au nanoparticle catalysts are uniformly distributed in the formed tin oxide nanotube structure through the component analysis (EDS) images by the TEM analysis.

Comparative Example 3: Fabrication of Pure Tin Oxide Nanofiber not Containing Nanoparticle Catalyst As Comparative Example 3 to be compared with Embodiment Example 3, a pure tin oxide nanofiber is fabricated by not adding a nanoparticle catalyst embedded in an apoferritin. Specifically, 0.35 g of polyvinylpyrrolidone (PVP) polymer having an average weight of 1,300,000 g/mol and 0.25 g of tin chloride dihydrate of the tin oxide precursor are dissolved in a mixed solvent composed of 1.35 g of DMF and 1.35 g of ethanol at room temperature for about 24 hours under a condition of 500 rpm. After the stirring is completed, the tin oxide precursor/polymer mixed electrospinning solution is filled in the syringe for electrospinning (Henke-Sass Wolf, 10 mL NORM-JECT®), the syringe is connected to the syringe pump, the electrospinning solution is pushed out at a discharge speed of 0.1 ml/min, the needle used during electrospinning is a 27 gauge needle, and a high voltage of about 14 kV is applied while maintaining the distance between the nozzle the collector to collect the nanofibers to be 15 cm, thereby fabricating the tin oxide precursor/polymer composite nanofiber web. The tin oxide precursor/polymer composite nanofiber fabricated above is subjected to a high-temperature heat treatment to remove the polymer, and the tin oxide precursor is converted to tin oxide by oxidation. The high-temperature heat treatment is conducted for 1 hour at 600° C., the heating rate is constantly maintained at 4° C./min, and the cooling rate is constantly maintained at 40° C./min.

Figure 22:
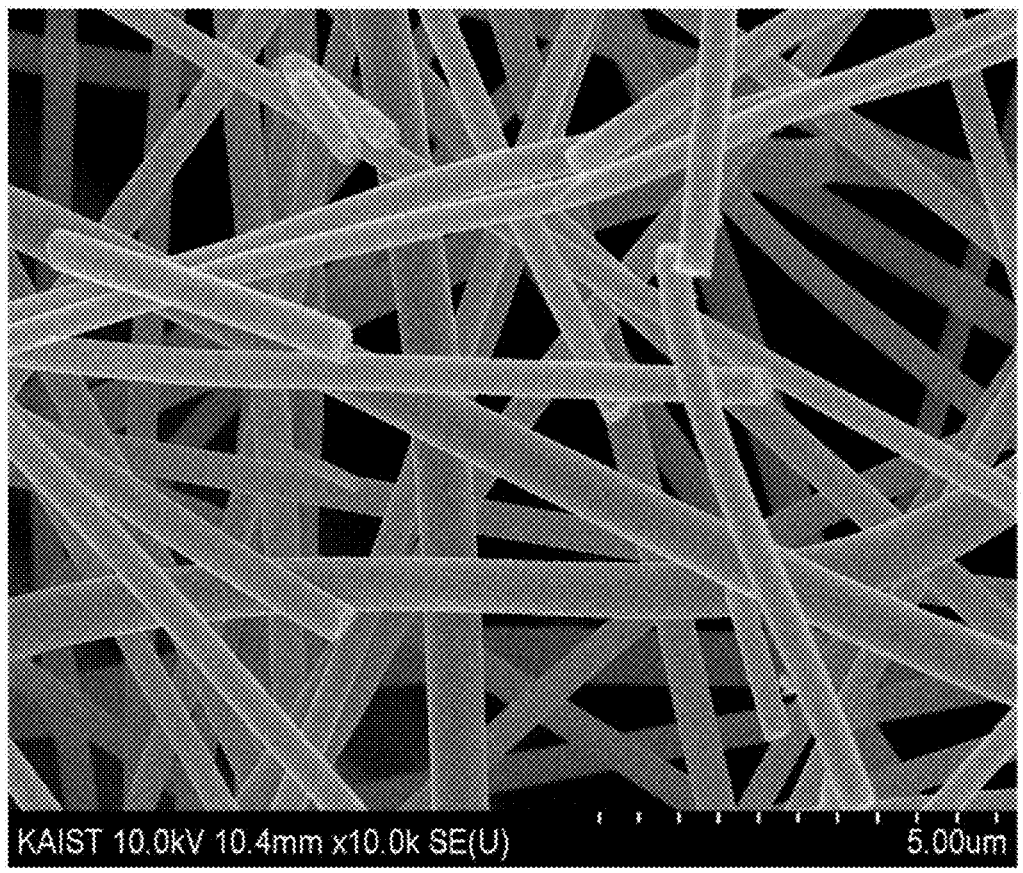
FIG. 22 is a SEM image of a tin oxide nanofiber obtained by electrospinning a tin oxide precursor/polyvinylpyrrolidone (PVP) composite electrospinning solution and conducting a high-temperature heat treatment according to Comparative Example 3 of the inventive concept.

FIG. 22 is a SEM image of the pure tin oxide nanofiber fabricated not by adding a nanoparticle catalyst in Comparative Example 3. It can be seen that the tin oxide nanofiber thus fabricated has a diameter of about from 50 nm to 2 μm and the nanofiber structure has a cylindrical structure.

The pure tin oxide nanofiber fabricated above is was used for comparison on the sensing characteristics with respect to various kinds of gases together with the tin oxide nanotube loaded with the Pt nanoparticle catalyst and tin oxide nanotube loaded with the Au nanoparticle catalyst fabricated in Embodiment Example 4.

Comparative Example 4: Fabrication of Pure Tin Oxide Nanotube not Containing Nanoparticle Catalyst As Comparative Example 4 to be compared with Embodiment Example 4, a pure tin oxide nanotube is fabricated by not adding Pt and Au nanoparticle catalysts embedded in an apoferritin. Specifically, 0.35 g of polyvinylpyrrolidone (PVP) polymer having an average weight of 1,300,000 g/mol and 0.25 g of tin chloride dihydrate of the tin oxide precursor are dissolved in a mixed solvent composed of 1.35 g of DMF and 1.35 g of ethanol at room temperature for about 24 hours under a condition of 500 rpm. After the stirring is completed, the tin oxide precursor/polymer mixed electrospinning solution is filled in the syringe for electrospinning (Henke-Sass Wolf, 10 mL NORM-JECT®), the syringe is connected to the syringe pump, the electrospinning solution is pushed out at a discharge speed of 0.1 ml/min, the needle used during electrospinning is a 27 gauge needle, and a high voltage of about 14 kV is applied while maintaining the distance between the nozzle the collector to collect the nanofibers to be 15 cm, thereby fabricating the tin oxide precursor/polymer composite nanofiber.

The tin oxide precursor/polymer composite nanofiber thus synthesized is subjected to a high-temperature heat treatment to remove the polymer, and the tin oxide precursor is converted to tin oxide by oxidation. The high-temperature heat treatment is conducted for 1 hour at 600° C., the heating rate is constantly maintained at 10° C./min, and the cooling rate is constantly maintained at 40° C./min. Here, the heating rate is set to 10° C./min in order to increase the temperature at a higher speed than in Comparative Example 3 in which the heating rate is set to 4° C./min, and this is for the formation of the nanotube structure.

Figure 23:
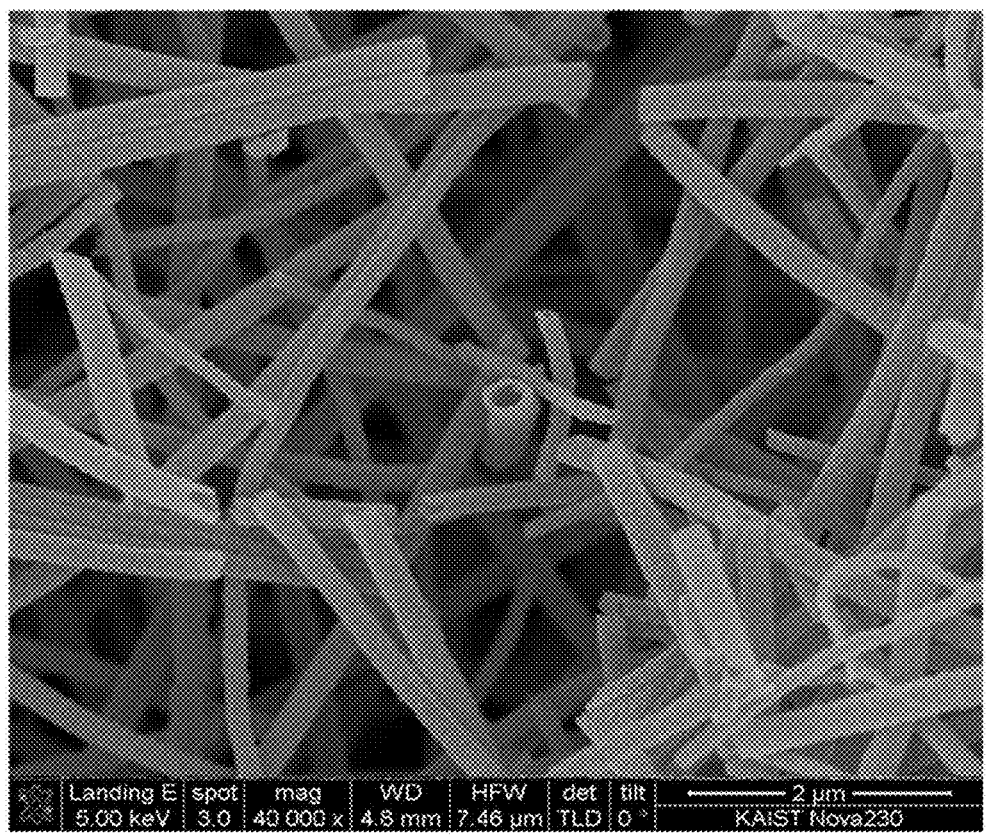
FIG. 23 is a SEM image of a tin oxide nanotube obtained by electrospinning a tin oxide precursor/polyvinylpyrrolidone (PVP) composite electrospinning solution and conducting a high-temperature heat treatment under a high heating rate condition according to Comparative Example 4 of the inventive concept.

FIG. 23 is a SEM image of the tin oxide nanotube fabricated in Comparative Example 4. The outer diameter of the pure tin oxide nanotube thus fabricated has a size of about from 50 nm to 2 μm and the inner diameter thereof has a size of about from 40 nm to 1.9 μm. The thickness of the tube is about from 10 to 100 nm.

Experimental Example 2: Manufacture of Gas Sensor Using Tin Oxide Nanotube Loaded with Platinum (Pt) Nanoparticle Catalyst, Tin Oxide Nanotube Loaded with Gold (Au) Nanoparticle Catalyst, Pure Tin Oxide Nanotube, and Pure Tin Oxide Nanofiber, and Evaluation on Characteristics Thereof In order to manufacture exhaled breath sensors using the sensing materials for gas sensor fabricated in Embodiment Examples 3 and 4 and Comparative Examples 3 and 4, 5 mg of each of the tin oxide nanotube loaded with the platinum (Pt) nanoparticle catalyst that is partially oxidized through the high-temperature heat treatment, the tin oxide nanotube loaded with the gold (Au) nanoparticle catalyst that is partially oxidized through the high-temperature heat treatment, the pure tin oxide nanotube, and the pure tin oxide nanofiber is dispersed in 100 μl of ethanol and subjected to the ultrasonic cleaning for 1 hour to be ground. During the grinding, the nanotube structure synthesized above may have a nanotube structure shortened in the longitudinal direction or a nano-rod structure.

The tin oxide nanotube 1810 loaded with the Pt nanoparticle catalyst or the Au nanoparticle catalyst, the pure tin oxide nanofiber, and the pure tin oxide nanotube are coated on the upper portion of the alumina substrate which has a size of 3 mm×3 mm and on which parallel gold (Au) electrodes are formed at an interval of 300 μm by drop coating. As the coating process, 2 μl of a mixed solution of the tin oxide nanotube loaded with the Pt nanoparticle catalyst, the tin oxide nanotube loaded with the Au nanoparticle catalyst, the pure tin oxide nanotube, and the pure tin oxide nanofiber dispersed in ethanol was respectively coated on the alumina substrate having the sensor electrode using a micropipette and dried on a hot plate at 60° C., and this process was repeated 4 to 6 times so as to coat a sufficient amount of the tin oxide nanotube loaded with the Pt nanoparticle catalyst, the tin oxide nanotube loaded with the Au nanoparticle catalyst, the pure tin oxide nanotube, and the pure tin oxide nanofiber on the upper portion of the alumina sensing plate.

In addition, the response characteristics of the gas sensor thus fabricated with respect to acetone ($CH_3COCH_3$), hydrogen sulfide ($H_2S$), and toluene ($C_6H_5CH_3$) of the biomarker gas for the diagnosis of diabetes, halitosis, and lung cancer, respectively, were evaluated at a relative humidity of 85-95% RH to be similar to the humidity of gases in the exhaled breath of a human body by changing the concentration of the respective gases from 5 to 4, 3, 2, and 1 ppm and maintaining the driving temperature of the sensor at 350° C. at the same time. In addition, in Experimental Example 2, the selective gas sensing characteristics were investigated by evaluating the sensing characteristics not only for acetone ($CH_3COCH_3$), hydrogen sulfide ($H_2S$), and toluene ($C_6H_5CH_3$) of the representative examples of the volatile organic compound gas but also for nitric oxide (NO), carbon monoxide (CO), ammonia ($NH_3$), and pentane ($C_5H_{12}$) of the biomarker gas of asthma, chronic obstructive pulmonary disease, nephritis, and heart disease.

Figure 28:
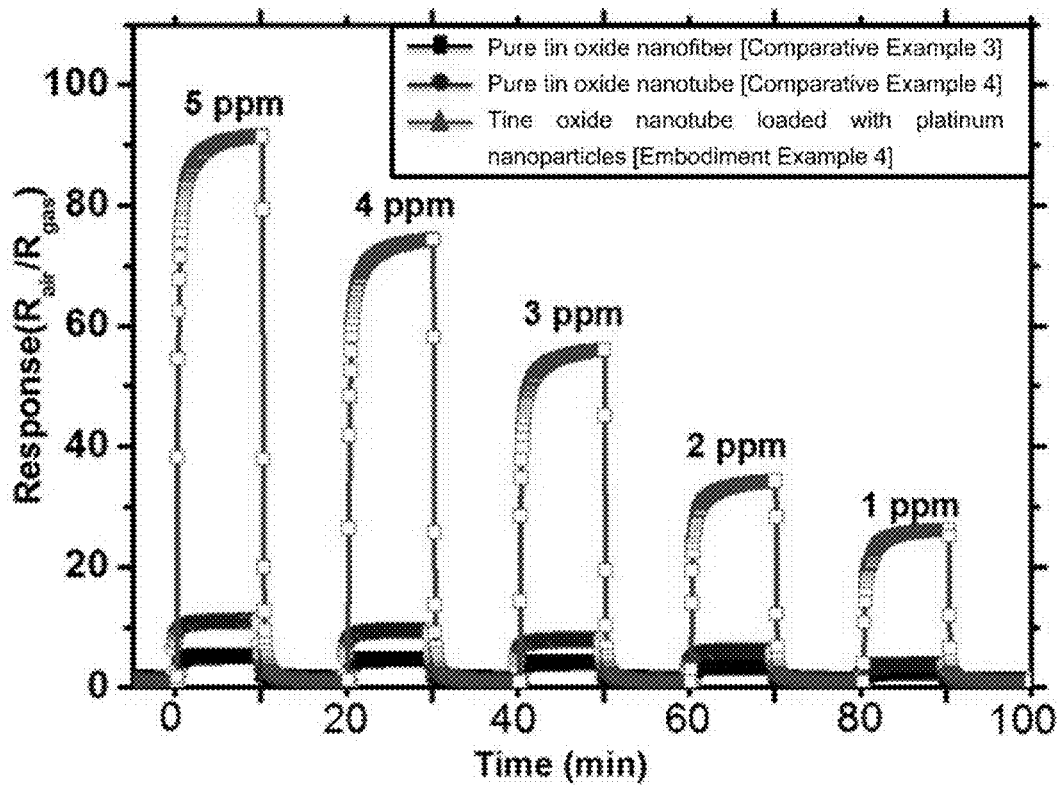
FIG. 28 is a graph illustrating the acetone (1 to 5 ppm) response properties of a tin oxide nanotube containing a Pt nanoparticle catalyst according to Embodiment Example 4 of the inventive concept, a pure tin oxide nanotube structure according to Comparative Example 4, and a tin oxide nanotube structure according to Comparative Example 3 at 350° C.

FIG. 28 is a graph illustrating the time course response properties ($R_{air}/R_{gas}$, where $R_{air}$ means the resistance value of the metal oxide material when the air is injected, and $R_{gas}$ means the resistance value of the metal oxide material when acetone is injected) when the concentration of acetone decreases from 5 to 4, 3, 2, and 1 ppm at 350° C.

As illustrated in FIG. 28, the sensing characteristics of the sensor manufactured using the tin oxide nanotube 1810 on which the Pt nanoparticle catalyst embedded in the apoferritin is loaded through the heat treatment with respect to acetone is 8.27 times as high as that of the pure tin oxide nanotube and 18.95 times as high as that of the pure tin oxide nanofiber.

Figure 29:
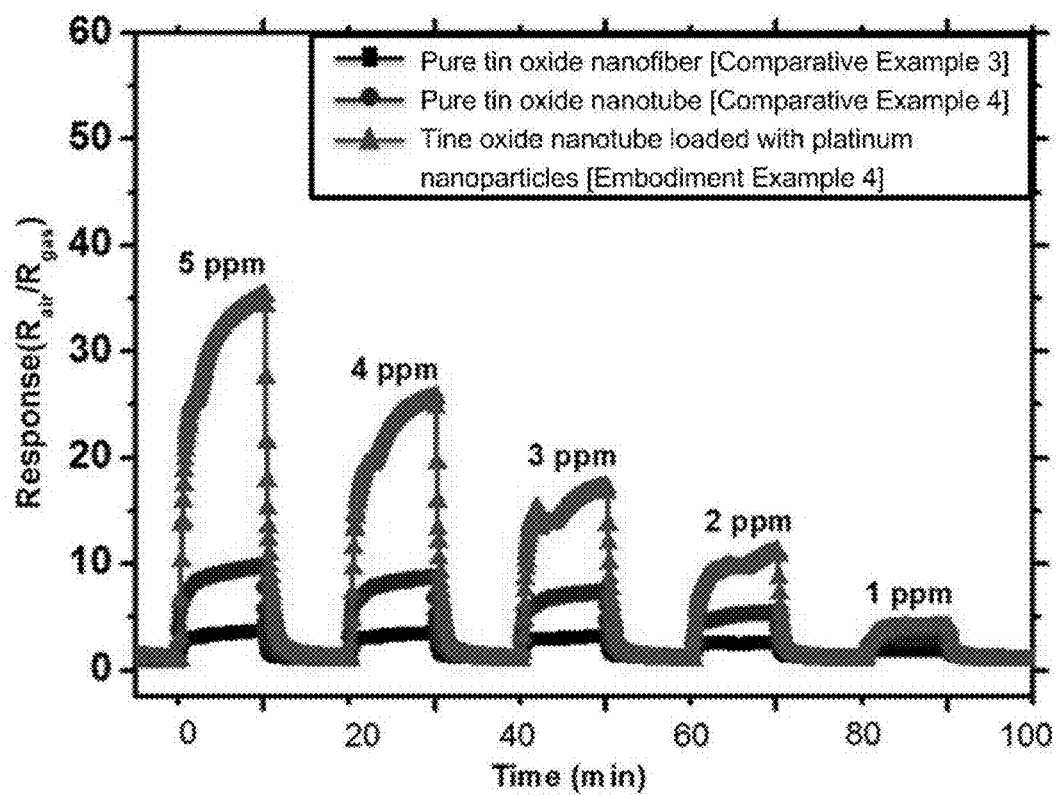
FIG. 29 is a graph illustrating the hydrogen sulfide (1 to 5 ppm) response properties of a tin oxide nanotube containing a Pt nanoparticle catalyst according to Embodiment Example 4 of the inventive concept, a pure tin oxide nanotube structure according to Comparative Example 4, and a tin oxide nanotube structure according to Comparative Example 3 at 350° C.

FIG. 29 is a graph illustrating the sensor test results showing the time course response properties when the concentration of hydrogen sulfide decreases from 5 to 4, 3, 2, and 1 ppm at 350° C.

As illustrated in FIG. 29, the sensing characteristics of the sensor manufactured using the tin oxide nanotube 1810 on which the Pt nanoparticle catalyst embedded in the apoferritin is loaded through the heat treatment with respect to hydrogen sulfide is 4.23 times as high as that of the pure tin oxide nanotube and 11.03 times as high as that of the pure tin oxide nanofiber.

Figure 30:
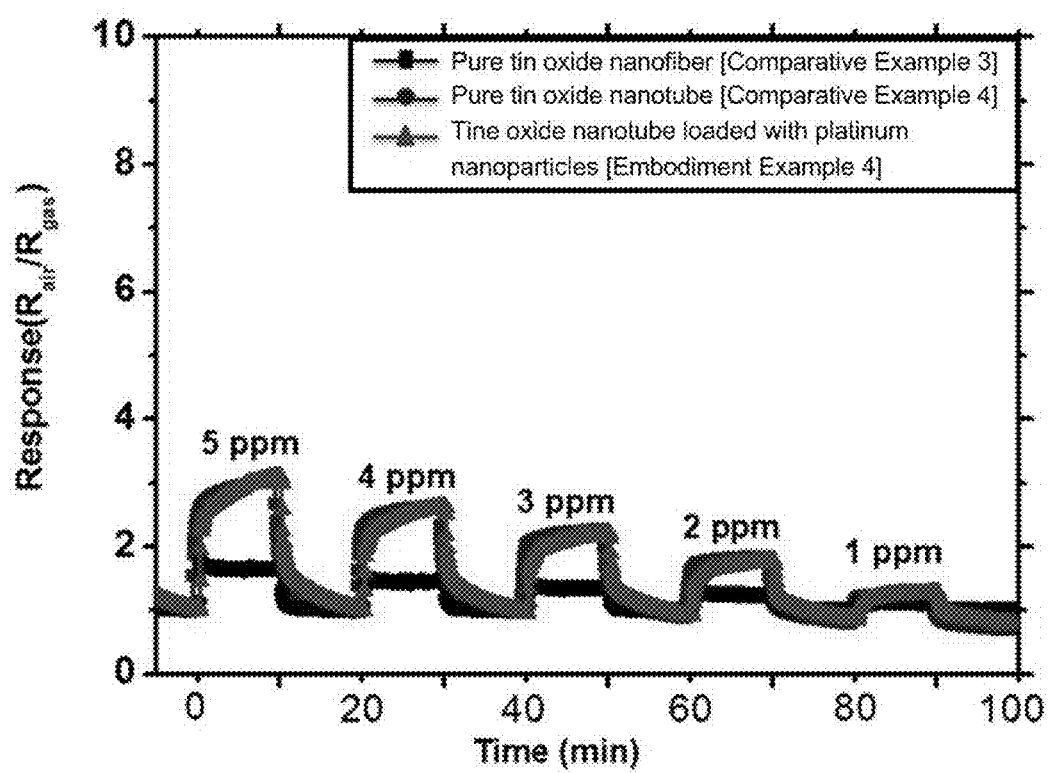
FIG. 30 is a graph illustrating the toluene (1 to 5 ppm) response properties of a tin oxide nanotube containing a Pt nanoparticle catalyst according to Embodiment Example 4 of the inventive concept, a pure tin oxide nanotube structure according to Comparative Example 4, and a tin oxide nanotube structure according to Comparative Example 3 at 350° C.

FIG. 30 is a graph illustrating the sensor test results showing the time course response properties when the concentration of toluene decreases from 5 to 4, 3, 2, and 1 ppm at 350° C.

As illustrated in FIG. 30, the sensing characteristics of the sensor manufactured using the tin oxide nanotube 1810 on which the Pt nanoparticle catalyst embedded in the apoferritin is loaded through the heat treatment with respect to toluene is 1.12 times as high as that of the pure tin oxide nanotube and 1.76 times as high as that of the pure tin oxide nanofiber.

Figure 31:
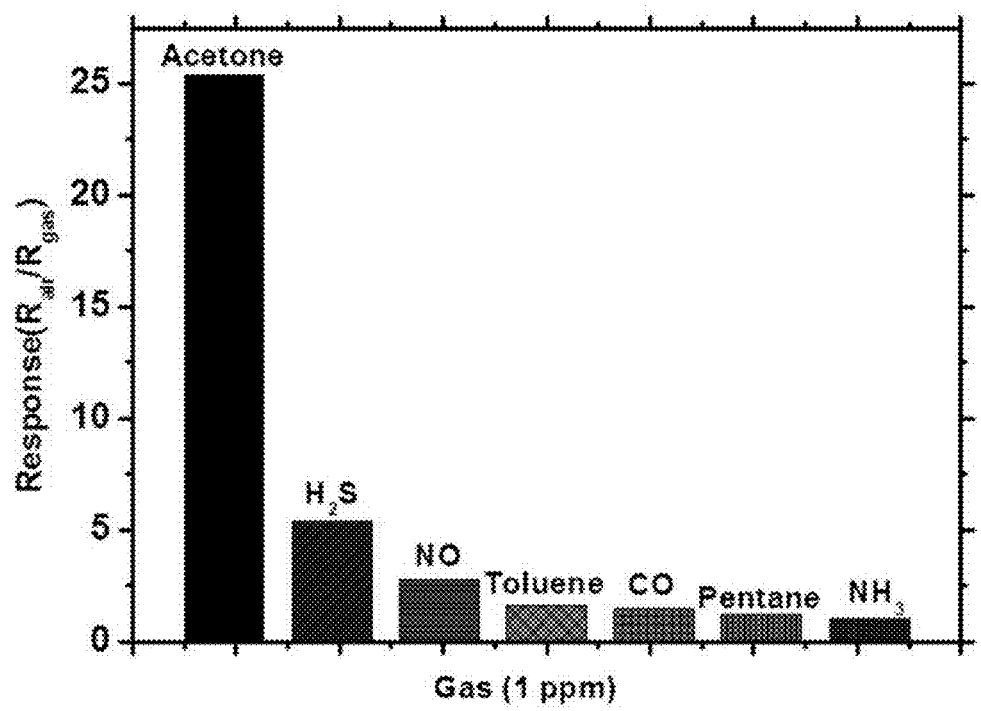
FIG. 31 is a graph illustrating the response properties of a gas sensor using tin oxide having a one-dimensional nanotube structure loaded with a Pt nanoparticle catalyst according to Embodiment Example 4 of the inventive concept to biomarker gases such as acetone ($CH_3COCH_3$), toluene ($C_6H_5CH_3$), hydrogen sulfide ($H_2S$), nitrogen monoxide (NO), carbon monoxide (CO), pentane ($C_5H_{12}$), and ammonia ($NH_3$) at 1 ppm and 350° C.

FIG. 31 is a graph illustrating the response value of the sensor manufactured using the tin oxide nanotube on which the Pt nanoparticle catalyst embedded in the apoferritin is loaded through the heat treatment with respect to hydrogen sulfide, toluene, nitrogen monoxide, carbon monoxide, ammonia, and pentane of biomarker gases of other diseases together with the response value with respect to acetone of the biomarker gas of diabetes and lipolysis at a concentration of 1 ppm and 350° C.

As illustrated in FIG. 31, the gas sensor manufactured using the tin oxide nanotube 1810 on which the Pt nanoparticle catalyst embedded in the apoferritin is loaded through the heat treatment exhibits specifically excellent selective sensing characteristics with respect to acetone of the biomarker gas of diabetes and lipolysis compared to hydrogen sulfide, toluene, pentane, carbon monoxide, ammonia, and nitrogen monoxide of biomarker gases of other diseases.

Figure 32:
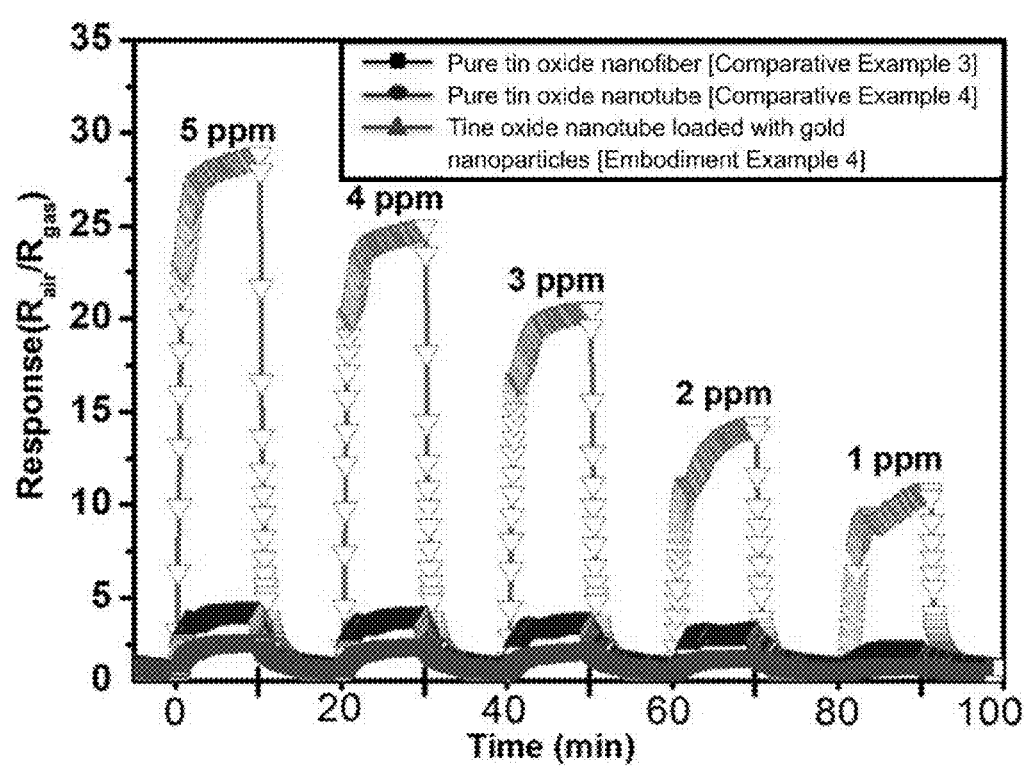
FIG. 32 is a graph illustrating the hydrogen sulfide (1 to 5 ppm) response properties of a tin oxide nanotube containing an Au nanoparticle catalyst according to Embodiment Example 4 of the inventive concept, a pure tin oxide nanotube structure according to Comparative Example 4, and a tin oxide nanotube structure according to Comparative Example 3 at 350° C.

FIG. 32 is a graph illustrating the hydrogen sulfide (1 to 5 ppm) response properties of the sensor manufactured using the tin oxide nanotube which is fabricated in Embodiment Example 4 on which the gold (Au) nanoparticle catalyst embedded in the apoferritin is loaded through the heat treatment.

Figure 33:
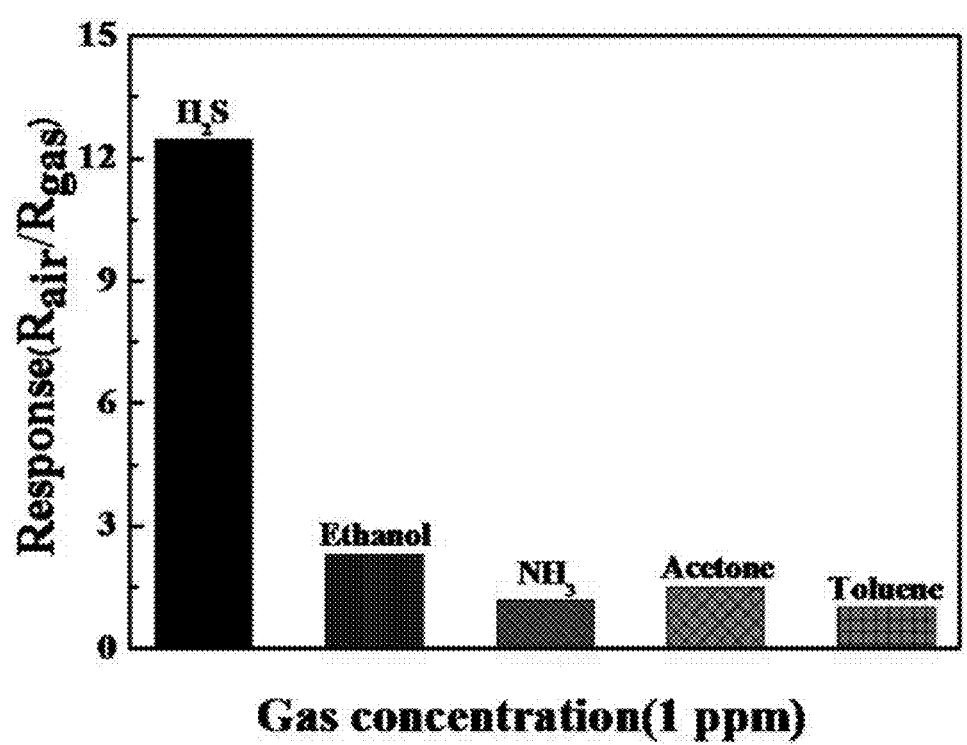
FIG. 33 is a graph illustrating the response properties of a gas sensor using tin oxide having a one-dimensional nanotube structure loaded with an Au nanoparticle catalyst according to Embodiment Example 4 of the inventive concept to biomarker gases such as acetone ($CH_3COCH_3$), toluene ($C_6H_5CH_3$), hydrogen sulfide ($H_2S$), ethanol ($C_2H_5OH$), and ammonia ($NH_3$) at 1 ppm and 300° C.

FIG. 33 is a graph illustrating the response value of the sensor manufactured using the tin oxide nanotube on which the gold (Au) nanoparticle catalyst embedded in the apoferritin is loaded through the heat treatment with respect to toluene, acetone, ammonia, and ethanol of biomarker gases of other diseases together with the response value with respect to hydrogen sulfide of the biomarker gas of diabetes and lipolysis at a concentration of 1 ppm and 300° C.

In Experimental Example 2, the sensing characteristics of the gas sensing material with respect to the volatile organic compound gases are evaluated. However, it is expected that the gas sensing material exhibits excellent sensing characteristics with respect to $H_2$, $NO_x$, $SO_x$, HCHO, $CO_2$ of harmful environmental gases as well, and it has been confirmed that a gas sensor exhibiting excellent selectivity to acetone and hydrogen sulfide is manufactured by changing the kind of the catalyst in the sensor manufactured using the tin oxide nanotube on which the platinum (Pt) or gold (Au) nanoparticle catalyst embedded in the apoferritin is loaded through the heat treatment. In addition, it is possible to manufacture a nanosensor array exhibiting ultrahigh sensitivity and high selectivity by using a multi-kind metal oxide nanotube loaded with various kinds of catalyst particles since additional change in selectivity is expected by changing the kind of metal oxide materials. The metal oxide nanotube sensing material loaded with a nanoparticle catalyst obtained from an apoferritin template can be used in an excellent gas sensor for detection of harmful environmental gases and a gas sensor for healthcare for volatile organic compound gas analysis in the exhaled breath and diagnosis of a disease.

While the inventive concepts have been described with reference to example embodiments, it will be apparent to those skilled in the art that various changes and modifications may be made without departing from the spirits and scopes of the inventive concepts. Therefore, it should be understood that the above embodiments are not limiting, but illustrative. Thus, the scopes of the inventive concepts are to be determined by the broadest permissible interpretation of the following claims and their equivalents, and shall not be restricted or limited by the foregoing description.

REFERENCE NUMERALS

- 100: one-dimensional porous metal oxide nanotube gas sensor member which contains nanoparticle catalyst and has double pore distribution including great number of circular or elliptical pores
- 110: nanoparticle catalyst in partially oxidized state after removal of apoferritin shell through high-temperature heat treatment
- 121: circular or elliptical macropores formed as spherical polystyrene sacrificial template is decomposed through high-temperature heat treatment and macropores are filled by crystallization and diffusion of metal oxide
- 131: macropores formed as spherical polystyrene sacrificial template is decomposed through high-temperature heat treatment
- 1800: metal oxide nanotube gas sensor member containing nanoparticle catalyst
- 1810: metal oxide nanotube containing nanoparticle catalyst
- 1821: nanoparticle catalyst in partially oxidized state after removal of apoferritin shell through high-temperature heat treatment
- 2010: tin oxide precursor/polymer electrospinning solution embedding apoferritin containing Pt nanoparticle catalyst or Au nanoparticle catalyst
- 2020: Pt nanoparticle catalyst synthesized using apoferritin
- 2030: tin oxide precursor/polymer nanofiber containing apoferritin containing Pt nanoparticle catalyst or Au nanoparticle catalyst
- 2040: tin oxide nanotube containing partially oxidized Pt nanoparticle catalyst or Au nanoparticle catalyst
- 2050: partially oxidized Pt nanoparticle catalyst or Au nanoparticle catalyst after removal of apoferritin shell through high-temperature heat treatment

What is claimed is:

1. A one-dimensional porous metal oxide nanotube composite sensing material, which has a double average surface pore distribution of macropores and mesopores, wherein metallic nanoparticle catalysts are uniformly distributed on a metal oxide nanotube and at the same time the macropores and mesopores are formed on a surface of the metal oxide nanotube during a heat treatment of a metal oxide precursor/polymer composite nanofiber having a plurality of spherical polymer sacrificial templates and metallic nanoparticle catalysts embedded in inner hollow structures of apoferritins and encapsulated in a protein dispersed in the inside and on the outer surface thereof.

2. The one-dimensional porous metal oxide nanotube composite sensing material according to claim 1, wherein the metallic nanoparticle catalysts are uniformly loaded in an inside and on an inner surface and an outer surface of a shell constituting the metal oxide nanotube.

3. The one-dimensional porous metal oxide nanotube composite sensing material according to claim 1, wherein
a diameter of the macropores is in a range of from 50 nm to 300 nm and
a diameter of the mesopores is in a range of from 0.1 nm to 50 nm.

4. The one-dimensional porous metal oxide nanotube composite sensing material according to claim 1, wherein the spherical polymer sacrificial template used when forming the macropores includes one kind or a mixture of two or more kinds selected from polymethyl methacrylate (PMMA), polyvinylpyrrolidone (PVP), polyvinyl acetate (PVAc), polyvinyl alcohol (PVA), polystyrene (PS), polyacrylonitrile (PAN), polyvinylidene fluoride (PVDF), polyacrylic acid (PAA), polydiallyldimethylammonium chloride (PDADMAC), or polystyrene sulfonate (PSS) and is dispersed without being decomposed when mixed with an electro spinning solution.

5. The one-dimensional porous metal oxide nanotube composite sensing material according to claim 1, wherein
the spherical polymer sacrificial template used when forming the macropores includes a polymer colloid insoluble in a solvent as a charged ion or a charged anionic or cationic surfactant is formed on a surface of the colloid although the sacrificial colloid is a polymer soluble in the solvent, and
a size of the spherical polymer sacrificial template is selected from a range of from 50 nm to 1 µm.

6. The one-dimensional porous metal oxide nanotube composite sensing material according to claim 1, wherein
there is a time difference between decomposition of the spherical polymer sacrificial template and crystallization and diffusion of the metal oxide during the heat treatment, and
macropores formed on a surface of the metal oxide nanotube by decomposition of the spherical polymer sacrificial template are partially filled through the crystallization and diffusion of the metal oxide.

7. The one-dimensional porous metal oxide nanotube composite sensing material according to claim 1, wherein
a weight ratio (wt %) of the spherical polymer sacrificial template to the metallic nanoparticle catalyst embedded in the inner hollow structure of the apoferritin and encapsulated in the protein is in a range of from 1:0.000001 to 1.

8. The one-dimensional porous metal oxide nanotube composite sensing material according to claim 1, wherein
a porous metal oxide nanotube contains a metal oxide including a single material of one kind or a composite of two or more kinds selected from $SnO_2$, $WO_3$, $Co_3O_4$, $ZnO$, $Fe_2O_3$, $NiO$, $In_2O_3$, $Mn_2O_3$, $V_2O_3$, $MoO_3$, $Fe_3O_4$, $V_2O_5$, $Zn_2SnO_4$, $LaCoO_3$, $CeO_2$, $Eu_2O_3$, $Gd_2O_3$, $HoO_3$, $Er_2O_3$, $Yb_2O_3$, $Lu_2O_3$, $LiV_3O_8$, $SrTiO_3$, $ZrO_2$, $CuO$, $InTaO_4$, $Nd_2O_3$ or $Sm_2O_3$.

9. The one-dimensional porous metal oxide nanotube composite sensing material according to claim 1, wherein
a weight ratio (wt %) of the spherical polymer sacrificial template is in a concentration range of from 0.1 wt % to 50 wt % with respect to a polymer matrix constituting the nanofiber.

10. The one-dimensional porous metal oxide nanotube composite sensing material according to claim 1, wherein
a weight ratio (wt %) of the metallic nanoparticle catalyst embedded in the inner hollow structure of the apoferritin and encapsulated in the protein is in a concentration range of from 0.001 wt % to 50 wt % with respect to a metal oxide precursor constituting the metal oxide precursor/polymer composite nanofiber.

11. The one-dimensional porous metal oxide nanotube composite sensing material according to claim 1, wherein
the protein contains an apoferritin having a hollow structure having an inner diameter of 8 nm and an outer diameter of 12 nm and is densely present in between the spherical polymer sacrificial templates in the metal oxide precursor/polymer composite nanofiber containing the spherical polymer sacrificial templates, and the one-dimensional porous metal oxide nanotube composite sensing material has the double average surface pore distribution of the mesopores formed as the shell of the protein constituting the hollow structure in a dense region is removed by thermal decomposition through the heat treatment and the macropores formed by the spherical polymer sacrificial template.

12. The one-dimensional porous metal oxide nanotube composite sensing material according to claim 1, wherein the metallic nanoparticle catalyst and the spherical polymer sacrificial template are charged so as to be uniformly dispersed on the surface and in the inside of the metal oxide precursor/polymer composite nanofiber without aggregation among the metallic nanoparticle catalysts and aggregation among the spherical polymer sacrificial templates.

13. The one-dimensional porous metal oxide nanotube composite sensing material according to claim 1, wherein the nanotube contained in the one-dimensional porous metal oxide nanotube composite sensing material has an outer diameter in a size range of from 50 nm to 2 µm, an inner diameter in a size range of from 40 nm to 1.95 µm, a thickness of the shell in a size range of from 10 nm to 50 nm, and the mesopores having a diameter in a range of from 0.1 nm to 50 nm and the macropores having a diameter in a range of from 50 nm to 300 nm on surfaces in all directions at an average interval of from 5 nm to 1 µm.

14. The one-dimensional porous metal oxide nanotube composite sensing material according to claim 1, wherein the metallic nanoparticle catalyst includes one kind or two or more kinds of nanoparticle catalysts selected from Pt, Pd, Rh, Ru, Ni, Co, Cr, Ir, Au, Ag, Zn, W, Sn, Sr, In, Pb, Fe, Cu, V, Ta, Sb, Sc, Ti, Mn, Ga, or Ge.

\* \* \* \* \*